(12) United States Patent
Wu et al.

(10) Patent No.: US 6,420,567 B1
(45) Date of Patent: *Jul. 16, 2002

(54) N-HETEROARYL ARYL-SUBSTITUTED THIENYL-FURYL-AND PYRROLYL-SULFONAMIDES AND DERVIATIVES THEREOF THAT MODULATE THE ACTIVITY OF ENDOTHELIN

(75) Inventors: Chengde Wu, Houston; Bore Gowda Raju; Timothy Kogan, both of Sugarland; Natalie Blok, Houston, all of TX (US)

(73) Assignee: Texas Biotechnology Corporation, Houston, TX (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/938,325

(22) Filed: Sep. 26, 1997

Related U.S. Application Data

(63) Continuation-in-part of application No. 08/721,183, filed on Sep. 27, 1996, now Pat. No. 5,962,490.

(51) Int. Cl.$^7$ .................... C07D 261/04; C07D 261/14; C07D 261/06; A61K 31/47

(52) U.S. Cl. ...................... 548/245; 514/311; 514/312; 514/313; 514/314; 514/378; 514/379; 514/380; 548/244; 548/247

(58) Field of Search .............................. 514/380, 311, 514/312, 313, 314, 378, 379; 548/244, 245, 247

(56) References Cited

U.S. PATENT DOCUMENTS

| | | | |
|---|---|---|---|
| 2,888,455 A | 5/1959 | Kano et al. | 260/239.9 |
| 3,300,488 A | 1/1967 | Onoue et al. | 260/239.9 |
| 3,660,383 A | 5/1972 | Sumimoto et al. | 260/239.9 |
| 3,710,795 A | 1/1973 | Higuchi et al. | 128/260 |
| RE28,819 E | 5/1976 | Thompson | 424/243 |
| 4,044,126 A | 8/1977 | Cook et al. | 424/243 |
| 4,328,245 A | 5/1982 | Yu et al. | 424/305 |
| 4,358,603 A | 11/1982 | Yu | 560/2 |
| 4,364,923 A | 12/1982 | Cook et al. | 424/46 |
| 4,409,239 A | 10/1983 | Yu | 424/305 |
| 4,410,545 A | 10/1983 | Yu et al. | 424/305 |
| 4,414,209 A | 11/1983 | Cook et al. | 424/243 |
| 4,485,108 A | 11/1984 | Jozic | 424/267 |
| 4,752,613 A | 6/1988 | Floyd et al. | 514/438 |
| 4,997,836 A | 3/1991 | Sugihara et al. | 514/253 |
| 5,082,838 A | 1/1992 | Naka et al. | 514/211 |
| 5,114,918 A | 5/1992 | Ishikawa et al. | 514/11 |
| 5,187,195 A | 2/1993 | Oohata et al. | 514/610 |
| 5,198,548 A | 3/1993 | Beylin et al. | 546/136 |
| 5,208,243 A | 5/1993 | Peglion et al. | 514/309 |

(List continued on next page.)

FOREIGN PATENT DOCUMENTS

| | | |
|---|---|---|
| AU | 5461286 | 3/1985 |
| CA | 2067288 | 10/1992 |
| CA | 2071193 | 12/1992 |
| EP | 0248399 | 12/1987 |
| EP | 0404525 | 12/1990 |
| EP | 0405421 | 1/1991 |
| EP | 0411150 | 2/1991 |
| EP | 0436189 | 7/1991 |
| EP | 0457195 | 11/1991 |
| EP | 0460679 | 12/1991 |
| EP | 0496452 | 7/1992 |
| EP | 0558258 | 9/1993 |
| EP | 0569193 | 11/1993 |
| EP | 0626174 A2 | 11/1994 |
| EP | 0640596 | 3/1995 |
| EP | 0682016 A1 | 11/1995 |
| EP | 0702012 A1 | 3/1996 |
| EP | 0725067 A1 | 8/1996 |
| EP | 0768305 A1 | 4/1997 |
| GB | 0804036 | 11/1958 |
| GB | 1473433 | 5/1977 |
| GB | 2259450 | 3/1993 |
| JP | 6018808 | 9/1985 |
| JP | 63238006 | 4/1990 |
| JP | 4134084 | 5/1992 |
| WO | 9115479 | 10/1991 |
| WO | 9308799 | 5/1993 |
| WO | 9427979 | 12/1994 |
| WO | 9524385 | 9/1995 |
| WO | 9604759 | 4/1996 |
| WO | 9631492 | 10/1996 |

OTHER PUBLICATIONS

Database Crossfire Beilstein Registry No. 1021364 and 1086426, citing Saito et al., *Yakugaku Zasshi* 88:1289, 1292 (1968).

Chemical Abstracts vol. 65, abstract No. 14649g, citing Uno et al., *Chem. Pharm. Bull.* 14:756–762 (1966).

Allen et al., The Cambridge crystallographic data centre: Computer–based search, retrieval, analysis and display of information, *Acta Crystallogr. B35*:2331–2339 (1979).

(List continued on next page.)

*Primary Examiner*—Floyd D. Higel
(74) *Attorney, Agent, or Firm*—Stephanie L. Seidman; Dale L. Rieger; Heller Ehrman White McAuliffe LLP

(57) ABSTRACT

Thienyl-, furyl- and pyrrolyl-sulfonamides, formulations of pharmaceutically-acceptable salts thereof and methods for modulating or altering the activity of the endothelin family of peptides are provided. In particular, N-(isoxazolyl) thienylsulfonamides, N-(isoxazolyl)furylsulfonamides and N-(isoxazolyl)pyrrolylsulfonamides, formulations thereof and methods using these sulfonamides for inhibiting the binding of an endothelin peptide to an endothelin receptor by contacting the receptor with the sulfonamide are provided. Methods for treating endothelin-mediated disorders by administering effective amounts of one or more of these sulfonamides or prodrugs thereof that inhibit the activity of endothelin are also provided.

73 Claims, No Drawings

U.S. PATENT DOCUMENTS

| | | | |
|---|---|---|---|
| 5,230,999 A | 7/1993 | Suzuki et al. | 435/71 |
| 5,240,910 A | 8/1993 | Lam et al. | 514/11 |
| 5,248,807 A | 9/1993 | Fujimoto et al. | 560/75 |
| 5,270,313 A | 12/1993 | Burri et al. | 514/11 |
| 5,292,740 A | 3/1994 | Burri et al. | 514/256 |
| 5,334,598 A | 8/1994 | Bagley et al. | 514/303 |
| 5,352,659 A | 10/1994 | Wakimasu et al. | 514/9 |
| 5,352,800 A | 10/1994 | Bills et al. | 548/539 |
| 5,378,715 A | 1/1995 | Stein et al. | 514/329 |
| 5,382,569 A | 1/1995 | Cody et al. | 514/17 |
| 5,389,620 A | 2/1995 | Ishikawa et al. | 514/80 |
| 5,389,633 A | 2/1995 | Miyake et al. | 514/233.2 |
| 5,407,941 A | 4/1995 | Carceller et al. | 514/290 |
| 5,420,123 A | 5/1995 | Murugesan | 514/220 |
| 5,420,129 A | 5/1995 | Breu et al. | 514/252 |
| 5,420,131 A | 5/1995 | Carceller et al. | 514/253 |
| 5,420,133 A | 5/1995 | Dhanoa et al. | 514/256 |
| 5,420,138 A | 5/1995 | Corbier et al. | 514/300 |
| 5,420,275 A | 5/1995 | Masuya et al. | 544/236 |
| 5,464,853 A | 11/1995 | Chan et al. | 514/378 |
| 5,514,691 A | 5/1996 | Chan et al. | 514/312 |
| 5,514,696 A | 5/1996 | Murugesan et al. | 514/380 |
| 5,565,485 A | 10/1996 | Bagley et al. | 514/452 |
| 5,571,821 A | 11/1996 | Chan et al. | 514/312 |
| 5,585,397 A | 12/1996 | Tung et al. | 514/473 |
| 5,589,478 A | 12/1996 | Yamada et al. | 514/269 |
| 5,591,728 A | 1/1997 | de Nanteuil et al. | 514/80 |
| 5,591,761 A | 1/1997 | Chan et al. | 514/380 |
| 5,594,021 A | 1/1997 | Chan et al. | 514/378 |
| 5,599,811 A | 2/1997 | Berryman et al. | 514/226.5 |
| 5,612,359 A | 3/1997 | Murugesan | 514/365 |
| 5,641,793 A | 6/1997 | Bradbury | 514/352 |
| 5,668,137 A | 9/1997 | Phillips et al. | 514/255 |
| 5,668,176 A | 9/1997 | Bagley et al. | 514/569 |
| 5,726,194 A | 3/1998 | Osswald et al. | 514/362 |
| 5,783,701 A | 7/1998 | Tung et al. | 546/169 |
| 5,783,705 A | 7/1998 | Blok et al. | 548/247 |
| 5,804,585 A | 9/1998 | Verner | 514/301 |
| 5,827,869 A | 10/1998 | Murugesan | 514/374 |
| 5,962,490 A | 10/1999 | Chan et al. | 514/380 |
| 5,977,117 A | 11/1999 | Chan et al. | 514/256 |
| 6,013,655 A | 1/2000 | Verner | 514/301 |
| 6,030,991 A | 2/2000 | Chan et al. | 514/380 |
| 6,080,774 A | 6/2000 | Murugesan et al. | 514/380 |
| 6,083,851 A | 7/2000 | Bradbury | 514/256 |

OTHER PUBLICATIONS

Anagnostou et al., Erythropoietin has mitogenic and positive chemotactic effects on endothelial cells, *P.N.A.S.* 87:5978–5982 (1990).

Ansel, *Introduction to Pharmaceutical Dosage Forms*, 4th Edition, pp. 126–163 (1985).

Arai et al., Cloning and expression of a cDNA encoding an endothelin receptor, *Nature* 348:730–732 (1990).

Aumelas et al., Determination of the structure of [Nle$^7$] –endothelin by $^1$H NMR, *Int. J. Peptide Protein Res.* 37:315–324 (1991).

Balasubramanian, New type of representation for mapping chain folding in protein molecules, *Nature* 266:856–857 (1977).

Benigni et al., A specific endothelin subtype A receptor antagonist protects against injury in renal disease progression, *Kidney International* 44:440–444 (1993).

Bolger et al., Characterization of binding of the Ca$^{++}$channel antagonist [$^3$H] nitrendipine, to guinea–pig ileal smooth muscle, *J. Pharmacol. Exptl. Ther.* 225:291–309 (1983).

Borges et al., Tissue selectivity of endothelin, *Eur. J. Pharmacol.* 165:223–230 (1989).

Brint et al., Upperbound procedures for the identification of a similar three–dimensional chemical structures, *J. Comput.–Aided Mol. Design* 2:311–310 (1988).

Brooks et al., Effect of nifedipine on cyclosporine A–induced nephrotoxicity, urinary endothelial excretion and renal endothelin receptor No., *Eur. J. of Pharmacology* 194:115–117 (1991).

Buemi et al., Influence of recombinant erythroproietin on the production of endothelin–1 from human umbilical artery, *Nephron* 64(1):165–166 (1993).

Cardell et al., Two functional endothelin receptors in guinea–pig pulmonary arteries, *Neurochem. Int.* 18(4):571–574 (1991).

Carlini et al., Intravenous erythropoietin (rHuEPO) administration increases plasma endothelin and blood pressure in hemodialysis patients, *Am. J. Hyper.* 6:103–107 (1993).

Castiglione et al., Alanine scan of endothelin, Peptides: Chemistry and Biology, Proc. Amer. Rept. Symp. (12th), J.A. Smith and J.E. Rivier, Eds., ESCOM, Leiden, 1992, pp. 402–403.

Clarke et al., Endothelin is a potent long–lasting vasoconstrictor in men, *Am. J. Physiol.* 257(6 pt 2):H2033–H2035 (1989).

Clozel et al., Pathophysiological role of endothelin revealed by the first orally active endothelial receptor antagonist, *Nature* 365:759–761, (1993).

Cody et al., The rational design of a highly potent combined $ET_A$ and $ET_B$ receptor antagonist (PD145065) and related analogues, *Med. Chem. Res.* 3:154–162 (1993).

Cooper et al., A novel approach to molecular similarity, *J. Comput.–Aided Mol. Design* 3:253–259 (1989).

De Nucci et al., Pressor effects of circulating endothelin are limited by its removal in the pulmonary circulation and by the release of prostacyclin and endothelium–derived relaxing factor, *Proc. Natl. Acad. Sci.* 85:9797 (1988).

DiCarlo et al., $ET_A$–receptor antagonist prevents and reverse chronic hypoxia–induced pulmonary hypertension, *Am. J. Physiol.* 269:L690–L697 (1995).

Doherty, Endothelin: a new challenge, *J. Medicinal Chem.* 35(9):1493–1508 (1992).

Endothelin, Receptor Antagonist (TBC 11251), Research and Development—Compounds Under Development, pp. 3–5 (available at http://www.tbc.com/resrch.htm on Sep. 3, 1997).

Eschbach et al., Recombinant human erythropoietin in anemic patients with end stage renal disease; results of a phase III multicenter clinical trial, *Ann. Intern. Med.* 111: 992–1000 (1989).

Filep et al., Endothelin–1 induces prostacyclin release from bovine aortic endothelial cells, *Biochem. and Biophys. Research Comm.* 177(1):171–176 (1991).

Fujimoto et al., A novel non–peptide endothelin antagonist isolated from bayberry, *FEBS* 305(1):41–44 (1992).

Fujimoto et al., Isoxazole derivatives. II. Synthesis and structure of N–acylsufodiazoles and their homologs, *Chemical Abstracts:* 65(2), Abstract No. 2241eq. Jul. 18, 1966.

Furchgott et al., The obligatory role of endothelial cells in the relaxation of arterial smooth muscle by acetylcholine, *Nature* 288:373–376, (1980).

Galantino et al., D–Amino acid scan of endothelin, Peptides: Chemistry & Biology, Proc. Amer. Report. Symp. (12th), J.A. Smith and J.E. Rivier, Eds., ESCOM, Leiden, 1992, pp. 404–405.

Gibaldi, Chapter 8: Bioavailability, *Biopharmaceutics and Pharmacology*, 4th ed., Lea and Sediger, pp. 146–175 (1991).

Gu et al., The inhibitory effect of [D–Arg$^1$, D–Phe, D–Try$^{7,}$ 9, Leu$^{11}$] substance P on endothelin–1 binding sites in rat cardiac membranes, *Biochem. and Biophys. Research Commun.* 179(1):130–133 (1991).

Heidenreich et al., Erythropoietin induces contraction of isolated renal small resistance vessels, *Nephrol. Dial. Transplant* 5:739–740 (1990).

Hiley et al., Functional studies on endothelin catch up with molecular biology, *Trends Pharmacol. Sci.* 10:47–49 (1989).

Hirata et al., Receptor binding activity and cytosolic free calcium response by synthetic endothelin analogs in culture rat vascular smooth muscle cells, *Biochem. and Biophys. Research Commun.* 160:228–234 (1989).

Hori et al., Hemodynamics and volume changes by recombinant human erythropoietin (rHuEPO) in the treatment of anemic hemodialysis patients, *Clin. Nephrol.* 33:293–298 (1990).

Ihara et al., An endothelin receptor ($ET_A$) antagonist isolated from *Streptomyces Misakiensis*, *Biochem. and Biophys. Research Commun.* 178(1):132–137 (1991).

Ihara et al., Biological profiles of highly potent novel endothlin antagonists selective for the $ET_A$ receptor, *Life Sciences* 50:247–255 (1991).

Inoue et al., The human endothelin family: Three structurally and pharmacologically distinct isopeptides predicted by three separate genes, *Proc. Natl. Acad. Sci. USA*, 86:2863–2867 (1989).

Ishikawa et al., Cyclic pentapeptide endothelin antagonists with high $ET_A$ selectivity. Potency– and solubility–enhancing modifications, *J. Med. Chem.* 35:2139–2142 (1992).

IUPAC–IUB Commission on Biochemical Nomenclature, *Biochem.* 11:942–944, (1972).

Kanno et al., Endothelin–1 and Vasculitis, *J. Amer. Med. Assoc.* 264:2868, (1990).

Kaltenbronn et al., Renin inhibitors containing isosteric replacements of the amide bond connecting the $P_3$ and $P_2$ sites, *J. Med. Chem.* 33:838–845 (1990).

Karplus, Molecular Dynamics: Applications to Proteins, Computer Simulation of Chemical and Biomolecular Systems, (Bevendge and Jorfensen, Eds.) *Ann. New York Acad. Sci.*:482:255–266 (1986).

Kashiwabara et al., Putative precursors of endothelin have less vasoconstrictor activity in vitro but a potent pressor effect in vivo, *FEBS Letters* 247(1):73–76 (1989).

Kemp, Peptidomimetics and the template approach to nucleation of β–sheets and α–helices in peptides, *Trends in Biotech.* 8:249–255 (1990).

Kloog et al., Similarities in mode and sites of action of sarafotoxins and endothelins, *Trends Pharmacol. Sci.* 10:212–214 (1989).

Koyama et al., Plasma endothelin levels in patients with uremia, *Lancet* 1(8645):991–992 (1989).

Kurihara et al., The possible role of endothelin–1 in the pathogenesis of coronary vasospasm, *J. Cardiovas. Pharmacol.* 13:Suppl. 5, S132–S142, (1989).

Lerman et al., Circulating and tissue endothelin immunoreactivity in advanced atheroslcerosis, *New Engl. J. Med.* 325:997–1001, (1991).

Maggi et al., Potent contractile effect of endothelin in isolated guinea–pig airways, *Eur. J. Pharmacol.* 160:179–182 (1989).

Martin et al., Identification and characterization of endothelin binding sites in rat removal papillary and glomerular membranes, *Biochem. Biophys. Res. Commun.* 162:130–137 (1989).

Miyata et al., WS–7338, new endothelian receptor antagonists isolated from Streptomyces sp. No. 7338, *J. Antibiotics* 45(1):74–82 (1992).

Miyata et al., WS009 A and B, new endothelin receptor antagonists isolated from Streptomyces sp. No. 89009, *J. Antibiotics* 45(7):1029–1040 (1992).

Miyauchi et al., Increase of the function of intra–cardiac autonomic nerves in isolated atria of swim–trained rats: study by the intra–cardiac nerve stimulation, *Jpn. J. Pharmacol.* 58:279, (1992).

Morel et al., Increased plasma and pulmonary lymph levels of endothelin during endotoxin shock, *Eur. J. Pharm.* 167:427–428 (1989).

Nakajima et al., Endothelin–binding inhibitors, BE–18257A and BE–18257B II. Structure determination, *J. Antibiotics* 44(12):1348–1356 (1991).

Nakajima et al., Synthesis of endothelin–1 analogues, endothelin–3, and sarafotoxin S6b: structure–activity relationships, *J. Cardiovascular Pharm.* 13(Suppl. 5):S8–S12 (1989).

Nirei et al., An endotheline $et_A$ receptor antagonist, FR139317, Amerliorates cerebral vasospasm in dogs, *Life Sciences* 52:1869–1874, (1993).

Nishikibe et al., Antihypertensive effect of a newly synthesized endothelin antagonists, BQ–123, in a genetic hypertensive model, *Life Sci.* 52:717–724 (1993).

Nishikori et al., Receptor binding affinity and biological activity of C–terminal elongated forms of endothelium–1, *Neurochem. Int.* 18(4):535–539 (1991).

Nogrady et al., 4–pro–drugs and soft drugs, *Medicinal Chemistry A Biochemical Approach*:388–392, (1985).

Nonnast–Daniel et al., Atrial natriuretic peptide and central hemodynamics during correction of renal anemia by recombinant human erythropoietin treatment in regular dialysis treatment patients, *Nephrol Dial Transplant* 4:478 (1989).

Ogawa et al., Molecular cloning of a non–isopeptide–selective human endothelin receptor, *Biochem. and Biophys. Research Comm.* 7, 18(1):248–255 (1991).

Ohashi et al., Asterric acid, a new endothelin binding inhibitor, *J. Antibiotics*, 45(10):1684–1685 (1992).

Palmer et al., Nitric oxide release accounts for the biological activity of endothelium–derived relaxing factor, *Nature* 327:524–526 (1987).

Panek et al., Endothelin and structurally related analogs distinguish between endothelin receptor subtypes, *Biochem. and Biophys. Research Commun.* 183(2):566–571 (1992).

Perkins et al., Proposed solution structure of endothelin, *Int. J. Peptide Protein Res.* 36:128–133 (1990).

Raine et al., Effect of erythropoietin on blood pressure, *Am. J. Kid. Dis.* 18(suppl):76–83 (1991).

Raju et al., Amide bond surrogates: a study in thiophenesulfonamide based endothelin receptor antagonists, *Bioorganic Medicinal Chem. Lett.* 7(7):939–944 (1997).

Raju et al., Search for surrogates: a study of endothelin receptor antagonist structure activity relationships, *Bioorganic Medicinal Chem. Lett.* 7(7): 933–938 (1997).

Raju et al., Thiophenesulfonamides as endothelin receptor antagonists, *Bioorganic Medicinal Chem. Lett.* 6(22):2651–2656 (1996).

Ramachandran et al., Conformation of polypeptides and proteins, *Adv. Prot. Chem.*, 23:283–437 (1968).

Ray et al., Circulating endothelin in acute ischaemic syndromes, *Br. Heart J.* 67:383–386 (1992).

Saeki et al., [Ala$^{1,3,11,15}$] endothelin–1 analogs with ET$_B$ agonistic activity, Biochem. Biophys. Research Commun. 179(1):286–292 (1991).

Saida et al., A novel peptide, vasoactive intestinal contractor, of a new (endothelin) peptide family, J. Biol. Chem. 264(25):14613–14616 (1989).

Saito et al., Application of monoclonal antibodies for endothelin to hypertensive research, Hypertension 15:734–738 (1990).

Sakurai et al., Cloning of a cDNA encoding a non–isopeptide–selective subtype of the endothelin receptor, Nature 348:732–735 (1990).

Samtleben et al., Blood pressure change during treatment with recombinant human erythropoietin, Contrib. Nephrol. 66:114–122 (1988).

Sanjay et al., Does PTCA increase circulating endothelin level in Man?, Circulation 84:(Suppl. 4):726, (1991).

Saudek et al., $^1$H–NMR study of endothelin, sequence–specific assignment of the spectrum and a solution structure, FEBS Letters 257(1):145–148 (1989).

Saudek et al., Solution conformation of endothelin–1 by $^1$H NMR, CD, and molecular modeling, Int. J. Peptide Protein Res. 37:174–179 (1991).

Schafer et al., Treatment of renal anemia with recombinant human erythropoietin, Am. J. Nephrol. 8:352–362 (1989).

Schvartz et al., Bovine cerebellum endothelin receptor: Solubilization and identification, Endocrinology 126(6):3218–3222 (1990).

Shimazaki et al., Piperazine derivatives, Chem. Abstracts 106:4558 (abst. No. 33114a) (1987).

Simonson et al., Endothelin–1 stimulates contraction of rat glomerfular mesangial cells and potentiates β–adrenergic––mediated cyclic adenosine monophosphate accumulation, J. Clin. Invest. 85:790–797, (1990).

Spinella et al., Design and synthesis of a specific endothelin 1 antagonist: Effects on pulmonary vasoconstriction, Proc. Natl. Acad. Sci. USA 88p:7443–7446 (1991).

Spinella et al., A proposed structural model of endothelin, Peptide Research 2(4):286–291 (1989).

Spokes et al., Studies with endothelin–3 and endothelin–1 on rat blood pressure and isolated tissues: Evidence for multiple endothelin receptor subtypes, J. Cardiovasc. Pharmacol. 13(Suppl. 5):S191–S192 (1989).

Stein et al., The Discovery of Sulfonamide Endothelin Antagonists and the Development of the Orally Active ET$_A$–Antagonist 5–(Dimethylamino)–N–(3, 4–dimethyl–5–isoxazolyl)–1–naphthalenesulfonamide, J. Med. Chem. 37(3):329–331 (1994).

Stewart et al., Increased plasma endothelin–1 in pulmonary hypertension: marker or mediator of disease? Annals of Internal Med. 114:464–469, (1991).

Sundal et al., Correction of anemia of chronic renal failure with recombinant human erythropoietin: safety and efficacy of one year's treatment in a European multicenter study of 150 hemodialysis–dependent patients, Nephrol. Dial. Transplant 4:979–987 (1989).

Szelke et al., Novel transition–state analogues inhibitors of renin, In Peptides: Structure and Function, Proceeding of the Eighth American peptide symposium, (Hruby and Rich, Eds.), pp. 579–582, Pierce Chemical Co., Rockford, Illinois (1983).

Tahara et al., Circulating immunoreactive endothelin in patients undergoing percutaneous transluminal coronary angioplasty, Metab. Clin. Exp. 40:1235–1237, (1991).

Takayanagi et al., Multiple subtypes of endothelin receptors in porcine tissues: characterization by ligand binding, affinity labeling and regional distribution, Reg. Pep. 32:23–37 (1991).

Texas Biotechnology Receives First Patent Issued For New Class of Cardiovascular Drugs, Houston, TX, Dec. 6, 1995.

Texas Biotechnology Reports Endothelin A Receptor Antagonist and VCAM/VLA–4 Inhibitor Patents, Houston, TX, May 16, 1996.

Texas Biotechnology Announces Initiation of Phase 1 Clinical Trial For TBC 11251 To Treat Congestive Heart Failure, Houston, TX, Nov. 13, 1996.

Texas Biotechnology Announces Initiation of Phase 1 Clincal Trial For TBC 1269 To Treat Asthma, Houston, TX, Jan. 21, 1997.

Takayanagi et al., Presence of non–selective type of endothelin receptor on vascular endothelium and its linkage to vasodilation, FEBS Letters, 282(1):103–106 (1991).

Tkayama et al., Effects of recombinant human eryghropoietin on blood coagulation, fibrinolysis and endothelium in hemodialysis patients, Blood Purif. 1:53–54 (1991).

Tomita et al., Plasma endothelin levels in patients with acute renal failure, N. Engl. J. Med. 321:1127 (1989).

Vanhoutte et al., Modulation of vascular smooth muscle contraction by the endothelium, Ann. Rev. Physiol. 48:307–320, (1986).

von Geldern et al., A fluorogenic assay for endothelin–converting enzyme, Peptide Research 4(1):32–35 (1991).

Weiner et al., An all atom force field for simulations of proteins and nucleic acids, J. Comput. Chem. 7(2):230–252 (1986).

Weiner et al., A new force field for molecular mechanical simulation of nucleic acids and proteins, J. Am. Chem. Soc. 106(3):765–784 (Eng.) (1984).

Williams et al., Sarafotoxin S6c: An agonist which distinguishes between endothelin receptor subtypes, Biochem. and Biophys. Research Commun. 175(2):556–561 (1991).

Wu et al., Discovery of TBC11251, a potent, long acting, orally acting, orally active endothelin receptor–A selective antagonist, J. Medicinal Chem. 40(11):1690–1697 (1997).

Wu et al., Structure–activity relationships of N–2–aryl–3–(isoxazolysulfamoyl)–2–thiophenecarboxamides as selective endothelin receptor–A antagonists, J. Medicinal Chem. 40(11):1682–1689 (1997).

Yamashita et al., Recombinant human erythropoietin (rHuEPO) induces high plasma endothelin (ET) levels in hemodialysis patients, J. Am. Soc. Nehprol. 1:409 (1990).

Yanagisawa et al., A novel potent vasoconstrictor peptide producer by vascular endothelial cells, Nature 332:411–415 (1988).

Yasuda et al., Circulating immunoreactive endothelin in ischemic heart disease, Amer. Heart J. 119:801–806, (1990).

Zamora et al., Serum endothelin–1 concentrations and cold provocation in primary Raynaud's phenomenon, Lancet 336:1144–1147, (1990).

Fujimoto and Sakai, "Synthesis and Structure of N1–Acylated Sulfiodizole and its homologues", Chem. Pharm. Bull. 14(3):280–284 (1966).

US 6,420,567 B1

N-HETEROARYL ARYL-SUBSTITUTED THIENYL-FURYL-AND PYRROLYL-SULFONAMIDES AND DERIVATIVES THEREOF THAT MODULATE THE ACTIVITY OF ENDOTHELIN

RELATED APPLICATIONS

This application is a continuation-in-part of U.S. application Ser. No. 08/721,183 to Chan et al., filed Sep. 27, 1996, entitled "SULFONAMIDES AND DERIVATIVES THEREOF THAT MODULATE THE ACTIVITY OF ENDOTHELIN, " now U.S. Pat. No. 5,962,490.

This application is also related to International PCT application No. PCT/US96/04759, filed Apr. 4, 1996, entitled "THIENYL-, FURYL- PYRROLYL- AND BIPHE-NYLSULFONAMIDES AND DERIVATIVES THEREOF THAT MODULATE THE ACTIVITY OF ENDOTHELIN"; is also related to of U.S. application Ser. No. 08/477,223, now U.S. Pat. No. 5,594,021, filed Jun. 6, 1995, entitled, "THIENYL-, FURYL- AND PYRROLYL SULFONA-MIDES AND DERIVATIVES THEREOF THAT MODU-LATE THE ACTIVITY OF ENDOTHELIN"; is also related to of U.S. application Ser. No. 08/417,075, filed Apr. 4, 1995, entitled, "THIENYL-, FURYL- AND PYRROLYL SULFONAMIDES AND DERIVATIVES THEREOF THAT MODULATE THE ACTIVITY OF ENDOTHELIN", now abandoned; is also related to of U.S. application Ser. No. 08/247,072, now U.S. Pat. No. 5,571,821, to Chan et al., filed May 20, 1994, entitled "SULFONAMIDES AND DERIVATIVES THEREOF THAT MODULATE THE ACTIVITY OF ENDOTHELIN"; is also related to of U.S. application Ser. No. 08/222,287, now U.S. Pat. No. 5,591,761, to Chan et al., filed Apr. 5, 1994, entitled "THIOPHENYL-, FURYL- AND PYRROLYL-SULFONAMIDES AND DERIVATIVES THEREOF THAT MODULATE THE ACTIVITY OF ENDOTHELIN"; each of these applications is a continuation-in-part of U.S. application Ser. No. 08/142,552, now U.S. Pat. No. 5,514,691, to Chan et al., filed Oct. 21, 1993, entitled "N-(4-HALO-ISOXAZOLYL)-SULFONAMIDES AND DERIVATIVES THEREOF THAT MODULATE THE ACTIVITY OF ENDOTHELIN"; U.S. application Ser. No. 08/142,159, now U.S. Pat. No. 5,464,853, to Chan et al., filed Oct. 21, 1993, entitled "N-(5-ISOXAZOLYL) BIPHENYLSULFONAMIDES, N-(3-ISOXAZOLYL) BIPHENYLSULFONAMIDES AND DERIVATIVES THEREOF THAT MODULATE THE ACTIVITY OF ENDOTHELIN"; and U.S. Appellation Ser. No. 08/142,631 to CHAIN et al., filed Oct. 21, 1993, "N-(5-ISOXAZOLYL)-BENZENESULFONAMIDES, N-(3-ISOXAZOLYL)-BENZENESULFONAMIDES AND DERIVATIVES THEREOF THAT MODULATE THE ACTIVITY OF ENDOTHELIN", now abandoned.

U.S. application Ser. No. 08/721,183 is a continuation-in-part of International PCT application No. PCT/US96/04759; is also a continuation-in-part of U.S. application Ser. No. 08/477,223, now U.S. Pat. No. 5,594,021; is also a continuation-in-part of U.S. application Ser. No. 08/417,075, now abandoned; is also a continuation-in-part of U.S. application Ser. No. 08/247,072, now U.S. Pat. No. 5,571,812; is also a continuation-in-part of U.S. application Ser. No. 08/222,287, now U.S. Pat. No. 5,591,761; each of these applications is a continuation-in-part of U.S. application Ser. No. 08/142,552, now U.S. Pat. No. 5,514,691; U.S. application Ser. No. 08/142,159, now U.S. Pat. No. 5,464,853; and U.S. application Ser. No. 08/142,631, now abandoned.

International PCT application No. PCT/US96/04759 is a continuation-in-part of U.S. application Ser. No. 08/477,223, now U.S. Pat. No. 5,594,021; is also a continuation-in-part of U.S. application Ser. No. 08/417,075, now abandoned; and is also a continuation-in-part of U.S. application Ser. No. 08/416,199, to Chan, et al., filed Apr. 4, 1995, entitled, "BENZENESULFONAMIDES AND THE USE THEREOF TO MODULATE THE ACTIVITY OF ENDOT-HELIN". U.S. application Ser. No. 08/477,223 is a continuation-in-part of U.S. application Ser. No. 08/417, 075, now abandoned. Each of U.S. application Ser. Nos. 08/477,223, 08/417,075 and 08/416,199 is in turn a continuation-in-part of U.S. application Ser. No. 08/247, 072, now U.S. Pat. No. 5,571,821; U.S. application Ser. No. 08/222,287, now U.S. Pat. No. 5,591,761; U.S. application Ser. No. 08/142,552, now U.S. Pat. No. 5,514,691; U.S. application Ser. No. 08/142,159, now U.S. Pat. No. 5,464, 853; U.S. application Ser. No. 08/142,631, now abandoned; U.S. application Ser. No. 08/100,565 to Chan et al., filed Jul. 30, 1993, entitled "N-(5-ISOXAZOLYL)-SULFONAMIDES AND DERIVATIVES THEREOF THAT MODULATE THE ACTIVITY OF ENDOTHELIN", now abandoned; U.S. application Ser. No. 08/100,125, to Chan et al., filed Jul. 30, 1993, entitled "N-(3-ISOXAZOLYL)-SULFONAMIDES AND DERIVATIVES THEREOF THAT MODULATE THE ACTIVITY OF ENDOTHELIN", now abandoned; and U.S. application Ser. No. 08/065,202, to Chan, filed May 20, 1993, entitled "SULFONAMIDES AND DERIVATIVES THEREOF THAT MODULATE THE ACTIVITY OF ENDOTHELIN", now abandoned.

U.S. application Ser. No. 08/417,075 is a continuation-in-part of U.S. application Ser. No. 08/247,072, now U.S. Pat. No. 5,571,821, which is a continuation-in -part of U.S. application Ser. No. 08/222,287, now U.S. Pat. No. 5,591, 761. U.S. application Ser. Nos. 08/416,199, 08/247,072 and 08/222,287 are each a continuation-in-part of the following applications: U.S. application Ser. No. 08/142,552, now U.S. Pat. No. 5,514,691; U.S. application Ser. No. 08/142, 159, now U.S. Pat. No. 5,464,853; U.S. application Ser. No. 08/142,631 to Chan et al., filed Oct. 21, 1993, "N-(5-ISOXAZOLYL)-BENZENESULFONAMIDES, N-(3-ISOXAZOLYL)-BENZENESULFONAMIDES AND DERIVATIVES THEREOF THAT MODULATE THE ACTIVITY OF ENDOTHELIN"; U.S. application Ser. No. 08/100,565; U.S. application Ser. No. 08/100,125; and U.S. application Ser. No. 08/065,202.

U.S. application Ser. No. 08/416,199 is a continuation-in-part of U.S. application Ser. No. No. 08/247,072, now U.S. Pat. No. 5,571,821; U.S. application Ser. No. 08/222, 287, now U.S. Pat. No. 5,591,761; U.S. application Ser. No. 08/142,159, now U.S. Pat. No. 5,464,853; U.S. application Ser. No. 08/142,552, now U.S. Pat. No. 5,514,691; U.S. application Ser. No. 08/100,565, now abandoned; U.S. application Ser. No. 08/100,125, now abandoned; and U.S. application Ser. No. 08/065,202, now abandoned.

U.S. application Ser. Nos. 08/142,159, 08/142,552, 08/142,631 are continuation-in-part applications of U.S. application Ser. Nos. 08/100,565, 08/100,125 and 08/065, 202, all now abandoned; and U.S. application Ser. Nos. 08/100,565 and 08/100,125 are continuation-in-part applications of U.S. application Ser. No. 08/065,202, now abandoned.

The subject matter of International PCT application No. PCT/US96/0475 and each of U.S. application Ser. Nos. 08/721,183, 08/477,223, 08/417,075, 08/416,199, 08/247, 072, 08/222,287, 08/142,159, 08/142,552, 08/142,631, 08/100,565, 08/100,125 and 08/065,202 is incorporated herein in its entirety.

FIELD OF THE INVENTION

The present invention relates to compounds that modulate the activity of the endothelin family of peptides. In particular, the invention relates to the use of sulfonamides and sulfonamide salts and pro-drugs as endothelin agonists and antagonists.

BACKGROUND OF THE INVENTION

The vascular endothelium releases a variety of vasoactive substances, including the endothelium-derived vasoconstrictor peptide, endothelin (ET) (see, e.g., Vanhoutte et al. (1986) *Annual Rev. Physiol.* 48: 307–320; Furchgott and Zawadski (1980) *Nature* 288: 373–376). Endothelin, which was originally identified in the culture supernatant of porcine aortic endothelial cells (see, Yanagisawa et al. (1988) *Nature* 332: 411–415), is a potent twenty-one amino acid peptide vasoconstrictor. It is the most potent vasopressor known and is produced by numerous cell types, including the cells of the endothelium, trachea, kidney and brain. Endothelin is synthesized as a two hundred and three amino acid precursor preproendothelin that contains a signal sequence which is cleaved by an endogenous protease to produce a thirty-eight (human) or thirty-nine (porcine) amino acid peptide. This intermediate, referred to as big endothelin, is processed in vivo to the mature biologically active form by a putative endothelin-converting enzyme (ECE) that appears to be a metal-dependent neutral protease (see, e.g., Kashiwabara et al. (1989) *FEBS Lttrs.* 247: 337–340). Cleavage is required for induction of physiological responses (see, e.g., von Geldern et al. (1991) *Peptide Res.* 4: 32–35). In porcine aortic endothelial cells, the thirty-nine amino acid intermediate, big endothelin, is hydrolyzed at the $Trp^{21}$-$Val^{22}$ bond to generate endothelin-1 and a C-terminal fragment. A similar cleavage occurs in human cells from a thirty-eight amino acid intermediate. Three distinct endothelin isopeptides, endothelin-1, endothelin-2 and endothelin-3, that exhibit potent vasoconstrictor activity have been identified.

The family of three isopeptides endothelin-1, endothelin-2 and endothelin-3 are encoded by a family of three genes (see, Inoue et al. (1989) *Proc. Natl. Acad. Sci. USA* 86: 2863–2867; see, also Saida et al. (1989) *J. Biol. Chem.* 264: 14613–14616). The nucleotide sequences of the three human genes are highly conserved within the region encoding the mature 21 amino acid peptides and the C-terminal portions of the peptides are identical. Endothelin-2 is ($Trp^6$,$Leu^7$) endothelin-1 and endothelin-3 is ($Thr^2$,$Phe^4$, $Thr^5$, $Tyr^6$,$Lys^7$, $Tyr^{14}$) endothelin-1. These peptides are, thus, highly conserved at the C-terminal ends. Release of endothelins from cultured endothelial cells is modulated by a variety of chemical and physical stimuli and appears to be regulated at the level of transcription and/or translation. Expression of the gene encoding endothelin-1 is increased by chemical stimuli, including adrenaline, thrombin and $Ca^{2+}$ ionophore. The production and release of endothelin from the endothelium is stimulated by angiotensin II, vasopressin, endotoxin, cyclosporine and other factors (see, Brooks et al. (1991) *Eur. J. Pharm.* 194:115–117), and is inhibited by nitric oxide. Endothelial cells appear to secrete short-lived endothelium-derived relaxing factors (EDRF), including nitric oxide or a related substance (Palmer et al. (1987) *Nature* 327: 524–526), when stimulated by vasoactive agents, such as acetylcholine and bradykinin. Endothelin-induced vasoconstriction is also attenuated by atrial natriuretic peptide (ANP).

The endothelin peptides exhibit numerous biological activities in vitro and in vivo. Endothelin provokes a strong and sustained vasoconstriction in vivo in rats and in isolated vascular smooth muscle preparations; it also provokes the release of eicosanoids and endothelium-derived relaxing factor (EDRF) from perfused vascular beds. Intravenous administration of endothelin-1 and in vitro addition to vascular and other smooth muscle tissues produce long-lasting pressor effects and contraction, respectively (see, e.g., Bolger et al. (1991) *Can. J. Physiol. Pharmacol.* 69: 406–413). In isolated vascular strips, for example, endothelin-1 is a potent ($EC_{50}$=$4\times10^{-10}$ M), slow acting, but persistent, contractile agent. In vivo, a single dose elevates blood pressure in about twenty to thirty minutes. Endothelin-induced vasoconstriction is not affected by antagonists to known neurotransmitters or hormonal factors, but is abolished by calcium channel antagonists. The effect of calcium channel antagonists, however, is most likely the result of inhibition of calcium influx, since calcium influx appears to be required for the long-lasting contractile response to endothelin.

Endothelin also mediates renin release, stimulates ANP release and induces a positive inotropic action in guinea pig atria. In the lung, endothelin-1 acts as a potent bronchoconstrictor (Maggi et al. (1989) *Eur. J. Pharmacol.* 160: 179–182). Endothelin increases renal vascular resistance, decreases renal blood flow, and decreases glomerular filtrate rate. It is a potent mitogen for glomerular mesangial cells and invokes the phosphoinoside cascade in such cells (Simonson et al. (1990) *J. Clin. Invest.* 85: 790–797).

There are specific high affinity binding sites (dissociation constants in the range of $2$–$6\times10^{-10}$ M) for the endothelins in the vascular system and in other tissues, including the intestine, heart, lungs, kidneys, spleen, adrenal glands and brain. Binding is not inhibited by catecholamines, vasoactive peptides, neurotoxins or calcium channel antagonists. Endothelin binds and interacts with receptor sites that are distinct from other autonomic receptors and voltage dependent calcium channels. Competitive binding studies indicate that there are multiple classes of receptors with different affinities for the endothelin isopeptides. The sarafotoxins, a group of peptide toxins from the venom of the snake *Atractaspis eingadensis* that cause severe coronary vasospasm in snake bite victims, have structural and functional homology to endothelin-1 and bind competitively to the same cardiac membrane receptors (Kloog et al. (1989) *Trends Pharmacol. Sci.* 10: 212–214).

Two distinct endothelin receptors, designated $ET_A$ and $ET_B$, have been identified and DNA clones encoding each receptor have been isolated (Arai et al. (1990) *Nature* 348: 730–732; Sakurai et al. (1990) *Nature* 348: 732–735). Based on the amino acid sequences of the proteins encoded by the cloned DNA, it appears that each receptor contains seven membrane spanning domains and exhibits structural similarity to G-protein-coupled membrane proteins. Messenger RNA encoding both receptors has been detected in a variety of tissues, including heart, lung, kidney and brain. The distribution of receptor subtypes is tissue specific (Martin et al. (1989) *Biochem. Biophys. Res. Commun.* 162: 130–137). $ET_A$ receptors appear to be selective for endothelin-1 and are predominant in cardiovascular tissues. $ET_B$ receptors are predominant in noncardiovascular tissues, including the central nervous system and kidney, and interact with the three endothelin isopeptides (Sakurai et al. (1990) *Nature* 348: 732–734). In addition, $ET_A$ receptors occur on vascular smooth muscle, are linked to vasoconstriction and have been associated with cardiovascular, renal and central nervous system diseases; whereas $ET_B$ receptors are located on the vascular endothelium, linked to vasodilation (Takayanagi et al. (1991) *FEBS Lttrs.* 282: 103–106) and have been associated with bronchoconstrictive disorders.

By virtue of the distribution of receptor types and the differential affinity of each isopeptide for each receptor type, the activity of the endothelin isopeptides varies in different tissues. For example, endothelin-1 inhibits $^{125}$I-labelled endothelin-1 binding in cardiovascular tissues forty to seven hundred times more potently than endothelin-3. $^{125}$I-labelled endothelin-1 binding in non-cardiovascular tissues, such as kidney, adrenal gland, and cerebellum, is inhibited to the same extent by endothelin-1 and endothelin-3, which indicates that $ET_A$ receptors predominate in cardiovascular tissues and $ET_B$ receptors predominate in non-cardiovascular tissues.

Endothelin plasma levels are elevated in certain disease states (see, e.g., International PCT Application WO 94/27979, and U.S. Pat. No. 5,382,569, which disclosures are herein incorporated in their entirety by reference). Endothelin-1 plasma levels in healthy individuals, as measured by radioimmunoassay (RIA), are about 0.26–5 pg/ml. Blood levels of endothelin-1 and its precursor, big endothelin, are elevated in shock, myocardial infarction, vasospastic angina, kidney failure and a variety of connective tissue disorders. In patients undergoing hemodialysis or kidney transplantation or suffering from cardiogenic shock, myocardial infarction or pulmonary hypertension levels as high as 35 pg/ml have been observed (see, Stewart et al. (1991) *Annals Internal Med.* 114: 464–469). Because endothelin is likely to be a local, rather than a systemic, regulating factor, it is probable that the levels of endothelin at the endothelium/smooth muscle interface are much higher than circulating levels.

Elevated levels of endothelin have also been measured in patients suffering from ischemic heart disease (Yasuda et al. (1990) *Amer. Heart J.* 119:801–806, Ray et al. (1992) *Br. Heart J.* 67:383–386). Circulating and tissue endothelin immunoreactivity is increased more than twofold in patients with advanced atherosclerosis (Lerman et al. (1991) *New Engl. J. Med.* 325:997–1001). Increased endothelin immunoreactivity has also been associated with Buerger's disease (Kanno et al. (1990) *J. Amer. Med. Assoc.* 264:2868) and Raynaud's phenomenon (Zamora et al. (1990) Lancet 336 1144–1147). Increased circulating endothelin levels were observed in patients who underwent percutaneous transluminal coronary angioplasty (PTCA) (Tahara et al. (1991) *Metab. Clin. Exp.* 40:1235–1237; Sanjay et al. (1991) *Circulation* 84(*Suppl.* 4):726), and in individuals (Miyauchi et al. (1992) *Jpn. J. Pharmacol.*58:279P; Stewart et al. (1991) *Ann.Internal Medicine* 114:464–469) with pulmonary hypertension. Thus, there is clinical human data supporting the correlation between increased endothelin levels and numerous disease states.

Endothelin Agonists and Antagonists

Because endothelin is associated with certain disease states and is implicated in numerous physiological effects, compounds that can interfere with or potentiate endothelin-associated activities, such as endothelin-receptor interaction and vasoconstrictor activity, are of interest. Compounds that exhibit endothelin antagonistic activity have been identified. For example, a fermentation product of *Streptomyces misakiensis,* designated BE-18257B, has been identified as an $ET_A$ receptor antagonist. BE-18257B is a cyclic pentapeptide, cyclo(D-Glu-L-Ala-allo-D-Ile-L-Leu-D-Trp), which inhibits $^{125}$I-labelled endothelin-1 binding in cardiovascular tissues in a concentration-dependent manner ($IC_{50}$ 1.4 $\mu$M in aortic smooth muscle, 0.8 $\mu$M in ventricle membranes and 0.5 $\mu$M in cultured aortic smooth muscle cells), but fails to inhibit binding to receptors in tissues in which $ET_B$ receptors predominate at concentrations up to 100 $\mu$M. Cyclic pentapeptides related to BE-1 8257B, such as cyclo(D-Asp-Pro-D-Val-Leu-D-Trp) (BQ-123), have been synthesized and shown to exhibit activity as $ET_A$ receptor antagonists (see, U.S. Pat. No. 5,114,918 to Ishikawa et al.; see, also, EP A1 0 436 189 to BANYU PHARMACEUTICAL CO., LTD (Oct. 7, 1991)). Studies that measure the inhibition by these cyclic peptides of endothelin-1 binding to endothelin-specific receptors indicate that these cyclic peptides bind preferentially to $ET_A$ receptors. Other peptide and non-peptidic $ET_A$ antagonists have been identified (see, e.g., U.S. Pat. Nos. 5,352,800, 5,334,598, 5,352,659, 5,248,807, 5,240,910, 5,198,548, 5,187,195, 5,082,838). These include other cyclic pentapeptides, acyltripeptides, hexapeptide analogs, certain anthraquinone derivatives, indanecarboxylic acids, certain N-pyriminylbenzenesulfonamides, certain benzenesulfonamides, and certain naphthalenesulfonamides (Nakajima et al. (1991) *J. Antibiot.* 44:1348–1356; Miyata et al. (1992) *J. Antibiot.* 45:74–8; Ishikawa et al. (1992) *J.Med. Chem.* 35:2139–2142; U.S. Pat. No. 5,114,918 to Ishikawa et al.; EP A1 0 569 193; EP A1 0 558 258; EP A1 0 436 189 to BANYU PHARMACEUTICAL CO., LTD (Oct. 7, 1991); Canadian Patent Application 2,067,288; Canadian Patent Application 2,071,193; U.S. Pat. Nos. 5,208,243; 5,270,313; 5,612,359, 5,514,696, 5,378,715; Cody et al. (1993) *Med. Chem. Res.* 3:154–162; Miyata et al. (1992) *J. Antibiot* 45:1041–1046; Miyata et al. (1992) *J. Antibiot* 45:1029–1040, Fujimoto et al. (1992) *FEBS Lett.* 305:41–44; Oshashi et al. (1002) *J. Antibiot* 45:1684–1685; EP A1 0 496 452; Clozel et al. (1993) *Nature* 365:759–761; International Patent Application WO93/08799; Nishikibe et al. (1993) *Life Sci.* 52:717–724; and Benigni et al. (1993) *Kidney Int.* 44:440–444). Numerous sulfonamides that are endothelin peptide antagonists are also described in U.S. Pat. Nos. 5,464,853, 5,594,021, 5,591,761, 5,571,821, 5,514,691, 5,464,853, International PCT application No.96/31492 and International PCT application No. WO 97/27979.

In general, the identified compounds have activities in in vitro assays as $ET_A$ antagonists at concentrations on the order of about 50–100 $\mu$M or less. A number of such compounds have also been shown to possess activity in in vivo animal models.

Endothelin Antagonists and Agonists as Therapeutic Agents

It has been recognized that compounds that exhibit activity at $IC_{50}$ or $EC_{50}$ concentrations on the order of $10^{-4}$ or lower in standard in vitro assays that assess endothelin antagonist or agonist activity have pharmacological utility (see, e.g., U.S. Pat. Nos. 5,352,800, 5,334,598, 5,352,659, 5,248,807, 5,240,910, 5,198,548, 5,187,195 and 5,082,838). By virtue of this activity, such compounds are considered to be useful for the treatment of hypertension such as peripheral circulatory failure, heart disease such as angina pectoris, cardiomyopathy, arteriosclerosis, myocardial infarction, pulmonary hypertension, vasospasm, vascular restenosis, Raynaud's disease, cerebral stroke such as cerebral arterial spasm, cerebral ischemia, late phase cerebral spasm after subarachnoid hemorrhage, asthma, bronchoconstriction, renal failure, particularly post-ischemic renal failure, cyclosporine nephrotoxicity such as acute renal failure, colitis, as well as other inflammatory diseases, endotoxic shock caused by or associated with endothelin, and other diseases in which endothelin has been implicated.

In view of the numerous physiological effects of endothelin and its association with certain diseases, endothelin is believed to play a critical role in these pathophysiological conditions (see, e.g., Saito et al. (1990) *Hypertension* 15: 734–738; Tomita et al. (1989) *N. Engl. J. Med.* 321: 1127; Kurihara et al. (1989) *J. Cardiovasc. Pharmacol.* 13(*Suppl.* 5): S13–S17; Doherty (1992) *J. Med. Chem.* 35: 1493–1508; Morel et al. (1989) *Eur. J. Pharmacol.* 167: 427–428). More detailed knowledge of the function and structure of the endothelin peptide family should provide insight in the progression and treatment of such conditions.

To aid in gaining further understanding of and to develop treatments for endothelin-mediated or related disorders, there is a need to identify compounds that modulate or alter endothelin activity. Identification of compounds that modulate endothelin activity, such as those that act as specific antagonists or agonists, may not only aid in elucidating the function of endothelin, but may yield in therapeutically useful compounds. In particular, compounds that specifically interfere with the interaction of endothelin peptides with the $ET_A$ or $ET_B$ receptors should be useful in identifying essential characteristics of endothelin peptides, should aid in the design of therapeutic agents, and may be useful as disease specific therapeutic agents. As noted above, many of the compounds, particularly the sulfonamide compounds, are potent endothelin antagonists, and, thus, are ideal clinical candidates. For clinical use, potent compounds optimized for in vivo activity as well as stable formulations and suitable formulations for various routes of administration are needed.

Therefore, it is an object herein to provide compounds that have the ability to modulate the biological activity of one or more of the endothelin isopeptides and that exhibit in vivo. It is another object to provide compounds that have use as specific endothelin antagonists in vivo. It is also an object to use compounds that specifically interact with or inhibit the interaction of endothelin peptides with $ET_A$ receptors. It is also an object herein to provide formulations of such compounds useful for treatment of endothelin-mediated diseases. These compounds should be useful as therapeutic agents for the treatment of endothelin-mediated diseases and disorders.

SUMMARY OF THE INVENTION

Sulfonamides, formulations of sulfonamides and methods for modulating the interaction of an endothelin peptide with $ET_A$ and/or $ET_B$ receptors are provided. In particular, sulfonamides, formulations of sulfonamides and methods for inhibiting the binding of an endothelin peptide to $ET_A$ or $ET_B$ receptors are provided. The sulfonamides are substituted or unsubstituted thienyl, furanyl and pyrrolyl sulfonamides.

Particularly preferred sulfonamides are N-isoxazolyl thiophene sulfonamides where the thiophene is substituted with an aryl group, preferably a phenyl group, which has only one or two hydrogen substituents. These compounds appear to exhibit superior potency, efficacy, bioavailability, in vivo half-life and/or stability compared with compounds where the aryl group has more than two hydrogen substituents, while avoiding toxicological effects associated with hydrophobicity. In addition, these compounds appear to exhibit good profiles in standard in vitro toxicity tests.

It has been found that for in vivo administration, it is desirable to achieve the proper degree of hydrophilicity, which reduces potential hemolytic properties of the compounds. It has been found herein, for example, that this is achieved if the aryl group is tetra-, penta- or hexasubstituted, preferably pentasubstituted. If the aryl group is tetrasubstituted, it will preferably be substituted at the 2, 4 and 6 positions, and one of these substituents will be a polar group, such as hydroxyl, acetoxy, carboxyl and carboxamide. Such substitution enhances the endothelin antagonist activity and the hydrophilicity of the compounds. If the aryl group is substituted at the 2, 4 and 6 positions with nonpolar groups, such as alkyl groups, more specifically methyl groups, then the aryl group will preferably be penta- or hexasubstituted. In pentasubstituted aryl groups, the fifth substituent will be at the 3 position and will preferably be a polar group, such as hydroxyl, acetoxy, carboxyl and carboxamide. Such substitution is preferred to achieve highest levels of activity for therapeutic use.

Such substitution provides compounds with good bioavailability, long in vivo half-life, and/or good in vivo efficacy. In view of the disclosure herein, other such optimal substituent patterns and substituents can be determined empirically using suitable animal models.

The sulfonamides, including pharmaceutically acceptable salts, acids, esters and other derivatives thereof, have the formula: (A):

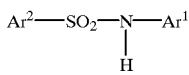

in which $Ar^1$ is a substituted or unsubstituted aryl or heteroaryl group with one or more substituents, including an alkyl group, an aryl group, a substituted aryl group, a nitro group, an amino group or a halide or is an alkyl group. In particular, $Ar^1$ is alkyl or is a five or six membered substituted or unsubstituted aromatic or heteroaromatic ring, particularly 3- or 5-isoxazolyl and pyridazinyl, and also including thiazolyl, including 2-thiazolyl, pyrimidinyl, including 2-pyrimidinyl, or substituted benzene groups, including aryloxy substituted benzene groups or is a bicyclic or tricyclic carbon or heterocyclic ring. Preferred formulations of these compounds contain sodium salts of the compounds.

Among the compounds of interest herein are those in which $Ar^2$ has the formula:

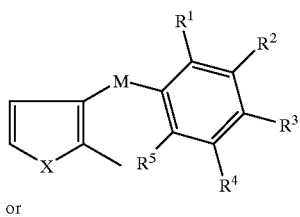

or

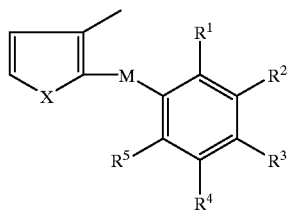

in which
M is $(CH_2)_mC(O)(CH_2)_r$, $(CH_2)_mC(O)NH(CH_2)_r$, $(CH_2)_m(CH=CH)(CH_2)_r$, $(CH_2)_mC(O)(CH_2)_sNH$ $(CH_2)_r$, $(CH_2)_m(CH=CH)(CH_2)_r$, $C=N(OH)(CH_2)_r$, $(CH_2)_mC(O)(CH=CH)_sNH(CH_2)_r$, $CH(OH)(CH_2)_r$, $CH(CH_3)C(O)(CH_2)_r$, $CH(CH_3)C(O)(CH_2)_m(CH=C)$ $(CH_2)_r$, $(CH_2)_rO$, $(CH_2)S(O)_n$ wherein n is 0–2, $C(O)$ O, in which m,s and r are each independently 0 to 6, preferably 0 to 3, more preferably M is $(CH_2)_mC(O)(CH_2)_r$, $(CH_2)_mC(O)NH(CH_2)_r$, $(CH_2)_m(CH=CH)(CH_2)_r$, $(CH_2)_mC(O)(CH_2)_sNH(CH_2)_r$, $(CH_2)_m(CH=CH)(CH_2)_r$, $C=N(OH)(CH_2)_r$, $CH(OH)(CH_2)_r$, $(CH_2)_r$, $(CH_2)_rO$, $(CH_2)S(O)_n$, $C(O)O$;

$R^1$, $R^2$, $R^3$, $R^4$ and $R^5$ are each independently selected from (i) or (ii) as follows:

(i) $R^1$, $R^2$, $R^3$, $R^4$ and $R^5$ are each independently selected from among H, OH, $NHR^{38}$, $CONR^{38}R^{39}$, $NO_2$, cyano, halide, pseudohalide, alkyl, alkenyl, alkynyl, aryl, arylalkyl, heteroaryl, alkoxy, alkylamino, alkylthio, haloalkyl, alkylsulfinyl, alkylsulfonyl, alkoxycarbonyl, alkylcarbonyl, alkenylthio, alkenylamino, alkenyloxy, alkenyl sulfinyl, alkenylsulfonyl, alkoxycarbonyl, arylaminocarbonyl, alkylaminocarbonyl, aminocarbonyl, (alkyl-aminocarbonyl)alkyl, acetoxy, hydroxyl, carboxyl, carboxyalkyl, carboxyalkenyl, alkylsulfonylaminoalkyl, cyanoalkyl, acetyl, acetoxyalkyl, hydroxyalkyl, alkyoxyalkyl, hydroxyalkyl, (acetoxy)alkoxy, (hydroxy)alkoxy, formyl, sulfonyl chlorides, amino acids, hexoses, O-glycosides, riboses, lower alkyl, CN, $-(CH_2)_xC(O)(CH_2)_x$, $-(CH_2)_x$, $(CH_2)_xN$-lower alkyl, $-(CH_2)_xC(O)NH_2$, a D-, L- or racemic amino acid, a primary or secondary amide, O-glycoside, a hexose or ribose, $-S(O)_2NH_2$, hydroxy, alkoxy, alkoxycarbonyl, acetoxyalkyl, $-(CH_2)_xCOOH$; $-(CH_2)_xCOOH-$, $CO_2$-lower alkyl, CN, heteroaryl, $-COC(O)(CH_2)_xCH_3$, $-(CH_2)_xN(CH_3)_2$, a sulfonyl chloride, $S(O)_2NHR^{50}$, alkylaryl, alkylheteroaryl, $C(O)NHR^{50}$, $-(CH_2)_xOH$, $-C(O)N(H)N(H)M$, or;

(ii) at least two of $R^1$, $R^2$, $R^3$, $R^4$ and $R^5$, which substitute adjacent carbons on the ring, together form alkylenedioxy, alkylenethioxyoxy or alkylenedithioxy (i.e. $-O-(CH_2)_n-O-$, $-S-(CH_2)_n-O-$, $-S-(CH_2)_n-S-$, where n is 1 to 4, preferably 1 or 2,) which is unsubstituted or substituted by replacing one or more hydrogens with halide, lower alkyl, lower alkoxy or halo lower alkyl, and the others of $R^1$, $R^2$, $R^3$, $R^4$ and $R^5$ are selected as in (i).

In preferred embodiments herein, at least four of $R^1$, $R^2$, $R^3$, $R^4$ and $R^5$ are not hydrogen, unless:

(a) $R^1$ and $R^3$ are alkyl and $R^5$ is $R^{20}$, which is selected from the group consisting of aryl, heteroaryl, heterocycle, OH, CN, $C(O)R^{16}$, $CO_2R^{16}$, SH, $S(O)_nR^{16}$ in which n is 0–2, a D, L or racemic amino acid, a ribose or hexose, an O-glycoside, a sulfonyl chloride, $-(CH_2)_xOH$, NHOH, $NR^{12}R^{16}$, $NO_2$, $N_3$, $OR^{16}$, $R^{12}NCOR^{16}$ and $CONR^{12}R^{16}$, then $R^2$ and $R^4$ may be H; or (b) when M is $-CONHC(R^{12})(R^{16})-$, then $R^1$, $R^2$, $R^3$, $R^4$ and $R^5$ may all be H;

(c) when M is $-COCHR^6-$, $Ar^1$ is not an isoxazolyl, $R^1$ is alkyl, and $R^3$ and $R^4$ form alkylenedioxy, then $R^2$ and $R^5$ may be H;^C^C $R^{38}$ and $R^{39}$ are each independently selected from hydrogen, alkyl, alkenyl, alkynyl, aryl, haloalkyl alkylaryl, heterocycle, arylalkyl, arylalkoxy, alkoxy, aryloxy, cycloalkyl, cycloalkenyl and cycloalkynyl, and is preferably hydrogen, lower alkyl, lower alkoxy and lower haloalkyl;

X is S, O or $NR^{11}$, where $R^{11}$ contains up to about 30 carbon atoms, preferably 1 to 10, more preferably 1 to 6 and is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{15}$ and $S(O)_nR^{15}$ in which n is 0–2; $R^{15}$ is hydrogen, alkyl, alkenyl, alkynyl, aryl, alkylaryl, heterocycle, aralkyl, aralkoxy, cycloalkyl, cycloalkenyl, cycloalkynyl; $R^{11}$ and $R^{15}$ are unsubstituted or are substituted with one or more substituents each selected independently from Z, which as defined herein includes hydrogen, halide, pseudohalide, alkyl, alkoxy, alkenyl, alkynyl, aryl, amino acids, primary and secondary amides, O-glycosides, hexoses, riboses, alkylaryl, alkylheteroaryl, heterocycle, aralkyl, aralkoxy, cycloalkyl, cycloalkenyl, cycloalkynyl, OH, CN, $C(O)R^{16}$, $OC(O)R^{16}$, $CO_2R^{16}$, $OCO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl, cycloalkynyl, chloride, $NHR^{50}$, alkylaryl, alkylheteroaryl, or $-(CH_2)_xOH$; $R^{50}$ is a substituent such as hydrogen, lower alkyl, or lower alkoxy; $R^{12}$, which is selected independently from $R^{11}$ and Z, is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; $R^{17}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$ and $R^{16}$ may together form alkylene; each of $R^{11}$, $R^{12}$, $R^{15}$ and $R^{16}$ may be further substituted with the any of the appropriate groups of those set forth for Z.

In all compounds, at least one of $R^1$ and $R^5$ is other than hydrogen.

X is preferably S, and M is preferably selected from among:

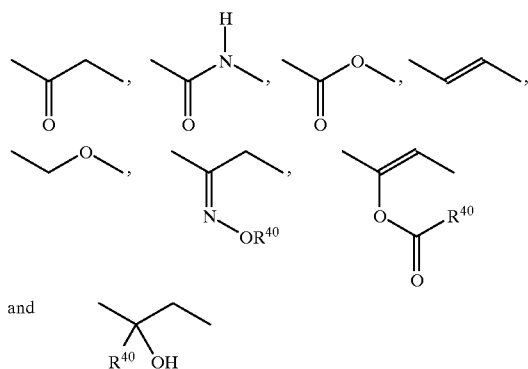

in which $R^{40}$ is preferably hydrogen, alkyl, alkoxy, alkoxyalkyl, haloalkyl, and more preferably loweralkyl, loweralkoxy, or halo loweralkyl, and is more preferably hydrogen or loweralkyl, particularly methyl or ethyl, and is most preferably hydrogen.

In more preferred compounds, M is $C(O)CH_2$, $C(O)NH$, $-CH=CH-$, $CH_2CH_2C(O)(CH)_2$, $CH_2CHC(O)CH_2$, and M is most preferably selected from among:

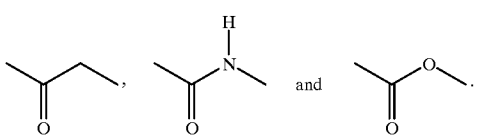

$Ar^2$ most preferably has formula:

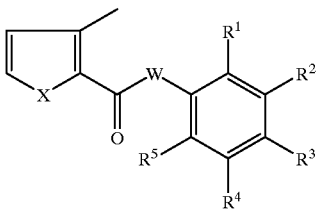

in which W is most preferably $CH_2$ or NH.

In all embodiments, the selected compounds preferably are not selected from the group consisting of:

N-(4-chloro-3-methyl-5-isoxazolyl)-2-(3-cyanomethyl-2,4,6-trimethylphenylaminocarbonyl)thiophene-3-sulfonamide;
N-(4-chloro-3-methyl-5-isoxazolyl)-2-(3-hydroxymethyl-2,4,6-trimethylphenylaminocarbonyl)thiophene-3-sulfonamide;
N-(4-chloro-3-methyl-5-isoxazolyl)-2-(3-cyano-2,4,6-trimethylphenylaminocarbonyl)thiophene-3-sulfonamide;
N-(4-chloro-3-methyl-5-isoxazolyl)-2-(3-methoxycarbonyl-2,4,6-trimethylphenylaminocarbonyl)thiophene-3-sulfonamide;
N-(4-chloro-3-methyl-5-isoxazolyl)-2-(3-carboxyl-2,4,6-trimethylphenylaminocarbonyl)thiophene-3-sulfonamide;
N-(4-chloro-3-methyl-5-isoxazolyl)-2-(3-methanesulfonyl-2,4,6-trimethylphenylaminocarbonyl)thiophene-3-sulfonamide;
N-(4-chloro-3-methyl-5-isoxazolyl)-2-(3-(2-hydroxyethyl)-2,4,6-trimethylphenylaminocarbonyl)thiophene-3-sulfonamide;
N-(4-chloro-3-methyl-5-isoxazolyl)-2-(3-cyanomethyl-2,4,6-trimethylphenylacetyl)thiophene-3-sulfonamide;
N-(4-chloro-3-methyl-5-isoxazolyl)-2-(3-hydroxymethyl-2,4,6-trimethylphenylacetyl)thiophene-3-sulfonamide;
N-(4-chloro-3-methyl-5-isoxazolyl)-2-(3-cyano-2,4,6-trimethylphenylacetyl)thiophene-3-sulfonamide;
N-(4-chloro-3-methyl-5-isoxazolyl)-2-(3-methoxycarbonyl-2,4,6-trimethylphenylacetyl)thiophene-3-sulfonamide;
N-(4-chloro-3-methyl-5-isoxazolyl)-2-(3-carboxyl-2,4,6-trimethylphenylacetyl)thiophene-3-sulfonamide;
N-(4-chloro-3-methyl-5-isoxazolyl)-2-(3-methanesulfonyl-2,4,6-trimethylphenylacetyl)thiophene-3-sulfonamide;
N-(4-chloro-3-methyl-5-isoxazolyl)-2-(3-(2-hydroxyethyl)-2,4,6-trimethylphenylacetyl)thiophene-3-sulfonamide;
N-(4-chloro-3-methyl-5-isoxazolyl)-2-(6-methyl-2,3,4-trimethoxyphenylaminocarbonyl)thiophene-3-sulfonamide;
N-(4-chloro-3-methyl-5-isoxazolyl)-2-(6-acetyl-2,3,4-trimethoxyphenylaminocarbonyl)thiophene-3-sulfonamide;
N-(4-chloro-3-methyl-5-isoxazolyl)-2-(6-methoxycarbonyl-2,3,4-trimethoxyphenylaminocarbonyl)thiophene-3-sulfonamide;
N-(4-chloro-3-methyl-5-isoxazolyl)-2-(6-carboxyl-2,3,4-trimethoxyphenylaminocarbonyl)thiophene-3-sulfonamide;
N-(4-chloro-3-methyl-5-isoxazolyl)-2-(6-methanesulfonyl-2,3,4-trimethoxyphenylaminocarbonyl)thiophene-3-sulfonamide;
N-(4-chloro-3-methyl-5-isoxazolyl)-2-(6-cyanomethyl-2,3,4-trimethoxyphenylaminocarbonyl)thiophene-3-sulfonamide;
N-(4-chloro-3-methyl-5-isoxazolyl)-2-(6-(2-hydroxyethyl)-2,3,4-trimethoxyphenylaminocarbonyl)thiophene-3-sulfonamide;
N-(4-chloro-3-methyl-5-isoxazolyl)-2-(6-cyano-2,3,4-trimethoxyphenylaminocarbonyl)thiophene-3-sulfonamide;
N-(4-chloro-3-methyl-5-isoxazolyl)-2-(6-methyl-2,3,4-trimethoxyphenylacetyl)thiophene-3-sulfonamide;
N-(4-chloro-3-methyl-5-isoxazolyl)-2-(6-acetyl-2,3,4-trimethoxyphenylacetyl)thiophene-3-sulfonamide;
N-(4-chloro-3-methyl-5-isoxazolyl)-2-(6-methoxycarbonyl-2,3,4-trimethoxyphenylacetyl)thiophene-3-sulfonamide;
N-(4-chloro-3-methyl-5-isoxazolyl)-2-(6-carboxyl-2,3,4-trimethoxyphenylacetyl)thiophene-3-sulfonamide;
N-(4-chloro-3-methyl-5-isoxazolyl)-2-(6-methanesulfonyl-2,3,4-trimethoxyphenylacetyl)thiophene-3-sulfonamide;
N-(4-chloro-3-methyl-5-isoxazolyl)-2-(6-cyanomethyl-2,3,4-trimethoxyphenylacetyl)thiophene-3-sulfonamide;
N-(4-chloro-3-methyl-5-isoxazolyl)-2-(6-(2-hydroxyethyl)-2,3,4-trimethoxyphenylacetyl)thiophene-3-sulfonamide;
N-(4-chloro-3-methyl-5-isoxazolyl)-2-(6-methyl-3,4-(methylenedioxy)-2-methoxyphenylaminocarbonyl)thiophene-3-sulfonamide;
N-(4-chloro-3-methyl-5-isoxazolyl)-2-(6-acetyl-3,4-(methylenedioxy)-2-methoxyphenylaminocarbonyl)thiophene-3-sulfonamide;
N-(4-chloro-3-methyl-5-isoxazolyl)-2-(6-methoxycarbonyl-3,4-(methylenedioxy)-2-methoxyphenylaminocarbonyl)thiophene-3-sulfonamide;
N-(4-chloro-3-methyl-5-isoxazolyl)-2-(6-carboxyl-3,4-(methylenedioxy)-2-methoxyphenylaminocarbonyl)thiophene-3-sulfonamide;
N-(4-chloro-3-methyl-5-isoxazolyl)-2-(6-methanesulfonyl-3,4-(methylenedioxy)-2-methoxyphenylaminocarbonyl)thiophene-3-sulfonamide;
N-(4-chloro-3-methyl-5-isoxazolyl)-2-(6-cyanomethyl-3,4-methylenedioxy)-2-methoxyphenylaminocarbonyl)thiophene-3-sulfonamide;
N-(4-chloro-3-methyl-5-isoxazolyl)-2-(6-(2-hydroxyethyl)-3,4-(methylenedioxy)-2-methoxyphenylaminocarbonyl)thiophene-3-sulfonamide;
N-(4-chloro-3-methyl-5-isoxazolyl)-2-(6-cyano-3,4-(methylenedioxy)-2-methoxyphenylaminocarbonyl)thiophene-3-sulfonamide;
N-(4-chloro-3-methyl-5-isoxazolyl)-2-(2,6-dimethyl-3,4-(methylenedioxy)phenylaminocarbonyl)thiophene-3-sulfonamide;
N-(4-chloro-3-methyl-5-isoxazolyl)-2-(6-acetyl-3,4-(methylenedioxy)-2-methylphenylaminocarbonyl)thiophene-3-sulfonamide;
N-(4-chloro-3-methyl-5-isoxazolyl)-2-(6-methoxycarbonyl-3,4-(methylenedioxy)-2-methylphenylaminocarbonyl)thiophene-3-sulfonamide;
N-(4-chloro-3-methyl-5-isoxazolyl)-2-(6-carboxyl-3,4-(methylenedioxy)-2-methylphenylaminocarbonyl)thiophene-3-sulfonamide;
N-(4-chloro-3-methyl-5-isoxazolyl)-2-(6-methanesulfonyl-3,4-(methylenedioxy)-2-methylphenylaminocarbonyl)thiophene-3-sulfonamide;
N-(4-chloro-3-methyl-5-isoxazolyl)-2-(6-cyanomethyl-3,4-(methyenedioxy)-2-methylphenylaminocarbonyl)thiophene-3-sulfonamide;

N-(4-chloro-3-methyl-5-isoxazolyl)-2-(6-(2-hydroxyethyl)-3,4-(methylenedioxy)-2-methylphenylaminocarbonyl)thiophene-3-sulfonamide;

N-(4-chloro-3-methyl-5-isoxazolyl)-2-(6-cyano-3,4-(methylenedioxy)-2-methylphenylaminocarbonyl)thiophene-3-sulfonamide;

N-(4-chloro-3-methyl-5-isoxazolyl)-2-(6-methoxy-3,4-(methylenedioxy)-2-methylphenylaminocarbonyl)thiophene-3-sulfonamide;

N-(4-chloro-3-methyl-5-isoxazolyl)-2-(2-cyano-3,4-(methylenedioxy)-6-methylphenylaminocarbonyl)thiophene-3-sulfonamide;

N-(4-chloro-3-methyl-5-isoxazolyl)-2-(2-cyano-3,4-(methylenedioxy)-6-methoxyphenylaminocarbonyl)thiophene-3-sulfonamide;

N-(4-chloro-3-methyl-5-isoxazolyl)-2-(2-acetyl-3,4-(methylenedioxy)-6-methylphenylaminocarbonyl)thiophene-3-sulfonamide;

N-(4-chloro-3-methyl-5-isoxazolyl)-2-(2-acetyl-3,4-(methylenedioxy)-6-methoxyphenylaminocarbonyl)thiophene-3-sulfonamide;

N-(4-chloro-3-methyl-5-isoxazolyl)-2-(6-methyl-3,4-(methylenedioxy)-2-methoxyphenylacetyl)thiophene-3-sulfonamide;

N-(4-chloro-3-methyl-5-isoxazolyl)-2-(6-acetyl-3,4-(methylenedioxy)-2-methoxyphenylacetyl)thiophene-3-sulfonamide;

N-(4-chloro-3-methyl-5-isoxazolyl)-2-(6-methoxycarbonyl-3,4-(methylenedioxy)-2-methoxyphenylacetyl)thiophene-3-sulfonamide;

N-(4-chloro-3-methyl-5-isoxazolyl)-2-(6-carboxyl-3,4-(methylenedioxy)-2-methoxyphenylacetyl)thiophene-3-sulfonamide;

N-(4-chloro-3-methyl-5-isoxazolyl)-2-(6-methanesulfonyl-3,4-(methylenedioxy)-2-methoxyphenylacetyl)thiophene-3-sulfonamide;

N-(4-chloro-3-methyl-5-isoxazolyl)-2-(6-cyanomethyl-3,4-(methylenedioxy)-2-methoxyphenylacetyl)thiophene-3-sulfonamide;

N-(4-chloro-3-methyl-5-isoxazolyl)-2-(6-(2-hydroxyethyl)-3,4-(methylenedioxy)-2-methoxyphenylacetyl)thiophene-3-sulfonamide;

N-(4-chloro-3-methyl-5-isoxazolyl)-2-(6-cyano-3,4-(methylenedioxy)-2-methoxyphenylacetyl)thiophene-3-sulfonamide;

N-(4-chloro-3-methyl-5-isoxazolyl)-2-(2,6-dimethyl-3,4-(methylenedioxy)phenylacetyl)thiophene-3-sulfonamide;

N-(4-chloro-3-methyl-5-isoxazolyl)-2-(6-acetyl-3,4-(methylenedioxy)-2-methylphenylacetyl)thiophene-3-sulfonamide;

N-(4-chloro-3-methyl-5-isoxazolyl)-2-(6-methoxycarbonyl-3,4-(methylenedioxy)-2-methylphenylacetyl)thiophene-3-sulfonamide;

N-(4-chloro-3-methyl-5-isoxazolyl)-2-(6-carboxyl-3,4-(methylenedioxy)-2-methylphenylacetyl)thiophene-3-sulfonamide;

N-(4-chloro-3-methyl-5-isoxazolyl)-2-(6-methanesulfonyl-3,4-(methylenedioxy)-2-methylphenylacetyl)thiophene-3-sulfonamide;

N-(4-chloro-3-methyl-5-isoxazolyl)-2-(6-cyanomethyl-3,4-(methylenedioxy)-2-methylphenylacetyl)thiophene-3-sulfonamide;

N-(4-chloro-3-methyl-5-isoxazolyl)-2-(6-(2-hydroxyethyl)-3,4-(methylenedioxy)-2-methylphenylacetyl)thiophene-3-sulfonamide;

N-(4-chloro-3-methyl-5-isoxazolyl)-2-(6-cyano-3,4-(methylenedioxy)-2-methylphenylacetyl)thiophene-3-sulfonamide;

N-(4-chloro-3-methyl-5-isoxazolyl)-2-(6-methoxy-3,4-(methylenedioxy)-2-methylphenylacetyl)thiophene-3-sulfonamide;

N-(4-chloro-3-methyl-5-isoxazolyl)-2-(2-cyano-3,4-(methylenedioxy)-6-methylphenylacetyl)thiophene-3-sulfonamide;

N-(4-chloro-3-methyl-5-isoxazolyl)-2-(2-cyano-3,4-(methylenedioxy)-6-methoxyphenylacetyl)thiophene-3-sulfonamide;

N-(4-chloro-3-methyl-5-isoxazolyl)-2-(2-acetyl-3,4-(methylenedioxy)-6-methylphenylacetyl)thiophene-3-sulfonamide;

N-(4-chloro-3-methyl-5-isoxazolyl)-2-(2-acetyl-3,4-(methylenedioxy)-6-methoxyphenylacetyl)thiophene-3-sulfonamide;

N-(4-chloro-3-methyl-5-isoxazolyl)-2-(2,6-bis(cyanomethyl)-3,4-(methylenedioxy)phenylaminocarbonyl)thiophene-3-sulfonamide.

Thus, subject to the above proviso, the preferred sulfonamides or pharmaceutically acceptable salts, acids and esters thereof, of formula (A) have formula I:

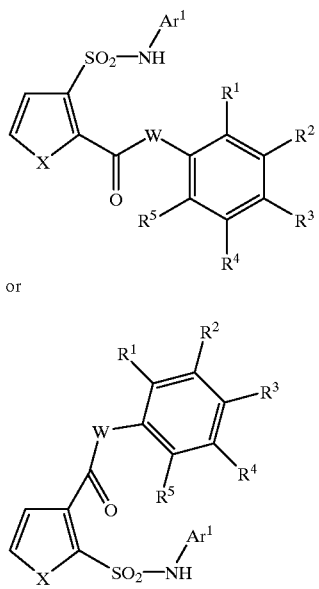

(I)

or

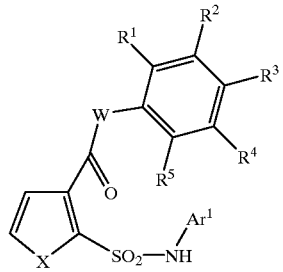

or pharmaceutically acceptable acids, esters and salts thereof, where $Ar^1$ is a substituted or unsubstituted monocyclic or polycyclic, preferably a monocyclic or fused bicyclic, aryl or heteroaryl group with one or more substituents, selected from, for example, H, $NH_2$, halide, pseudohalide, alkyl, alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceding groups, and straight or branched chains of from about 1 up to about 10–12 carbons, preferably, 1 to about 5 or 6 carbons. The substituents are preferably H, $NH_2$, halide, $CH_3$, $CH_3O$ or another aromatic group, and the sulfonamides are preferably the thiophene-3-sulfonamides. $R^1$–$R^5$ are as defined above.

In particular, $Ar^1$ is a five or six membered substituted or unsubstituted aromatic or heteroaromatic ring or a fused bicyclic substituted or unsubstituted aromatic or heteroaromatic ring, preferably an isoxazolyl, pyridazinyl, thiazolyl, pyrimidinyl or phenyl groups and particularly 3- or 5-isoxazolyl, benzo-2,1,3-thiadiazol-5-yl; 2-pyrazinyl or benzo-1,2,7-oxadiazol-4-yl;

W is $=C(halo)_2$, $—(CH_2)_x—$, $=N(lower\ alkyl)$, $—C(O)—$, $=C(lower\ alkyl)_2$, $—NH—$, $=NCOR^{16}$, $—NHC(R^{12})(R^{16})—$, $=NCO_2R^{16}$ or $=CHR^6$; x is 0–3; $R^1$, $R^2$, $R^3$, $R^4$, and $R^5$ are each selected independently from Z, as defined above, or any two may form a ring containing two or more heteroatoms; and $R^6$ is H, or substituted or unsubstituted alkyl or aryl, preferably H or substituted or unsubstituted lower alkyl, more preferably H, methyl or carboxymethyl.

In all embodiments, X is preferably S.

$Ar^1$ is preferably an isoxazolyl of formula:

in which $R^A$ and $R^B$ are either (i), (ii) or (iii) as follows:
(i) $R^A$ and $R^B$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that $R^2$ is not halide or pseudohalide; or,
(ii) $R^A$ and $R^B$ together form $—(CH_2)_n$, where n is 3 to 6; or,
(iii) $R^A$ and $R^B$ together form 1,3-butadienyl.

In preferred embodiments herein, $R^A$ and $R^B$ are each selected independently from among alkyl, lower alkenyl, lower alkynyl, lower haloalkyl, halide, pseudohalide or H, except that $R^B$ is not halide.

Preferred compounds herein are selected with the provisos that when $Ar^1$ is an isoxazolyl, particularly 4-chloro-3-methyl-5-isoxazolyl and W is —NH—:

(a) if $R^1$, $R^3$ and $R^5$ are methyl, and $R^4$ is H; then $R^2$ is not cyanomethyl, hydroxymethyl, cyano, methoxycarbonyl, carboxyl, methanesulfonyl, 2-hydroxyethyl;

(b) if $R^1$ is methoxy or is methyl when $R^2$ and $R^3$ together form methylenedioxy, $R^2$ and $R^3$ are methoxy or together form methylenedioxy, and $R^4$ is H; then $R^5$ is not methyl, cyano, acetyl, methoxycarbonyl, carboxyl, methanesulfonyl, cyanomethyl or 2-hydroxyethyl, and is not methoxy when $R^1$ is methyl;

(c) if $R^1$ is cyano or acetyl, $R^2$ and $R^3$ together form methylenedioxy, and $R^4$ is H; then $R^5$ is not methyl or methoxy;

(d) if $R^1$ is cyanomethyl, $R^2$ and $R^3$ together form methylenedioxy, and $R^4$ is H; then $R^5$ is not cyanomethyl;

and with the additional provisos that when $Ar^1$ is 4-chloro-3-methyl-5-isoxazolyl and W is $—CH_2—$:

(a) if $R^1$, $R^3$ and $R^5$ are methyl, and $R^4$ is H; then $R^2$ is not cyanomethyl, hydroxymethyl, cyano, methoxycarbonyl, carboxyl, methanesulfonyl, 2-hydroxyethyl;

(b) if $R^1$ is methoxy when $R^2$ and $R^3$ are methoxy or together form methylenedioxy, or is methyl when $R^2$ and $R^3$ together form methylenedioxy, and $R^4$ is H; then $R^5$ is not: (i) methyl, acetyl, methoxycarbonyl, carboxyl, methanesulfonyl, cyanomethyl or 2-hydroxyethyl, and additionally (ii) is not methoxy or cyano when $R^1$ is methyl, and (iii) is not cyano when $R^1$ is methoxy and $R^2$ and $R^3$ together form methylenedioxy;

(c) if $R^1$ is cyano or acetyl, $R^2$ and $R^3$ together form methylenedioxy, and $R^4$ is H; then $R^5$ is not methyl or methoxy.

In one embodiment, the sulfonamides and pharmaceutically acceptable salts, acids and esters thereof have formula II:

(II)

where $Ar^1$ is as defined above and $R^7$ is $R^1$, $R^8$ is $R^3$, $R^9$ is $R^4$ and $R^{10}$ is $R^5$. In particular, $Ar^2$ is a five or six membered substituted or unsubstituted aromatic or heteroaromatic ring or a fused bicyclic substituted or unsubstituted aromatic or heteroaromatic ring, preferably 3- or 5-isoxazolyl, benzo-1,2,7-thiadiazol-4-yl, 2-pyrazinyl or benzo-1,2,7-oxadiazol-4-yl, more preferably 4-chloro-3-methyl-5-isoxazolyl or 4-chloro-5-methyl-3-isoxazolyl; W is —NH—, $=NCOR^{16}$, $=NCO_2R^{16}$, $—NHC(R^{12})(R^{16})—$ or is $—CH_2—$ when $R^9$ is hydroxyl.

In preferred of these embodiments, $R^9$ is selected from the group consisting of substituted and unsubstituted alkyl, hydroxyl, substituted and unsubstituted alkoxy, $OC(O)R^{16}$, $OCO_2R^{16}$, $NR^{12}R^{16}$ and $S(O)_nR^{16}$ in which n is 0–2, preferably alkoxycarbonylalkyl, carboxyalkyl, dialkylaminoalkyl, alkylsulfonylamino and aminosulfonyl with the proviso that, when W is $—NHC(R^{12})(R^{16})—$, then $R^7$, $R^8$, $R^9$ and $R^{10}$ can be H.

$R^7$, $R^8$ and $R^{10}$ are preferably alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, or heteroarylalkyl, more preferably lower alkyl, lower alkenyl, lower alkynyl, or aryl, most preferably methyl. The sulfonamides are preferably thiophene-3-sulfonamides.

In certain embodiments of formula (II), the compounds are selected with the proviso that when $Ar^1$ is 4-chloro-3-methyl-5-isoxazolyl and W is —NH—:

if $R^7$, $R^8$ and $R^{10}$ are methyl; then $R^9$ is not cyanomethyl, hydroxymethyl, cyano, methoxycarbonyl, carboxyl, methanesulfonyl, or 2-hydroxyethyl;

if $R^{10}$ is methoxy or is methyl when $R^8$ and $R^9$ together form methylenedioxy and $R^8$ and $R^9$ are methoxy or together form methylenedioxy; then $R^7$ is not methyl, cyano, acetyl, methoxycarbonyl, carboxyl, methanesulfonyl, cyanomethyl or 2-hydroxyethyl, and is not methoxy when $R^{10}$ is methyl;

if $R^{10}$ is cyano or acetyl and $R^8$ and $R^9$ together form methylenedioxy; then $R^7$ is not methyl or methoxy; and if $R^{10}$ is cyanomethyl and $R^8$ and $R^9$ together form methylenedioxy; then $R^7$ is not cyanomethyl;

and with the additional proviso that $R^7$, $R^8$, $R^9$ and $R^{10}$ may be H when W is —NHC($R^{12}$)($R^{16}$)—.

In more preferred embodiments, the sulfonamides of formula II are those in which $R^7$, $R^8$, $R^9$ and $R^{10}$ do not contain cyano groups and W is not —CH$_2$—. These compounds are among those preferred because, among other properties, they appear to exhibit improved toxicological profiles relative to other compounds of formula II.

In another embodiment of formula (A), the sulfonamides have formulae III:

(III)

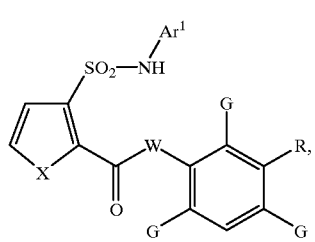

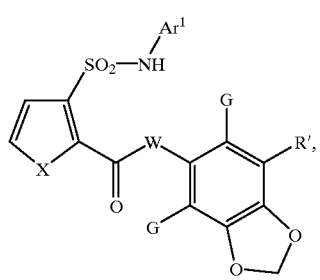

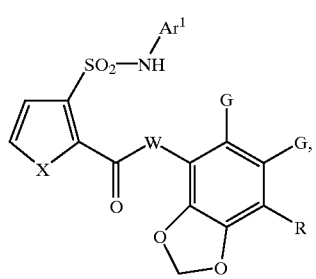

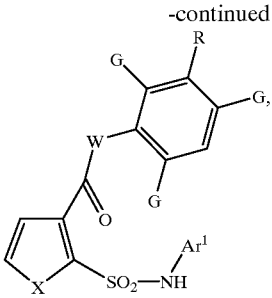

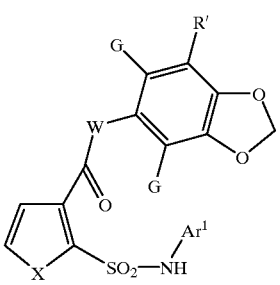

or

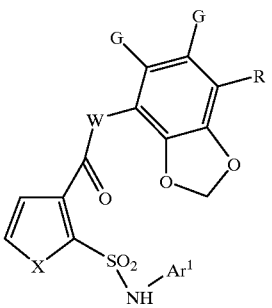

where $Ar^1$ is as define above. $Ar^1$ is a five or six membered substituted or unsubstituted aromatic or heteroaromatic ring or a fused bicyclic substituted or unsubstituted aromatic or heteroaromatic ring, preferably 3- or 5-isoxazolyl, benzo-1,2,7-thiadiazol-4-yl, 2-pyrazinyl or benzo-1,2,7-oxadiazol-4-yl;

X is preferably S;

each G and R is independently selected from lower alkyl, CN, —(CH$_2$)$_x$C(O)(CH$_2$)$_x$, —(CH$_2$)$_x$, (CH$_2$)$_x$N-lower alkyl, —(CH$_2$)$_x$C(O)NH$_2$, a D-, L- or racemic amino acid, a primary or secondary amide, O-glycoside, a hexose or ribose, —S(O )$_2$NH$_2$, hydroxy, alkoxy, alkoxycarbonyl, acetoxyalkyl, —(CH$_2$)$_x$COOH; —(CH$_2$)$_x$COOH—, CO$_2$-lower alkyl, CN, heteroaryl, —COC(O)(CH$_2$)$_x$CH$_3$, —(CH$_2$)$_x$N(CH$_3$)$_2$, a sulfonyl chloride, S(O)$_2$NHR$^{50}$, alkylaryl, alkylheteroaryl, C(O)NHR$^{50}$, —(CH$_2$)$_x$OH, —C(O)N(H)N(H)M; M is H or R$^{50}$; R' is selected from hydrogen, G and R; W is =C(halo)$_2$, =N(H), —(CH$_2$)$_x$—, =N(lower alkyl), —C(O)—, =C(lower alkyl)$_2$; and x is 0–3.

In another embodiment, the sulfonamides have formula IV:

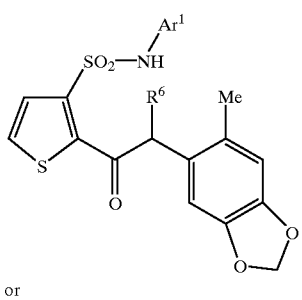

(IV)

or

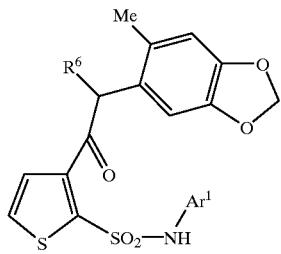

where:

Ar¹ is defined as above, except when R⁶ is H, then Ar¹ is not 4-chloro-3-methyl-5-isoxazolyl, 4-chloro-5-methyl-3-isoxazolyl or 3,4-dimethyl-5-isoxazoly. Ar¹ is preferably benzo-1,2,7-oxadiazol-4-yl or 2-methoxy-3-pyrazinyl when R⁶ is H; and R⁶ is H, or substituted or unsubstituted alkyl or aryl, preferably H or substituted or unsubstituted lower alkyl, more preferably methyl or carboxymethyl.

In other embodiments of formula (IV), Ar¹ is preferably benzo-1,2,7-oxadiazol-4-yl or 2-methoxy-3-pyrazinyl when R⁶ is H and R⁶ is H, or substituted or unsubstituted alkyl or aryl, preferably H or substituted or unsubstituted lower alkyl, more preferably methyl or carboxymethyl.

In another embodiment, the sulfonamides have formula V:

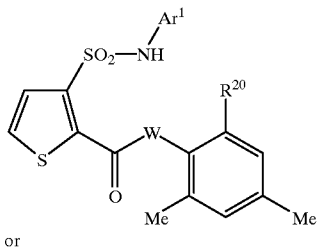

(V)

or

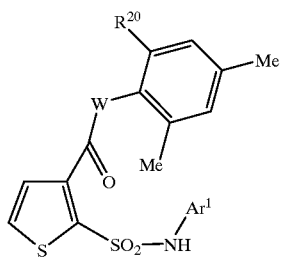

where Ar¹ is defined as above and is preferably 4-chloro-3-methyl-5-isoxazolyl; W is NH; and $R^{20}$ is selected from the group consisting of aryl, heteroaryl, heterocycle, OH, CN, C(O)$R^{16}$, CO$_2$$R^{16}$, SH, S(O)$_n$$R^{16}$ in which n is 0–2, a D, L or racemic amino acid, a ribose or hexose, an O-glycoside, a sulfonyl chloride, —(CH$_2$)$_x$OH, NHOH, NR$^{12}$R$^{16}$, NO$_2$, N$_3$, OR$^{16}$, R$^{12}$NCOR$^{16}$ and CONR$^{12}$R$^{16}$;

$R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$ is selected from hydrogen, alkyl, alkenyl, alkynyl, aryl, alkylaryl, heterocycle, aralkyl, aralkoxy, cycloalkyl, cycloalkenyl, cycloalkynyl, C(O)$R^{17}$ and S(O)$_n$$R^{17}$ in which n is 0–2; $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{12}$, $R^{15}$ and $R^{16}$ may be further substituted with the any of the groups set forth for Z; $R^{20}$ is preferably CONH$^2$, COOH, or phenyl.

Of the compounds described herein, those that inhibit or increase an endothelin-mediated activity by about 50% at concentrations of less than about 10 μM are preferred. More preferred are those that inhibit or increase an endothelin-mediated activity by about 50% at concentrations of less than about 1 μM, more preferably less than about 0.1 μM, even more preferably less than about 0.01 μM, and most preferably less than about 0.001 μM. It is noted that, as described below, the IC$_{50}$ concentration determined in the in vitro assays is a non-linear function of incubation temperature. The preferred values recited herein refer to the assays that are performed at 4° C. When the assays are performed at 24° C., somewhat higher (see, Table 1) IC$_{50}$ concentrations are observed. Accordingly, the preferred IC$_{50}$ concentrations are about 10-fold higher. Furthermore, among these compounds, those that exhibit the greatest bioavailability and stability, as determined using standard animal models Also among the most preferred compounds for use in methods provided herein, are those that are ET$_A$ selective, i.e., they interact with ET$_A$ receptors at substantially lower concentrations (at an IC$_{50}$ at least about 10-fold lower, preferably 100-fold lower) than they interact with ET$_B$ receptors. In particular, compounds that interact with ET$_A$ with an IC$_{50}$ of less than about 10 μM, preferably less than 1 μM, more preferably less than 0.1 μM, but with ET$_B$ with an IC$_{50}$ of greater than about 10 μM or compounds that interact with ET$_B$ with an IC$_{50}$ of less than about 10 μM, preferably less than 1 μM, more preferably less than 0.1 μM, but with ET$_A$ with an IC$_{50}$ of greater than about 10 μM are preferred.

Also of interest are any pharmaceutically-acceptable derivatives, including salts, esters, acids and bases, solvates, hydrates and prodrugs of the sulfonamides. Preferred are pharmaceutically-acceptable salts, including, but not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine, tris(hydroxymethyl) aminomethane, alkali metal salts, such as but not limited to lithium, potassium and sodium, alkali earth metal salts, such as but not limited to barium, calcium and magnesium, transition metal salts, such as but not limited to zinc and other metal salts, such as but not limited to sodium hydrogen phosphate and disodium phosphate, preferably sodium salts, more preferably the sodium salt, and also including, but not limited to, salts of mineral acids, such as but not limited to hydrochlorides and sulfates, salts of organic acids, such as but not limited to acetates, lactates, malates, tartrates, citrates, ascorbates, succinates, butyrates, valerates and fumarates. Alkali metal salts, particularly sodium salts, are preferred herein. Most preferred salts are sodium salts.

Pharmaceutical formulations for administration by an appropriate route and means containing effective concentrations of one or more of the compounds provided herein or pharmaceutically acceptable salts, esters, acids and bases, solvates, hydrates and prodrugs of the sulfonamides, preferably salts, more preferably sodium salts, including but not limited to sodium salts and sodium hydrogen phosphate salts, most preferably the sodium salt, thereof that deliver amounts effective for the treatment of hypertension, stroke, cardiovascular diseases, cardiac diseases including myocardial infarction, pulmonary hypertension, erythropoietin-mediated hypertension, respiratory diseases, inflammatory diseases, including asthma, bronchoconstriction, ophthalmologic diseases including glaucoma and inadequate retinal perfusion, gastroenteric diseases, renal failure, endotoxin shock, menstrual disorders, obstetric conditions, wounds, anaphylactic shock, hemorrhagic shock, and other diseases in which endothelin mediated physiological responses are implicated or that involve vasoconstriction or whose symptoms can be ameliorated by administration of an endothelin antagonist or agonist, are also provided.

The formulations are compositions suitable for administration by any desired route and include solutions, suspensions, emulsions, tablets, dispersible tablets, pills, capsules, powders, dry powders for inhalation, sustained release formulations, aerosols for nasal and respiratory delivery, patches for transdermal delivery and any other suitable route. The compositions should be suitable for oral administration, parenteral administration by injection, including subcutaneously, intramuscularly or intravenously as an injectable aqueous or oily solution or emulsion, transdermal administration and other selected routes.

Lyophilized powders of the sulfonamide derivatives, methods for preparation thereof, and formulations containing reconstituted forms of the lyophilized powders are also provided. Vials and ampules and syringes and other suitable vessels containing the powders are also provided.

Preferred formulations include a sterile lyophilized powder containing pharmaceutically-acceptable salts, preferably sodium salts, more preferably a sodium salt, of a sulfonamide, and also include capsules and tablets. Particularly preferred formulations are those that deliver amounts effective for the treatment of hypertension or renal failure. The effective amounts and concentrations are effective for ameliorating any of the symptoms of any of the disorders.

In one embodiment, the formulations are lyophilized solids containing one or more salts, preferably sodium hydrogen phosphate or sodium salts, more preferably sodium salts, of one or more sulfonamide compounds of formula I and also contain one or more of the following: a buffer, such as sodium or potassium phosphate, or citrate; a solubilizing agent, such as LABRASOL (polyethylene glycol-8 caprylic capric glycerides sold by Gattefosse SA, France), DMSO, bis(trimethylsilyl)acetamide, ethanol, propyleneglycol (PG), or polyvinylpyrrolidine (PVP); and a sugar or other carbohydrate, such as sorbitol or dextrose.

In other embodiments, the formulations are solid dosage forms, preferably capsules or tablets. In a preferred embodiment, the formulations are solid dosage forms, preferably capsules or tablets, containing 10–100%, preferably 50–95%, more preferably 75–85%, most preferably 80–85%, by weight, of one or more salts, preferably sodium hydrogen phosphate or sodium salts, more preferably the sodium salts, of one or more sulfonamide compounds of formula I; about 0–25%, preferably 8–15%, of an excipient or a binder, such as lactose or microcrystalline cellulose; about 0 to 10%, preferably about 3–7%, of a disintegrant, such as a modified starch or cellulose polymer, particularly a cross-linked sodium carboxymethyl cellulose, such as crosscarmellose sodium (Crosscarmellose sodium NF is available commercially under the name AC-DI-SOL, FMC Corporation, Philadelphia, Pa.) or sodium starch glycolate; and 0–2% of a lubricant, such a magnesium stearate, talc and calcium stearate. The disintegrant, such as crosscarmellose sodium or sodium starch glycolate, provides for rapid break-up of the cellulosic matrix for immediate release of active agent following dissolution of coating polymer. In all embodiments, the precise amount of active ingredient and auxiliary ingredients can be determined empirically and is a function of the route of administration and the disorder that is treated.

In an exemplary embodiment, the formulations are capsules containing about 80–100%, preferably about 75–95%, more preferably about 83%, of one or more sodium salts of one or more sulfonamide compounds of formula I; about 0–15%, preferably about 11% of an excipient or a binder, such as lactose or microcrystalline cellulose; about 0–10%, preferably about 5% of a disintegrant, such as crosscarmellose sodium or sodium starch glycolate; and about 0 to 5%, preferably about 1% of a lubricant, such as magnesium stearate. Solid forms for administration as tablets are also contemplated herein. It is understood that precise amounts and composition thereof can be empirically determined by the skilled artisan.

Methods using such formulations for modulating the interaction of an endothelin peptide with $ET_A$ and/or $ET_B$ receptors are provided. The methods are effected by contacting the receptors with one or more of the formulated pharmaceutically-acceptable salts of the sulfonamides, preferably formulated sodium salts of the sulfonamides, prior to, simultaneously with, or subsequent to contacting the receptors with an endothelin peptide.

Methods for inhibiting binding of an endothelin peptide to an endothelin receptor are provided. These methods are practiced by contacting the receptor with one or more of the compounds or one or more of the formulations of pharmaceutically-acceptable salts of the compounds provided herein simultaneously, prior to, or subsequent to contacting the receptor with an endothelin peptide.

Methods for treatment of endothelin-mediated disorders, including, but not limited to, hypertension, asthma, shock, ocular hypertension, glaucoma, inadequate retinal perfusion and other conditions that are in some manner mediated by an endothelin peptide, or for treatment of disorder that involve vasoconstriction or that are ameliorated by administration of an endothelin antagonist or agonist are provided.

In particular, methods of treating endothelin-mediated disorders by administering effective amounts of the sulfonamides, prodrugs or other suitable derivatives of the sulfonamides are provided. In particular, methods for treating endothelin-mediated disorders, including hypertension, cardiovascular diseases, cardiac diseases including myocardial infarction, pulmonary hypertension, erythropoietin-mediated hypertension, respiratory diseases and inflammatory diseases, including asthma, bronchoconstriction, ophthalmologic diseases, gastroenteric diseases, renal failure, endotoxin shock, menstrual disorders, obstetric conditions, wounds, anaphylactic shock, hemorrhagic shock, and other diseases in which endothelin mediated physiological responses are implicated, by administering effective amounts of one or more of the compounds provided herein in pharmaceutically acceptable carriers are provided.

Preferred methods of treatment are methods for treatment of hypertension and renal failure.

More preferred methods of treatment are those in which the formulations contain at least one compound that inhibits the interaction of endothelin-1 with $ET_A$ receptors at an $IC_{50}$ of less than about 10 µM, and preferably less than about 5 µM, more preferably less than about 1 µM, even more preferably less than 0.1 µM, and most preferably less than 0.05 µM Other preferred methods are those in which the formulations contain pharmaceutically-acceptable salts of one or more compounds that is (are) $ET_A$ selective or pharmaceutically-acceptable salts of one or more compounds that is (are) $ET_B$ selective. Methods in which the compounds are $ET_A$ selective are for treatment of disorders, such as hypertension; and methods in which the compounds are $ET_B$ selective are for treatment of disorders, such as asthma, that require bronchodilation.

In practicing the methods, effective amounts of formulations containing therapeutically effective concentrations of the compounds formulated for oral, intravenous, local and topical application for the treatment of hypertension, cardiovascular diseases, cardiac diseases, including myocardial infarction, respiratory diseases, including asthma, inflammatory diseases, ophthalmologic diseases, gastroenteric diseases, renal failure, immunosuppressant-mediated renal vasoconstriction, erythropoietin-mediated vasoconstriction, endotoxin shock, anaphylactic shock, hemorrhagic shock, pulmonary hypertension, and other diseases in which endothelin mediated physiological responses are implicated are administered to an individual exhibiting the symptoms of one or more of these disorders. The amounts are effective to ameliorate or eliminate one or more symptoms of the disorders.

Methods for the identification and isolation of endothelin receptor subtypes are also provided. In particular, methods for detecting, distinguishing and isolating endothelin receptors using the disclosed compounds are provided. In particular, methods are provided for detecting, distinguishing and isolating endothelin receptors using the compounds provided herein.

In addition, methods for identifying compounds that are suitable for use in treating particular diseases based on their preferential affinity for a particular endothelin receptor subtype are also provided.

Articles of manufacture containing packaging material, a compound provided herein, which is effective for ameliorating the symptoms of an endothelin-mediated disorder, antagonizing the effects of endothelin or inhibiting binding of an endothelin peptide to an ET receptor with an $IC_{50}$ of less than about 10 µM, within the packaging material, and a label that indicates that the compound or formulated pharmaceutically-acceptable salt thereof is used for antagonizing the effects of endothelin, treating an endothelin-mediated disorder, or inhibiting the binding of an endothelin peptide to an ET receptor are provided.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, endothelin (ET) peptides include peptides that have substantially the amino acid sequence of endothelin-1, endothelin-2 or endothelin-3 and that act as potent endogenous vasoconstrictor peptides.

As used herein, an endothelin-mediated condition is a condition that is caused by abnormal endothelin activity or one in which compounds that inhibit endothelin activity have therapeutic use. Such diseases include, but are not limited to hypertension, cardiovascular disease, asthma, inflammatory diseases, ophthalmologic disease, menstrual disorders, obstetric conditions, gastroenteric disease, renal failure, pulmonary hypertension, endotoxin shock, anaphylactic shock, or hemorrhagic shock. Endothelin-mediated conditions also include conditions that result from therapy with agents, such as erythropoietin and immunosuppressants, that elevate endothelin levels.

As used herein an effective amount of a compound for treating a particular disease is an amount that is sufficient to ameliorate, or in some manner reduce the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

As used herein, an endothelin agonist is a compound that potentiates or exhibits a biological activity associated with or possessed by an endothelin peptide.

As used herein, an endothelin antagonist is a compound, such as a drug or an antibody, that inhibits endothelin-stimulated vasoconstriction and contraction and other endothelin-mediated physiological responses. The antagonist may act by interfering with the interaction of the endothelin with an endothelin-specific receptor or by interfering with the physiological response to or bioactivity of an endothelin isopeptide, such as vasoconstriction. Thus, as used herein, an endothelin antagonist interferes with endothelin-stimulated vasoconstriction or other response or interferes with the interaction of an endothelin with an endothelin-specific receptor, such as $ET_A$ receptors, as assessed by assays known to those of skill in the art.

The effectiveness of potential agonists and antagonists can be assessed using methods known to those of skill in the art. For example, endothelin agonist activity can be identified by its ability to stimulate vasoconstriction of isolated rat thoracic aorta or portal vein ring segments (Borges et al. (1989) "Tissue selectivity of endothelin" *Eur. J. Pharmacol.* 165: 223–230). Endothelin antagonist activity can be assessed by the ability to interfere with endothelin-induced vasoconstriction. Exemplary assays are set forth in the EXAMPLES. As noted above, the preferred $IC_{50}$ concentration ranges are set forth with reference to assays in which the test compound is incubated with the ET receptor-bearing cells at 4° C. Data presented for assays in which the incubation step is performed at the less preferred 24° C. are identified. It is understood that for purposes of comparison, these concentrations are somewhat higher than the concentrations determined at 4° C.

As used herein, bioavailability refers to the rate and extent of absorption. Methods for determining bioavailability are well known to those of skill in the art. For example, bioavailability of any of the compounds described herein can be determined empirically by administration of the compound to an animal, followed by taking blood samples over time and measuring the blood concentration of the compound. In vivo half life ($t_{1/2}$) is defined as the time it takes for the concentration of the compound in the blood to be reduced by one-half. Estimations of the area under the curve for intravenous administration can be used to estimate the area under the curve for oral administration, yielding bioavailability data. See, e.g., Milo Gibal (1991) Biopharmaceutics and Pharmacology, 4th edition (Lea and Sediger).

As used herein, efficacy refers to the maximal effect that can be produced by a compound. Efficacy can be determined by methods known to those of skill in the art. For example, it can be determined by the properties of the compound and its receptor-effector system and is reflected in the plateau of the concentration-effect curve. In vivo efficacy refers to efficacy which is determined in an animal model. For example, in vivo efficacy of the compounds described herein can be determined by hypoxia-induced pulmonary hypertension in rat. See, e.g., DiCarlo et al. (1995) *Am. J. Physiol.* 269:L690–L697.

As used herein, the biological activity or bioactivity of endothelin includes any activity induced, potentiated or influenced by endothelin in vivo. It also includes the ability to bind to particular receptors and to induce a functional response, such as vasoconstriction. It may be assessed by in vivo assays or by in vitro assays, such as those exemplified herein. The relevant activities include, but are not limited to, vasoconstriction, vasorelaxation and bronchodilation. For example, $ET_B$ receptors appear to be expressed in vascular endothelial cells and may mediate vasodilation and other such responses; whereas $ET_A$ receptors, which are endothelin-1-specific, occur on smooth muscle and are linked to vasoconstriction Any assay known to those of skill in the art to measure or detect such activity may be used to assess such activity (see, e.g., Spokes et al. (1989) *J. Cardiovasc. Pharmacol.* 13(Suppl. 5):S191–S192; Spinella et al. (1991) *Proc. Natl. Acad. Sci. USA* 88: 7443–7446; Cardell et al. (1991) *Neurochem. Int.* 18:571–574); and the Examples herein).

As used herein, the $IC_{50}$ refers to an amount, concentration or dosage of a particular test compound that achieves a 50% inhibition of a maximal response, such as binding of endothelin to tissue receptors, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein a sulfonamide that is $ET_A$ selective refers to sulfonamides that exhibit an $IC_{50}$ that is at least about 10-fold lower with respect to $ET_A$ receptors than $ET_B$ receptors.

As used herein, a sulfonamide that is $ET_B$ selective refers to sulfonamides that exhibit an $IC_{50}$ that is at least about 10-fold lower with respect to $ET_B$ receptors than $ET_A$ receptors.

As used herein, pharmaceutically acceptable salts, esters, hydrates, solvates or other derivatives of the compounds include any such salts, esters and other derivatives that may be prepared by those of skill in this art using known methods for such derivatization and that produce compounds that may be administered to animals or humans without substantial toxic effects and that either are pharmaceutically active or are prodrugs. Pharmaceutically-acceptable salts include, but are not limited to, salts of alkali metals and alkaline earth metals, including but not limited to sodium salts, potassium salts, lithium salts, calcium salts and magnesium salts; transition metal salts, such as zinc salts, copper salts and aluminum salts; polycationic counter ion salts, such as but not limited ammonium and substituted ammonium salts and organic amine salts, such as hydroxyalkylamines and alkylamines; salts of mineral acids, such as but not limited to hydrochlorides and sulfates, salts of organic acids, such as but not limited acetates, lactates, malates, tartrates, citrates, ascorbates, succinates, butyrate, valerate and fumarates. Also contemplated herein are the corresponding esters.

As used herein, reference to "sodium salts" refers to salts of any sodium compounds in which the counter ion includes $Na^+$ and can include other ions, such as $HPO_4^{2-}$; reference to a "sodium salt" (rather than sodium salts) refers specifically to a salt in which $Na^+$ is the counter ion.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, treatment means any manner in which the symptoms of a conditions, disorder or disease are ameliorated or otherwise beneficially altered. Treatment also encompasses any pharmaceutical use of the compositions herein, such as use as contraceptive agents.

As used herein, amelioration of the symptoms of a particular disorder by administration of a particular pharmaceutical composition refers to any lessening, whether permanent or temporary, lasting or transient that can be attributed to or associated with administration of the composition.

As used herein, substantially pure means sufficiently homogeneous to appear free of readily detectable impurities as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound.

As used herein, biological activity refers to the in vivo activities of a compound or physiological responses that result upon in vivo administration of a compound, composition or other mixture. Biological activity, thus, encompasses therapeutic effects and pharmaceutical activity of such compounds, compositions and mixtures.

As used herein, increased stability of a formulation means that the percent of active component present in the formulation, as determined by assays known to those of skill in the art, such as high performance liquid chromatography, gas chromatography, and the like, at a given period of time following preparation of the formulation is significantly higher than the percent of active component present in another formulation at the same period of time following preparation of the formulation. In this case, the former formulation is said to possess increased stability relative to the latter formulation.

As used herein, a prodrug is a compound that, upon in vivo administration, is metabolized or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach,* Oxford University Press, New York, pages 388–392). For example, succinylsulfathiazole is a prodrug of 4-amino-N-(2-thiazoyl) benzenesulfonamide(sulfathiazole) that exhibits altered transport characteristics.

As used herein, acid isostere means a group that is significantly ionized at physiological pH. Examples of suitable acid isosteres include sulfo, phosphono, alkylsulfonylcarbamoyl, tetrazolyl, arylsulfonylcarbamoyl or heteroarylsulfonylcarbamoyl.

As used herein, halo or halide refers to the halogen atoms; F, Cl, Br and I.

As used herein, pseudohalides are compounds that behave substantially similar to halides. Such compounds can be used in the same manner and treated in the same manner as halides (X$^-$, in which X is a halogen, such as Cl or Br). Pseudohalides include, but are not limited to cyanide, cyanate, thiocyanate, selenocyanate and azide.

As used herein, haloalkyl refers to a loweralkyl radical in which one or more of the hydrogen atoms are replaced by halogen including, but not limited to, chloromethyl, trifluoromethyl, 1-chloro-2-fluoroethyl and the like.

As used herein, alkyl means an aliphatic hydrocarbon group that is a straight or branched chain preferably having about 1 to 12 carbon atoms in the chain. Preferred alkyl groups are loweralkyl groups which are alkyls containing 1 to about 6 carbon atoms in the chain. Branched means that one or more loweralkyl groups such as methyl, ethyl or propyl are attached to a linear alkyl chain. The alkyl group may be unsubstituted or independently substituted by one or more groups, such as, but not limited to: halo, carboxy, formyl, sulfo, sulfino, carbamoyl, amino and imino. Exemplary alkyl groups include methyl, ethyl, propyl, carboxymethyl, carboxyethyl, carboxypropyl, sulfinoethyl and sulfoethyl As used herein the term lower describes alkyl, alkenyl and alkynyl groups containing about 6 carbon atoms or fewer. It is also used to describe aryl groups or heteroaryl groups that contain 6 or fewer atoms in the ring. Loweralkyl, lower alkenyl, and lower alkynyl refer to carbon chains having less than about 6 carbons. In preferred embodiments of the compounds provided herein that include alkyl, alkenyl, or alkynyl portions include loweralkyl, lower alkenyl, and lower alkynyl portions.

As used herein, alkenyl means an aliphatic hydrocarbon group containing a carbon-carbon double bond and which may be straight or branched chained having from about 2 to about 10 carbon atoms in the chain. Preferred alkenyl groups have 2 to about 4 carbon atoms in the chain. Branched means that one or more loweralkyl or lower alkenyl groups are attached to a linear alkenyl chain. The alkenyl group may be unsubstituted or independently substituted by one or more groups, such as halo, carboxy, formyl, sulfo, sulfino, carbamoyl, amino and imino. Exemplary alkenyl groups include ethenyl, propenyl, carboxyethenyl, carboxypropenyl, sulfinoethenyl and sulfonoethenyl.

As used herein, alkynyl means an aliphatic hydrocarbon group containing a carbon-carbon triple bond and which may be straight or branched having about 2 to 10 carbon atoms in the chain. Branched means that one or more loweralkyl, alkenyl or alkynyl groups are attached to a linear alkynyl chain. An exemplary alkynyl group is ethynyl.

As used herein, aryl means an aromatic monocyclic or multicyclic hydrocarbon ring system containing from 3 to 15 or 16 carbon atoms, preferably from 5 to 10. Aryl groups include, but are not limited to groups, such as phenyl, substituted phenyl, naphthyl, substituted naphthyl, in which the substituent is loweralkyl, halogen, or lower alkoxy. Preferred aryl groups are lower aryl groups that contain less than 7 carbons in the ring structure.

As used herein, the nomenclature alkyl, alkoxy, carbonyl, etc. are used as is generally understood by those of skill in this art. For example, as used herein alkyl refers to saturated carbon chains that contain one or more carbons; the chains may be straight or branched or include cyclic portions or be cyclic. As used herein, alicyclic refers to aryl groups that are cyclic.

As used herein, cycloalkyl refers to saturated cyclic carbon chains; cycloalkenyl and cycloalkynyl refer to cyclic carbon chains that include at least one unsaturated double or triple bond, respectively. The cyclic portions of the carbon chains may include one ring or two or more fused rings.

As used herein, cycloalkenyl means a non-aromatic monocyclic or multicyclic ring system containing a carbon-carbon double bond and having about 3 to about 10 carbon atoms. Exemplary monocyclic cycloalkenyl rings include cyclopentenyl or cyclohexenyl; preferred is cyclohexenyl. An exemplary multicyclic cycloalkenyl ring is norbornylenyl. The cycloalkenyl group may be independently substituted by one or more halo or alkyl.

As used herein, "haloalkyl" refers to a loweralkyl radical in which one or more of the hydrogen atoms are replaced by halogen including, but not limited to, chloromethyl, trifluoromethyl, 1-chloro-2-fluoroethyl and the like.

As used herein, "haloalkoxy" refers to RO— in which R is a haloalkyl group.

As used herein, "carboxamide" refers to groups of formula $R_p CONH_2$ in which R is selected from alkyl or aryl, preferably lower alkyl or lower aryl and p is 0 or 1.

As used herein, "alkylaminocarbonyl" refers to —C(O) NHR in which R is hydrogen, alkyl, preferably lower alkyl or aryl, preferably lower aryl.

As used herein "dialkylaminocarbonyl" as used herein refers to —C(O)NR'R in which R' and R are independently selected from alkyl or aryl, preferably lower alkyl or lower aryl; "carboxamide" refers to groups of formula NR'COR.

As used herein, "alkoxycarbonyl" as used herein refers to —C(O)OR in which R is alkyl, preferably lower alkyl or aryl, preferably lower aryl.

As used herein, "alkoxy" and "thioalkoxy" refer to RO— and RS—, in which R is alkyl, preferably loweralkyl or aryl, preferably lower aryl.

As used herein, "haloalkoxy" refers to RO— in which R is a haloalkyl group.

As used herein, "aminocarbonyl" refers to —C(O)NH$_2$.

As used herein, "alkylaminocarbonyl" refers to —C(O) NHR in which R is alkyl, preferably lower alkyl or aryl, preferably lower aryl.

As used herein, "alkoxycarbonyl" refers to —C(O)OR in which R is alkyl, preferably lower alkyl.

As used herein, cycloalkyl refers to saturated cyclic carbon chains; cycloalkyenyl and cycloalkynyl refer to cyclic carbon chains that include at least one unsaturated triple bond. The cyclic portions of the carbon chains may include one ring or two or more fused rings.

As used herein, alkylenedioxy means an —O-alkyl-O— group in which the alkyl group is as previously described. A replacement analog of alkylenedioxy means an alkylenedioxy in which one or both of the oxygen atoms is replaced by a similar behaving atom or group of atoms such as, S, N, NH, Se. An exemplary replacement alkylenedioxy group is ethylenebis(sulfandiyl). Alkylenethioxyoxy is —S-alkyl-O—, —O-alkyl-S— and alkylenedithioxy is —S-alkyl-S—.

As used herein, heteroaryl means an aromatic monocyclic or fused ring system in which one or more of the carbon atoms in the ring system is(are) replaced by an element(s) other than carbon, for example nitrogen, oxygen or sulfur. Preferred cyclic groups contain one or two fused rings and include from about 3 to about 7 members in each ring. Similar to "aryl groups", the heteroaryl groups may be unsubstituted or substituted by one or more substituents. Exemplary heteroaryl groups include pyrazinyl, pyrazolyl, tetrazolyl, furanyl, (2- or 3-)thienyl, (2-,3- or 4-)pyridyl, imidazoyl, pyrimidinyl, isoxazolyl, thiazolyl, isothiazolyl, quinolinyl, indolyl, isoquinolinyl, oxazolyl and 2,1,3-oxadiazolyl. Preferred heteroaryl groups include 5 to 6-membered nitrogen-containing rings, such as pyrimidinyl.

As used herein, alkoxycarbonyl means an alkyl-O—CO— group. Exemplary alkoxycarbonyl groups include methoxy- and ethoxycarbonyl.

As used herein, carbamoyl means —CONH$_2$. As with all groups described herein, these groups may be unsubstituted or substituted. Substituted carbamoyl includes groups such as —CONY$^2$Y$^3$ in which Y$^2$ and Y$^3$ are independently hydrogen, alkyl, cyano(loweralkyl), aralkyl, heteroaralkyl, carboxy(loweralkyl), carboxy(aryl substituted loweralkyl), carboxy(carboxy substituted loweralkyl), carboxy(hydroxy substituted loweralkyl), carboxy(heteroaryl substituted loweralkyl), carbamoyl(loweralkyl), alkoxycarbonyl (loweralkyl) or alkoxycarbonyl(aryl substituted loweralkyl), provided that only one of Y$^2$ and Y$^3$ may be hydrogen and when one of Y$^2$ and Y$^3$ is carboxy(loweralkyl), carboxy(aryl substituted loweralkyl), carbamoyl(loweralkyl), alkoxycarbonyl(loweralkyl) or alkoxycarbonyl(aryl substituted loweralkyl) then the other of Y$^2$ and Y$^3$ is hydrogen or alkyl. Preferred for Y$^2$ and Y$^3$ are independently hydrogen, alkyl, cyano(loweralkyl), aryalkyl, heteroaralkyl, carboxy (loweralkyl), carboxy(aryl substituted loweralkyl) and carbamoyl(loweralkyl).

As used herein, any corresponding N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), N-(4,5-dimethyl-3-isoxazolyl) derivative thereof refers to compounds in which Ar$^2$ is the same as the compound specifically set forth, but Ar$^1$ is N-(4-halo-3-methyl-5-isoxazolyl), N-(4-halo-5-methyl-3-isoxazolyl), N-(3,4-dimethyl-5-isoxazolyl), N-(4-halo-5-methyl-3-isoxazolyl), N-(4-halo-3-methyl-5-isoxazolyl), or N-(4,5-dimethyl-3-isoxazolyl) in which halo is any halide, preferably Cl or Br.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942–944).

A. Compounds for Use in Treating Endothelin-mediated Diseases

Compounds and methods for treating endothelin-mediated diseases using the compounds of formula I are provided. In particular, the compounds provided herein are aryl-substituted thienyl, furanyl, or pyrrolyl sulfonamides, where the aryl group is tetra-, penta- or hexasubstituted, preferably pentasubstituted. Particularly preferred sulfonamides are N-isoxazolyl thiophene sulfonamides wherein the thiophene is substituted with an aryl group which has only one or two hydrogen substituents. If the aryl group is tetrasubstituted, it will preferably be substituted at the 2, 4 and 6 positions and one of these substituents will be a polar group, such as hydroxyl, carboxyl and carboxamide. If the aryl group is substituted at the 2, 4 and 6 positions with nonpolar groups, such as alkyl groups, more specifically methyl groups, then the aryl group will preferably be penta- or hexasubstituted. In pentasubstituted aryl groups, the fifth substituent will be at the 3 position and will preferably be a polar group, such as hydroxyl, carboxyl and carboxamide.

The compounds described herein in this latter group good bioavailability, relatively long in vivo half-life, and good efficacy in in vivo animal models and other suitable models.

The sulfonamides have formula I:

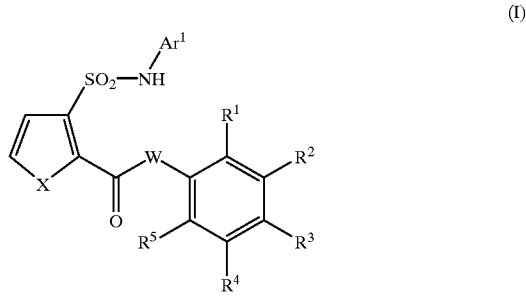

or the corresponding thiophene-2-sulfonamides as defined above, where Ar$^1$ is a substituted or unsubstituted monocyclic or polycyclic, preferably a monocyclic or fused bicyclic, aryl group with one or more substituents, selected from, for example, H, NH$_2$, halide, pseudohalide, alkyl, alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceeding groups, and straight or branched chains of from about 1 up to about 10–12 carbons, preferably, 1 to about 5 or 6 carbons. The substituents are preferably H, NH$_2$, halide, CH$_3$, CH$_3$O or another aromatic group. In particular, Ar$^1$ is a five or six membered substituted or unsubstituted aromatic or heteroaromatic ring or a fused bicyclic substituted or unsubstituted aromatic or heteroaromatic ring, preferably 3- or 5-isoxazolyl, benzo-1,2, 7-thiadiazol-4-yl, 2-pyrazinyl or benzo-1,2,7-oxadiazol-4-yl;

X is S, O or NR$^1$, preferably S;

R$^1$–R$^5$ are as defined above, and

R$^6$ is H, or substituted or unsubstituted alkyl or aryl, preferably H or substituted or unsubstituted lower alkyl, more preferably H, methyl or carboxymethyl.

In all embodiments herein, Ar$^1$ is preferably an isoxazolyl of formula:

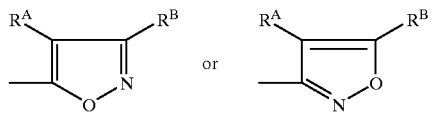

in which

R$^A$ and R$^B$ are either (i), (ii) or (iii) as follows:
(i) R$^A$ and R$^B$ are each independently selected from H, NH$_2$, NO$_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, substituted or unsubstituted ureido, in which the alkyl, alkenyl and alkynyl portions contain from 1 up to about 14 carbon atoms and are either straight or branched chains or cyclic, and the aryl portions contain from about 4 to about 16 carbons, except that $R^2$ is not halide or pseudohalide; or, (ii) $R^A$ and $R^B$ together form —$(CH_2)_n$—, where n is 3 to 6; or, (iii) $R^A$ and $R^B$ together form 1,3-butadienyl.

In preferred embodiments herein, $R^A$ and $R^B$ are each selected independently from among alkyl, lower alkenyl, lower alkynyl, lower haloalkyl, halide, pseudohalide or H, except that $R^B$ is not halide.

In one embodiment, the sulfonamides have formula II:

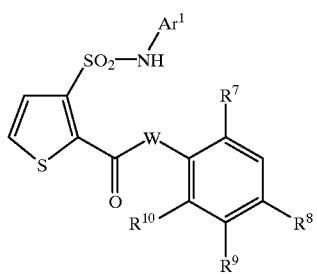

(II)

or the corresponding thiophene-2-sulfonamides as defined above.

$Ar^1$ is a substituted or unsubstituted monocyclic or polycyclic, preferably a monocyclic or fused bicyclic, aryl group with one or more substituents, selected from, for example, H, $NH_2$, halide, pseudohalide, alkyl, alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions are unsubstituted or substituted with any of the preceeding groups, and straight or branched chains of from about 1 up to about 10–12 carbons, preferably, 1 to about 5 or 6 carbons. The substituents are preferably H, $NH_2$, halide, $CH_3$, $CH_3O$ or another aromatic group. In particular, $Ar^2$ is a five or six membered substituted or unsubstituted aromatic or heteroaromatic ring or a fused bicyclic substituted or unsubstituted aromatic or heteroaromatic ring, preferably 3- or 5-isoxazolyl, benzo-1,2,7-thiadiazol-4-yl, 2-pyrazinyl or benzo-1,2,7-oxadiazol-4-yl, more preferably 4-chloro-3-methyl-5-isoxazolyl or 4-chloro-5-methyl-3-isoxazolyl; W is —NH—, =$NCOR^{16}$, =$NCO_2R^{16}$, —NHC($R^{12}$)($R^{16}$)— or is —$CH_2$— when $R^9$ is hydroxyl.

$R^9$ is selected from the group consisting of substituted and unsubstituted alkyl, hydroxyl, substituted and unsubstituted alkoxy, $OC(O)R^{16}$, $OCO_2R^{16}$, $NR^{12}R^{16}$ and $S(O)_nR^{16}$ in which n is 0–2; preferably alkoxycarbonylalkyl, carboxyalkyl, dialkylaminoalkyl, alkylsulfonylamino and aminosulfonyl.

The phenyl substituents designated in this formula $R^7$, $R^8$ and $R^{10}$ are $R^1$, $R^3$, and $R^5$, respectively. $R^7$, $R^3$ and $R^{10}$, which are preferably alkyl, haloalkyl, polyhaloalkyl, alkenyl containing 1 to 2 double bonds, alkynyl containing 1 to 2 triple bonds, cycloalkyl, cycloalkylalkyl, aryl, heteroaryl, arylalkyl, or heteroarylalkyl, more preferably lower alkyl, lower alkenyl, lower alkynyl, or aryl, most preferably methyl.

In more preferred embodiments, the sulfonamides of formula II are those wherein $R^7$, $R^8$, $R^9$ and $R^{10}$ do not contain cyano groups and W is not —$CH_2$—. These compounds are preferred due to their improved toxicological profiles relative to other compounds of formula II.

In preferred embodiments of the compounds of formula II, $Ar^1$ is 3- or 5-isoxazolyl, benzo-1,2,7-thiadiazol-4-yl, 2-pyrazinyl or benzo-1,2,7-oxadiazol-4-yl, more preferably 3-methoxy-2-pyrazinyl, 3,4-dimethyl-5-isoxazolyl, 4-chloro-3methyl-5-isoxazolyl or 4-chloro-5-methyl-3-isoxazolyl; W is —NH—, =$NCO_2R^{16}$, or is —$CH_2$— when $R^9$ is hydroxyl; $R^7$, $R^8$ and $R^{10}$ are methyl; and $R^9$ is selected from the group consisting of substituted and unsubstituted alkyl, hydroxyl, substituted and unsubstituted alkoxy, $OC(O)R^{16}$, $OCO_2R^{16}$, $NR^{12}R^{16}$ and $S(O)_nR^{16}$ in which n is 0–2; preferably alkoxycarbonylalkyl, carboxyalkyl, dialkylaminoalkyl, alkylsulfonylamino and aminosulfonyl.

$R^9$ is, in certain of these embodiments, methoxy, methoxycarbonylmethoxy, 2-(2-methoxyethoxy)ethoxyacetoxy, 2-hydroxyethoxy, N,N-dimethylthiocarbonyloxy, N,N-dimethylthiocarbonyloxymethyl, dimethylamino, pyrrolidinyl, acetoxy, hydroxyl, carboxyl, cyanomethyl, acetoxymethyl, hydroxymethyl, carboxylmethyl, methanesulfonylamino, N,N-dimethylalminomethyl, $SO_2NH_2$, or methoxycarbonylmethyl.

$R^9$, in more preferred embodiments, does not contain a cyano group and is, for example, methoxy, methoxycarbonylmethoxy, 2-(2-methoxyethoxy)ethoxyacetoxy, 2-hydroxyethoxy, N,N-dimethylthiocarbonyloxy, N,N-dimethylthiocarbonyloxymethyl, dimethylamino, pyrrolidinyl, acetoxymethyl, methoxycarbonylmethyl, hydroxy or acetoxy.

Among the compounds of formula II are:
N-(4-chloro-3-methyl-5-isoxazolyl)-2-(3-carboxylmethyl-2,4,6-trimethylphenylaminocarbonyl)thiophene-3-sulfonamide;
N-(4-chloro-3-methyl-5-isoxazolyl)-2-(3-acetoxy-2,4,6-trimethylphenylaminocarbonyl)thiophene-3-sulfonamide;
N-(4-chloro-3-methyl-5-isoxazolyl)-2-(3-pyrrolidinyl-2,4,6-trimethylphenylaminocarbonyl)thiophene-3-sulfonamide;
N-(4-chloro-3-methyl-5-isoxazolyl)-2-(3-dimethylamino-2,4,6-trimethylphenylaminocarbonyl)thiophene-3-sulfonamide;
N-(4-chloro-3-methyl-5-isoxazolyl)-2-(3-(N,N-dimethylthiocarbonyloxymethyl-2,4,6-trimethylphenylaminocarbonyl)thiophene-3-sulfonamide;
N-(4-chloro-3-methyl-5-isoxazolyl)-2-(3-(N,N-dimethylthiocarbonyloxy)-2,4,6-trimethylphenylaminocarbonyl)thiophene-3-sulfonamide;
N-(4-chloro-3-methyl-5-isoxazolyl)-2-(3-(2-hydroxyethoxy)-2,4,6-trimethylphenylaminocarbonyl)thiophene-3-sulfonamide;
N-(4-chloro-3-methyl-5-isoxazolyl)-2-(3-(2-(2-methoxyethoxy)ethoxy)acetoxy-2,4,6-trimethylphenylaminocarbonyl)thiophene-3-sulfonamide;
N-(4-chloro-3-methyl-5-isoxazolyl)-2-(3-methoxycarbonylmethoxy-2,4,6-trimethylphenylaminocarbonyl)thiophene-3-sulfonamide;

N-(4-chloro-3-methyl-5-isoxazolyl)-2-(3-methoxy-2,4,6-trimethylphenylaminocarbonyl)thiophene-3-sulfonamide;

N-(4-chloro-3-methyl-5-isoxazolyl)-2-(3-methoxycarbonylmethyl-2,4,6-trimethylphenylaminocarbonyl)thiophene-3-sulfonamide;

N-(4-chloro-3-methyl-5-isoxazolyl)-2-(3-acetoxymethyl-2,4,6-trimethylphenylaminocarbonyl)thiophene-3-sulfonamide;

N-(4-chloro-3-methyl-5-isoxazolyl)-2-(3-hydroxy-2,4,6-trimethylphenylaminocarbonyl)thiophene-3-sulfonamide;

N-(4-chloro-3-methyl-5-isoxazolyl)-2-(3-dimethylaminomethyl-2,4,6-trimethylphenylaminocarbonyl)thiophene-3-sulfonamide;

N-(4-chloro-3-methyl-5-isoxazolyl)-2-(3-methanesulfonylamino-2,4,6-trimethylphenylaminocarbonyl)thiophene-3-sulfonamide;

N-(4-chloro-3-methyl-5-isoxazolyl)-2-(3-sulfamoyl-2,4,6-trimethylphenylaminocarbonyl)thiophene-3-sulfonamide;

N-(4-chloro-5-methyl-3-isoxazolyl)-2-(3-cyanomethyl-2,4,6-trimethylphenylaminocarbonyl)thiophene-3-sulfonamide;

N-(4-chloro-5-methyl-3-isoxazolyl)-2-(3-methoxycarbonylmethyl-2,4,6-trimethylphenylaminocarbonyl)thiophene-3-sulfonamide;

N-(4-chloro-5-methyl-3-isoxazolyl)-2-(3-carboxylmethyl-2,4,6-trimethylphenylaminocarbonyl)thiophene-3-sulfonamide;

N-(4-chloro-5-methyl-3-isoxazolyl)-2-(3-acetoxymethyl-2,4,6-trimethylphenylaminocarbonyl)thiophene-3-sulfonamide;

N-(4-chloro-5-methyl-3-isoxazolyl)-2-(3-hydroxymethyl-2,4,6-trimethylphenylaminocarbonyl)thiophene-3-sulfonamide;

N-(4-chloro-5-methyl-3-isoxazolyl)-2-(3-dimethylaminomethyl-2,4,6-trimethylphenylaminocarbonyl)thiophene-3-sulfonamide;

N-(4-chloro-5-methyl-3-isoxazolyl)-2-(3-methanesulfonylamino-2,4,6-trimethylphenylaminocarbonyl)thiophene-3-sulfonamide;

N-(4-chloro-5-methyl-3-isoxazolyl)-2-(3-hydroxy-2,4,6-trimethylphenylaminocarbonyl)thiophene-3-sulfonamide;

N-(4-chloro-5-methyl-3-isoxazolyl)-2-(3-carboxy-2,4,6-trimethylphenylaminocarbonyl)thiophene-3-sulfonamide;

N-(4-chloro-5-methyl-3-isoxazolyl)-2-(3-cyano-2,4,6-trimethylphenylaminocarbonyl)thiophene-3-sulfonamide;

N-(4-chloro-5-methyl-3-isoxazolyl)-2-(3-sulfamoyl-2,4,6-trimethylphenylaminocarbonyl)thiophen-3-sulfonamide;

N-(3,4-dimethyl-5-isoxazolyl)-2-(3-cyanomethyl-2,4,6-trimethylphenylaminocarbonyl)thiophene-3-sulfonamide;

N-(3,4-dimethyl-5-isoxazolyl)-2-(3-methoxycarbonylmethyl-2,4,6-trimethylphenylaminocarbonyl)thiophene-3-sulfonamide;

N-(3,4-dimethyl-5-isoxazolyl)-2-(3-carboxylmethyl-2,4,6-trimethylphenylaminocarbonyl)thiophene-3-sulfonamide;

N-(3,4-dimethyl-5-isoxazolyl)-2-(3-acetoxymethyl-2,4,6-trimethylphenylaminocarbonyl)thiophene-3-sulfonamide;

N-(3,4-dimethyl-5-isoxazolyl)-2-(3-hydroxymethyl-2,4,6-trimethylphenylaminocarbonyl)thiophene-3-sulfonamide;

N-(3,4-dimethyl-5-isoxazolyl)-2-(3-dimethylaminomethyl-2,4,6-trimethylphenylaminocarbonyl)thiophene-3-sulfonamide;

N-(3,4-dimethyl-5-isoxazolyl)-2-(3-methanesulfonylamino-2,4,6-trimethylphenylaminocarbonyl)thiophene-3-sulfonamide;

N-(3,4-dimethyl-5-isoxazolyl)-2-(3-hydroxy-2,4,6-trimethylphenylaminocarbonyl)thiophene-3-sulfonamide;

N-(3,4-dimethyl-5-isoxazolyl)-2-(3-carboxy-2,4,6-trimethylphenylaminocarbonyl)thiophene-3-sulfonamide;

N-(3,4-dimethyl-5-isoxazolyl)-2-(3-cyano-2,4,6-trimethylphenylaminocarbonyl)thiophene-3-sulfonamide;

N-(3,4-dimethyl-5-isoxazolyl)-2-(3-sulfamoyl-2,4,6-trimethylphenylaminocarbonyl)thiophene-3-sulfonamide;

N-(benzo-1,2,7-thiadiazol-4-yl)-2-(3-cyanomethyl-2,4,6-trimethylphenylaminocarbonyl)thiophene-3-sulfonamide;

N-(benzo-1,2,7-thiadiazol-4-yl)-2-(3-methoxycarbonylmethyl-2,4,6-trimethylphenylaminocarbonyl)thiophene-3-sulfonamide;

N-(benzo-1,2,7-thiadiazol-4-yl)-2-(3-carboxylmethyl-2,4,6-trimethylphenylaminocarbonyl)thiophene-3-sulfonamide;

N-(benzo-1,2,7-thiadiazol-4-yl)-2-(3-acetoxymethyl-2,4,6-trimethylphenylaminocarbonyl)thiophene-3-sulfonamide;

N-(benzo-1,2,7-thiadiazol-4-yl)-2-(3-hydroxymethyl-2,4,6-trimethylphenylaminocarbonyl)thiophene-3-sulfonamide;

N-(benzo-1,2,7-thiadiazol-4-yl)-2-(3-dimethylaminomethyl-2,4,6-trimethylphenylaminocarbonyl)thiophene-3-sulfonamide;

N-(benzo-1,2,7-thiadiazol-4-yl)-2-(3-methanesulfonylamino-2,4,6-trimethylphenylaminocarbonyl)thiophene-3-sulfonamide;

N-(benzo-1,2,7-thiadiazol-4-yl)-2-(3-hydroxy-2,4,6-trimethylphenylaminocarbonyl)thiophene-3-sulfonamide;

N-(benzo-1,2,7-thiadiazol-4-yl)-2-(3-carboxy-2,4,6-trimethylphenylaminocarbonyl)thiophene-3-sulfonamide;

N-(benzo-1,2,7-thiadiazol-4-yl)-2-(3-cyano-2,4,6-trimethylphenylaminocarbonyl)thiophene-3-sulfonamide;

N-(benzo-1,2,7-thiadiazol-4-yl)-2-(3-sulfamoyl-2,4,6-trimethylphenylaminocarbonyl)thiophene-3-sulfonamide;

N-(3-methoxy-2-pyrazinyl)-2-(3-cyanomethyl-2,4,6-trimethylphenylaminocarbonyl)thiophene-3-sulfonamide;

N-(3-methoxy-2-pyrazinyl)-2-(3-methoxycarbonylmethyl-2,4,6-trimethylphenylaminocarbonyl)thiophene-3-sulfonamide;

N-(3-methoxy-2-pyrazinyl)-2-(3-carboxylmethyl-2,4,6-trimethylphenylaminocarbonyl)thiophene-3-sulfonamide;
N-(3-methoxy-2-pyrazinyl)-2-(3-acetoxymethyl-2,4,6-trimethylphenylaminocarbonyl)thiophene-3-sulfonamide;
N-(3-methoxy-2-pyrazinyl)-2-(3-hydroxymethyl-2,4,6-trimethylphenylaminocarbonyl)thiophene-3-sulfonamide;
N-(3-methoxy-2-pyrazinyl)-2-(3-dimethylaminomethyl-2,4,6-trimethylphenylaminocarbonyl)thiophene-3-sulfonamide;
N-(3-methoxy-2-pyrazinyl)-2-(3-methanesulfonylamino-2,4,6-trimethylphenylaminocarbonyl)thiophene-3-sulfonamide;
N-(3-methoxy-2-pyrazinyl)-2-(3-hydroxy-2,4,6-trimethylphenylaminocarbonyl)thiophene-3-sulfonamide;
N-(3-methoxy-2-pyrazinyl)-2-(3-carboxy-2,4,6-trimethylphenylaminocarbonyl)thiophene-3-sulfonamide;
N-(3-methoxy-2-pyrazinyl)-2-(3-cyano-2,4,6-trimethylphenylaminocarbonyl)thiophene-3-sulfonamide;
N-(3-methoxy-2-pyrazinyl)-2-(3-sulfamoyl-2,4,6-trimethylphenylaminocarbonyl)thiophene-3-sulfonamide;
N-(4-chloro-3-methyl-5-isoxazolyl)-2-(1-methyl-1-phenyl-1-ethylaminocarbonyl)thiophene-3-sulfonamide;
N-(4-chloro-3-methyl-5-isoxazolyl)-2-((R)-1-phenyl-1-ethylaminocarbonyl)thiophene-3-sulfonamide; and
N-(4-chloro-3-methyl-5-isoxazolyl)-2-((S)-1-phenyl-1-ethylaminocarbonyl)thiophene-3-sulfonamide.

Among the more preferred compounds of formula II are:
N-(4-chloro-3-methyl-5-isoxazolyl)-2-(3-methoxycarbonylmethyl-2,4,6-trimethylphenylaminocarbonyl)thiophene-3-sulfonamide;
N-(4-chloro-3-methyl-5-isoxazolyl)-2-(3-acetoxymethyl-2,4,6-trimethylphenylaminocarbonyl)thiophene-3-sulfonamide;
N-(4-chloro-3-methyl-5-isoxazolyl)-2-(3-hydroxy-2,4,6-trimethylphenylaminocarbonyl)thiophene-3-sulfonamide;
N-(4-chloro-3-methyl-5-isoxazolyl)-2-(3-methoxy-2,4,6-trimethylphenylaminocarbonyl)thiophene-3-sulfonamide;
N-(4-chloro-3-methyl-5-isoxazolyl)-2-(3-methoxycarbonylmethoxy-2,4,6-trimethylphenylaminocarbonyl)thiophene-3-sulfonamide;
N-(4-chloro-3-methyl-5-isoxazolyl)-2-(3-(2-(2-methoxyethoxy)ethoxy)acetoxy-2,4,6-trimethylphenylaminocarbonyl)thiophene-3-sulfonamide;
N-(4-chloro-3-methyl-5-isoxazolyl)-2-(3-(2-hydroxyethoxy)-2,4,6-trimethylphenylaminocarbonyl)thiophene-3-sulfonamide;
N-(4-chloro-3-methyl-5-isoxazolyl)-2-(3-(N,N-dimethylthiocarbonyloxy)-2,4,6-trimethylphenylaminocarbonyl)thiophene-3-sulfonamide;
N-(4-chloro-3-methyl-5-isoxazolyl)-2-(3-(N,N-dimethylthiocarbonyloxymethyl-2,4,6-trimethylphenylaminocarbonyl)thiophene-3-sulfonamide;
N-(4-chloro-3-methyl-5-isoxazolyl)-2-(3-dimethylamino-2,4,6-trimethylphenylaminocarbonyl)thiophene-3-sulfonamide;
N-(4-chloro-3-methyl-5-isoxazolyl)-2-(3-pyrrolidinyl-2,4,6-trimethylphenylaminocarbonyl)thiophene-3-sulfonamide; and
N-(4-chloro-3-methyl-5-isoxazolyl)-2-(3-acetoxy-2,4,6-trimethylphenylaminocarbonyl)thiophene-3-sulfonamide.

In another embodiment, the sulfonamides have formula III:

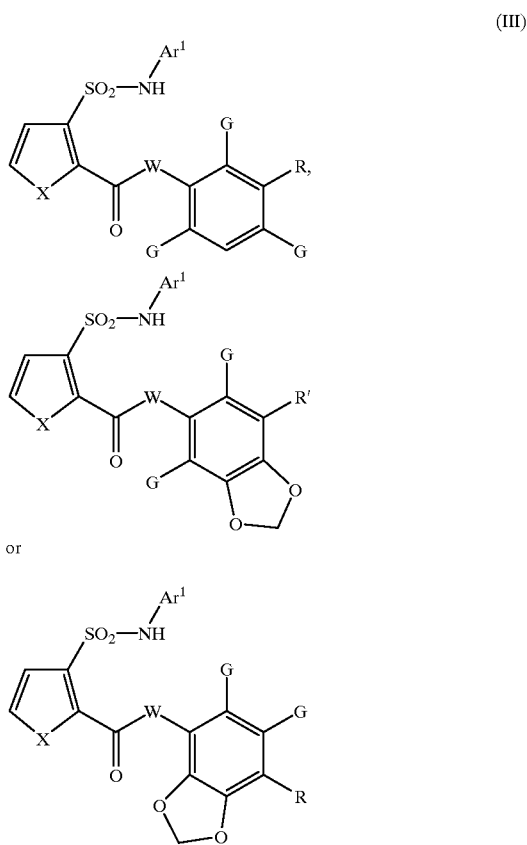

(III)

or the corresponding thiophene-2-sulfonamides as defined above, where:

$Ar^1$ is a substituted or unsubstituted monocyclic or polycyclic, preferably a monocyclic or fused bicyclic, aryl group with one or more substituents, selected from, for example, H, $NH_2$, halide, pseudohalide, alkyl, alkylcarbonyl, formyl, an aromatic or heteroaromatic group, alkoxyalkyl, alkylamino, alkylthio, arylcarbonyl, aryloxy, arylamino, arylthio, haloalkyl, haloaryl, carbonyl, in which the aryl and alkyl portions, are unsubstituted or substituted with any of the preceeding groups, and straight or branched chains of from about 1 up to about 10–12 carbons, preferably, 1 to about 5 or 6 carbons. The substituents are preferably H, $NH_2$, halide, $CH_3$, $CH_3O$ or another aromatic group. In particular, $Ar^1$ is a five or six membered substituted or unsubstituted aromatic or heteroaromatic ring or a fused bicyclic substituted or unsubstituted aromatic or heteroaromatic ring, preferably 3- or 5-isoxazolyl, benzo-1,2,7-thiadiazol-4-yl, 2-pyrazinyl or benzo-1,2,7-oxadiazol-4-yl;

X is S, O or $NR^{11}$;

each G and R, which are selected from among the $R^1$–$R^5$ as defined above, are preferably independently selected from lower alkyl, CN, $-(CH_2)_x C(O)(CH_2)_x$, —(CH$_2$)$_x$, (CH$_2$)$_x$N-lower alkyl, —(CH$_2$)$_x$C(O)NH$_2$, a D-, L- or racemic amino acid, a primary or secondary amide, O-glycoside, a hexose or ribose, —S(O)$_2$NH$_2$, hydroxy, alkoxy, alkoxycarbonyl, acetoxyalkyl, —(CH$_2$)$_x$COOH; —(CH$_2$)$_x$COOH—, CO$_2$-lower alkyl, CN, heteroaryl, —COC(O)(CH$_2$)$_x$CH$_3$, —(CH$_2$)$_x$N(CH$_3$)$_2$, a sulfonyl chloride, S(O)$_2$NHR$^{50}$, alkylaryl, alkylheteroaryl, C(O)NHR$^{50}$, —(CH$_2$)$_x$OH, —C(O)N(H)N(H)M';

R$^{50}$ is hydrogen, lower alkyl, lower alkoxy;

M' is H or R$^{50}$;

R' is selected from hydrogen, G and R;

W is =C(halo)$_2$, =N(H), —(CH$_2$)$_x$—, =N(lower alkyl), —C(O)—, =C(lower alkyl)$_2$, and x is 0–3.

In particular, in these embodiments compounds where: R, G and R' are selected where the amino acid is L-Asp or L-Glu; the hexose is D-mannose, the heteroaryl is triazolyl, and X is S are of interest. Also of interest are compounds in which:

W is =CH$_2$, =NH, =NCH$_3$, =NCH$_2$CH$_3$, =C(CH$_3$)$_2$ or CF$_2$; and

G is —CH$_3$, —CN, —COCH$_3$, —CH$_2$CH$_3$, —(CH$_2$)$_x$CO$_2$H are of interest.

Among these compounds are:

N-(4-chloro-3-methyl-5-isoxazolyl)-2-(3-methoxycarbonyl-2,4,6-trimethylphenylaminocarbonyl)thiophene-3-sulfonamide;

N$^2$-(3-cyanomethyl-2,4,6-trimethylphenyl)-3-(4-chloro-3-methyl-5-isoxazolylsulfamoyl)-2-thiophenecarboxamide;

methyl-2-(3-(3-(4-chloro-3-methyl-5-isoxazolylsulfamoyl)-2-thienylcarboxamido)-2,4,6-trimethylphenyl)acetate;

2-(3-(3-(4-chloro-3-methyl-5-isoxazolylsulfamoyl)-2-thienylcarboxamido)-2,4,6-trimethylphenyl)acetic acid;

N$^2$-(3-acetyloxymethyl-2,4,6-trimethylphenyl)-3-(4-chloro-3-methyl-5-isoxazolylsulfamoyl)-2-thiophenecarboxamide;

N$^2$-(3-hydroxymethyl-2,4,6-trimethylphenyl)-3-(4-chloro-3-methyl-5-isoxazolylsulfamoyl)-2-thiophenecarboxamide;

N$^2$-(3-dimethylaminomethyl-2,4,6-trimethylphenyl)-3-(4-chloro-3-methyl-5-isoxazolylsulfamoyl)-2-thiophenecarboxamide trifluoroacetate;

N$^2$-(3-(4,5-dihydro-1,3-oxazol-2-yl)-2,4,6-trimethylphenyl)-3-(4-chloro-3-methyl-5-isoxazolylsulfamoyl)-2-thiophenecarboxamide;

3-(3-(4-chloro-3-methyl-5-isoxazolylsulfamoyl)-2-thienylcarboxamide)-2,4,6-trimethylbenzoic acid;

N-[3-(3-(4-chloro-3-methyl-5-isoxazolylsulfamoyl)-2-thienylcarboxamide)-2,4,6-trimethylbenzoyl]glutamic acid;

N-[3-(3-(4-chloro-3-methyl-5-isoxazolylsulfamoyl)-2-thienylcarboxamido)-2,4,6-trimethylbenzoyl]aspartic acid;

N-[2-(3-(3-(4-chloro-3-methyl-5-isoxazolylsulfamoyl)-2-thienylcarboxamido)-2,4,6-trimethylphenyl)acetyl] glutamic acid;

N-[2-(3-(3-(4-chloro-3-methyl-5-isoxazolylsulfamoyl)-2-thienylcarboxamido)-2,4,6-trimethylphenyl)acetyl] aspartic acid;

N$^2$-(3-cyano-2,4,6-trimethylphenyl)-3-(4-chloro-3-methyl-5-isoxazolylsulfamoyl)-2-thiophenecarboxamide;

2-(3-(3-(4-chloro-3-methyl-5-isoxazolylsulfamoyl)-2-thienylcarboxamido)-2,4,6-trimethylphenoxy)acetic acid;

N$^2$-(3-alkylsulfonamido-2,4,6-trimethylphenyl)-3-(4-chloro-3methyl-5-isoxazolylsulfamoyl)-2-thiophenecarboxamide;

N$^2$-(3-arylsulfonamido-2,4,6-trimethylphenyl)-3-(4-chloro-3-methyl-5-isoxazolylsulfamoyl)-2-thiophenecarboxamide;

N$^2$-(3-sulfamoyl-2,4,6-trimethylphenyl)-3-(4-chloro-3-methyl-5-isoxazolylsulfamoyl)-2-thiophenecarboxamide;

N$^2$-(3-alkylsulfamoyl-2,4,6-trimethylphenyl)-3-(4-chloro-3-methyl-5-isoxazolylsulfamoyl)-2-thiophenecarboxamide;

N$^2$-(3-arylsulfamoyl-2,4,6-trimethylphenyl)-3-(4-chloro-3-methyl-5-isoxazolylsulfamoyl)-2-thiophenecarboxamide;

N$^2$-(3-(1H-1,2,3,4-tetraazol-5-ylmethyl)-2,4,6-trimethylphenyl)-3-(4-chloro-3-methyl-5-isoxazolylsulfamoyl)-2-thiophenecarboxamide;

N$^2$-(3-(2-pyridylmethyl)-2,4,6-trimethylphenyl)-3-(4-chloro-3-methyl-5-isoxazolylsulfamoyl)-2-thiophenecarboxamide;

N$^2$-(3-hydrazinocarbonyl-2,4,6-trimethylphenyl)-3-(4-chloro-3-methyl-5-isoxazolylsulfamoyl)-2-thiophenecarboxamide;

N$^2$-(3-aminomethyl-2,4,6-trimethylphenyl)-3-(4-chloro-3-methyl-5-isoxazolylsulfamoyl)-2-thiophenecarboxamide;

N$^2$-(3-(a-D-mannopyranosyloxymethyl)-2,4,6-trimethylphenyl)-3-(4-chloro-3-methyl-5-isoxazolylsulfamoyl)-2-thiophenecarboxamide;

5-(3-(4-chloro-3-methyl-5-isoxazolylsulfamoyl)-2-thienylcarboxamido)-4-cyano-6-methylbenzo[d][1,3] dioxole;

5-(3-(4-chloro-3-methyl-5-isoxazolylsulfamoyl)-2-thienylcarboxamido)-6-cyano-4-methylbenzo[d][1,3] dioxole;

2-(5-(3-(4-chloro-3-methyl-5-isoxazolylsulfamoyl)-2-thienylcarboxamido)-4-methylbenzo[d][1,3]dioxole)-6-acetic acid;

5-(3-(4-chloro-3-methyl-5-isoxazolylsulfamoyl)-2-thienylcarboxamido)-4-acetyl-6-methylbenzo[d][1,3] dioxole;

5-(3-(4-chloro-3-methyl-5-isoxazolylsulfamoyl)-2-thienylcarboxamido)-6-acetyl-4-methylbenzo[d][1,3] dioxole;

5-(3-(4-chloro-3-methyl-5-isoxazolylsulfamoyl)-2-thienylcarboxamido)-7-cyano-4,6-dimethylbenzo[d][1,3] dioxole;

6-(3-(4-chloro-3-methyl-5-isoxazolylsulfamoyl)-2-thienylcarboxamido)-5,7-dimethylbenzo[d][1,3]dioxole-4-carboxylic acid;

7-(3-(4-chloro-3-methyl-5-isoxazolylsulfamoyl)-2-thienylcarboxamido)-5,6-dimethylbenzo[d][1,3]dioxole-4-carboxylic acid;

7-(3-(4-chloro-3-methyl-5-isoxazolylsulfamoyl)-2-thienylcarboxamido)-4-cyano-5,6-dimethylbenzo[d][1,3] dioxole;

7-(3-(4-chloro-3-methyl-5-isoxazolylsulfamoyl)-2-thienylcarboxamido)-4-acetyl-5,6-dimethylbenzo[d][1,3] dioxole;

7-(3-(4-chloro-3-methyl-5-isoxazolylsulfamoyl)-2-thienylcarboxamido)-4-carboxamido-5,6-dimethylbenzo [d][1,3]dioxole;

7-(3-(4-chloro-3-methyl-5-isoxazolylsulfamoyl)-2-thienylcarboxamido)-4-aminomethyl-5,6-dimethylbenzo [d][1,3]dioxole; and 7-(3-(4-chloro-3-methyl-5-isoxazolylsulfamoyl)-2-thienylcarboxamido)-4-dimethylaminomethyl-5,6-dimethylbenzo[d][1,3]dioxole;

N-(4-chloro-3-methyl-5-isoxazolyl)-2-(3-cyanomethyl-2,4,6-trimethylphenylaminocarbonyl)thiophene-3-sulfonamide;

N-(4-chloro-3-methyl-5-isoxazolyl)-2-(3-carboxymethyl-2,4,6-trimethylphenylaminocarbonyl)thiophene-3-sulfonamide;

N-(4-chloro-3-methyl-5-isoxazolyl)-2-(3-acetoxymethyl-2,4,6-trimethylphenylaminocarbonyl)thiophene-3-sulfonamide; N-(4-chloro-3-methyl-5-isoxazolyl)-2-(3-hydroxymethyl-2,4,6-trimethylphenylaminocarbonyl)thiophene-3-sulfonamide; and N-(4-chloro-3-methyl-5-isoxazolyl)-2-(3-methoxycarbonyl-2,4,6-trimethylphenylaminocarbonyl)thiophene-3-sulfonamide.

In another embodiment, the sulfonamides have formula IV:

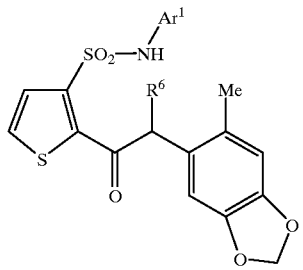

(IV)

or the corresponding thiophene-2-sulfonamides as defined above, $Ar^1$ is defined as above, except when $R^6$ is H, then $Ar^1$ is not 4-chloro-3-methyl-5-isoxazolyl, 4-chloro-5-methyl-3-isoxazolyl or 3,4-dimethyl-5-isoxazoly. $Ar^1$ is preferably benzo-1,2,7-oxadiazol-4-yl or 2-methoxy-3-pyrazinyl when $R^6$ is H; and $R^6$ is H, or substituted or unsubstituted alkyl or aryl, preferably H or substituted or unsubstituted lower alkyl, more preferably methyl or carboxymethyl.

In other embodiments of formula (IV), $Ar^1$ is preferably benzo-1,2,7-oxadiazol-4-yl or 2-methoxy-3-pyrazinyl when $R^6$ is H and $R^6$ is H, or substituted or unsubstituted alkyl or aryl, preferably H or substituted or unsubstituted lower alkyl, more preferably methyl or carboxymethyl.

Thus, preferred compounds of formula IV include:
N-(benzo-2,1,3-oxadiazol-5-yl-2-(2-methyl-4,5-methylenedioxyphenylacetyl)thiophene-3-sulfonamide;
N-(3-methoxy-2-pyrazinyl)-2-(2-methyl-4,5-methylenedioxyphenylacetyl)thiophene-3-sulfonamide;
N-(4-chloro-3-methyl-5-isoxazolyl)-2-(2-(2-methyl-4,5-methylenedioxyphenyl)propanoyl)thiophene-3-sulfonamide; and
N-(4-chloro-3-methyl-5-isoxazolyl)-2-(3-carboxyl-2-(2-methyl-4,5-methylenedioxyphenyl)propanoyl)thiophene-3-sulfonamide.

In another embodiment, the sulfonamides have formula V:

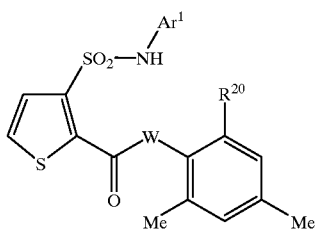

(V)

or the corresponding thiophene-2-sulfonamides as defined above.

$Ar^1$ is defined as above and is preferably 4-chloro-3-methyl-5-isoxazolyl; W is NH; and $R^{20}$ is selected from the group consisting of aryl, heteroaryl, heterocycle, OH, CN, $C(O)R^{16}$, $CO_2R^{16}$, SH, $S(O)_nR^{16}$ in which n is 0–2, a D, L or racemic amino acid, a ribose or hexose, an O-glycoside, a sulfonyl chloride, $—(CH_2)_xOH$, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocycle, aralkyl, aralkoxy, cycloalkyl, cycloalkenyl or cycloalkynyl; $R^{12}$ is selected from hydrogen, alkyl, alkenyl, alkynyl, aryl, alkylaryl, heterocycle, aralkyl, aralkoxy, cycloalkyl, cycloalkenyl, cycloalkynyl, $C(O)R^{17}$ and $S(O)_nR^{17}$ in which n is 0–2; $R^{17}$ is hydrogen, alkyl, alkenyl, alkynyl, aryl, alkylaryl, heterocycle, aralkyl, aralkoxy, cycloalkyl, cycloalkenyl or cycloalkynyl; each of $R^{12}$, $R^{15}$ and $R^{16}$ may be further substituted with the any of the groups set forth for Z; $R^{20}$ is preferably $CONH^2$, COOH, or phenyl.

Preferred embodiments of the compounds of formula V are those wherein $Ar^1$ is 4-chloro-3-methyl-5-isoxazolyl; W is NH; and $R^{20}$ is $CONH^2$, COOH, or phenyl.

Also of interest are any pharmaceutically-acceptable derivatives, including salts, esters, acids and bases, solvates, hydrates and prodrugs of the sulfonamides. Preferred are pharmaceutically-acceptable salts, particularly alkali metal salts, most preferably sodium salts.

Particularly preferred derivatives are salts of compounds described herein where W is alkylene, more particularly $CH_2$. Of these derivatives, the preferred salts are sodium salts, preferably sodium hydrogen phosphate or sodium salts, more preferably sodium salts.

In all embodiments, preferred substituents also can be determined by reference to Table 1, which sets forth exemplary compounds. Preferred compounds are those of Table 1 that have the highest activities, and preferred substituents are those on the compounds with the highest activities (activity at the lowest concentration).

TABLE 1

| COMPOUND | $ET_A$ ($\mu M$)* | $ET_B$ ($\mu M$)* |
|---|---|---|
| N-(3,4-dimethyl-5-isoxazolyl)-2-methylbenzo[b]thiophene-3-sulfonamide | 0.167 | 16.6 |
| N-(4-bromo-3-methyl-5-isoxazolyl)-2-(4-ethylbenzyl)benzo[b]thiophene-3-sulfonamide | 0.048† | 1.1† |
| N-(4-bromo-3-methyl-5-isoxazolyl)-2-[3,4-(methylenedioxy)benzyl]benzo[b]thiophene-3-sulfonamide | 0.0015 ± 0.0014<br>0.0074 ± 0.0011† | 0.324 ± 0.78<br>0.939 ± 0.262† |
| N-(4-bromo-3-methyl-5-isoxazolyl)-2-(3,4,5-trimethoxybenzyl)-benzo[b]thiophene-3-sulfonamide | 0.031† | 1.2† |
| N-(4-chloro-3-methyl-5-isoxazolyl)-2-[3,4-methylenedioxy)benzyl]benzo[b]thiophene-3-sulfonamide | 0.011 ± 0.005† | 0.936 ± 0.095† |
| N-(4-bromo-3-methyl-5-isoxazolyl)-2-(3,4-dimethoxybenzyl)benzo[b]thiophene-3-sulfonamide | 0.021 ± 0.017† | 2.94 ± 1.32† |

TABLE 1-continued

| COMPOUND | $ET_A$ (μM)* | $ET_B$ (μM)* |
|---|---|---|
| N-(4-bromo-3-methyl-5-isoxazolyl)-5-(benzo[b]thien-2-yl)thiophene-2-sulfonamide | 16† | 0.80† |
| N-(4-bromo-3-methyl-5-isoxazolyl)-2-(4-methoxybenzyl)benzo[b]thiophene-3-sulfonamide | 0.051† | 1.5† |
| N-(4-bromo-3-methyl-5-isoxozolyl)-2-(2-methoxybenzyl)-benzo[b]thiophene-3-sulfonamide | 0.19† | 2.2† |
| N-(3,4-dimethyl-5-isoxazolyl)-2-(4-chlorobenzyl)benzo[b]thiophene-3-sulfonamide | 0.21† | 4.7† |
| N-(4-chloro-3-methyl-5-isoxazolyl)-2-(4-dimethylaminobenzyl)benzo[b]thiophene-3-sulfonamide | 0.041†<br>0.014 | 1.3†<br>0.477 |
| N-(4-chloro-3-methyl-5-isoxazolyl)-2-ethylbenzo[b]furan-3-sulfonamide | 0.15† | 22† |
| N-(4-chloro-3-methyl-5-isoxazolyl)-2-phenylbenzo[b]thiophene sulfonamide | 0.932† | 46.8† |
| N-(4-chloro-3-methyl-5-isoxazolyl)-6-methoxy-2-[3,4-(methylenedioxy)benzyl]benzo[b]thiophene-3-sulfonamide | ~2$^{est†}$ | 2.39† |
| N-(4-chloro-5-methyl-3-isoxazolyl)-2-[3,4-(methylenedioxy)benzyl]benzo[b]thiophene-3-sulfonamide | 0.0055† | 0.364† |
| N-(4-chloro-3-methyl-5-isoxazolyl)-2-methoxycarbonylthiophene-3-sulfonamide | 0.631 | 53.2 |
| N-(3,4-dimethyl-5-isoxazolyl))-3-(phenylaminocarbonyl)thiophene-2-sulfonamide | 0.163 | >100 |
| N-(4-chloro-3-methyl-5-isoxazolyl)-2-[(4-tolyl)aminocarbonyl]thiophene-3-sulfonamide | 0.00116<br>0.0105† | 2.93<br>14† |
| N-(3,4-dimethyl-5-isoxazolyl)-2-[(4-methylphenyl)-aminocarbonyl]thiophene-3-sulfonamide | 0.00336 | 11.3 |
| N-(4-bromo-3-methyl-5-isoxazolyl)-2-[(methyl)phenyl-aminocarbonyl]thiophene-3-sulfonamide | 0.188 | 16.0 |
| N-(4-bromo-3-methyl-5-isoxazolyl)-2-(α-hydroxybenzyl)thiophene-3-sulfonamide | 0.337 | 9.37 |
| N-(4-bromo-5-methyl-3-isoxazolyl)-5-(4-methylphenyl)thiophene-2-sulfonamide | 7.10<br>15.8† | 0.3593<br>0.25† |
| N-(4-bromo-3-methyl-5-isoxazolyl)-2-(hydroxymethyl)thiophene-3-sulfonamide | 0.160<br>1.55† | 44.1<br>— |
| N-(4-bromo-3-methyl-5-isoxazolyl)-5-(2-formylphenyl)thiophene-3-sulfonamide | 3.46<br>12.31† | 0.529<br>1.28 ± 0.71† |
| N-(3,4-dimethyl-5-isoxazolyl))-2-[(3-methoxyanilino)methyl]thiophene-3-sulfonamide | 0.214<br>0.933† | 5.34<br>7.7† |
| N-(4-bromo-3-methyl-5-isoxazolyl)-2-[(3-carboxyphenyl)aminocarbonyl]thiophene-3-sulfonamide | 0.062† | >100† |
| N-(4-bromo-3-methyl-5-isoxazolyl)-2-[2-carboxylphenyl)aminocarbonyl]-thiophene-3-sulfonamide | 0.21† | 20† |
| N-(4-bromo-3-methyl-5-isoxazolyl)-2-(aminocarbonyl)thiophene-3-sulfonamide | 0.84† | >100† |
| N-(4-bromo-3-methyl-5-isoxazolyl)-2-[(5-dimethylamino-1-naphthyl)sulfonylaminocarbonyl]thiophene-3-sulfonamide | 0.97† | 3.9† |
| N-(4-bromo-3-methyl-5-isoxazolyl)-5-(5-methyl-2-thienyl)thiophene-2-sulfonamide | 17† | 0.21† |
| N-(4-bromo-3-methyl-5-isoxazolyl)-2-[(3,4-methylenedioxyphenyl)aminocarbonyl]thiophene-3-sulfonamide | 0.017† | 9.8† |
| N-(4-bromo-3-methyl-5-isoxazolyl)-2-[(3,4-methylenedioxy)phenoxycarbonyl]thiophene-3-sulfonamide | 0.0073† | 6.0† |
| N-(4-bromo-3-methyl-5-isoxazolyl)-3-[(3,4-methylenedioxy)phenyl]thiophene-2-sulfonamide | 0.50† | 79† |
| N-(4-bromo-3-methyl-5-isoxazolyl)-3-[(3,4-methylenedioxy)benzyl]thiophene-2-sulfonamide | 8.1† | 3.2† |
| N-(4-bromo-3-methyl-5-isoxazolyl)-3-benzylthiophene-2-sulfonamide | 1.6† | 39† |
| N-(4-bromo-3-methyl-5-isoxazolyl)-2-[(3,4-methylenedioxy)benzyl]thiophene-3-sutfonamide | 0.27† | 7.7† |
| N-(4-bromo-3-methyl-5-isoxazolyl)-2-[(3,4-methytenedioxy)benzoyl]thiophene-3-sulfonamide | 2.0† | 15† |
| N-(4-bromo-3-methyl-5-isoxazolyl)-2-[(2-hydroxyphenyl)aminocarbonyl]thiophene-3-sulfonamide | 0.013† | 38† |
| N-(3,4-dimethyl-5-isoxazolyl)-2-[3,4-(methylenedioxy)phenoxycarbonyl]thiophene-3-sulfonamide | 6.1† | >~50† |
| N-(4-bromo-3-methyl-5-isoxazolyl)-2-[(3,4-methylenedioxy)benzoyl]aminocarbonyl]thiophene-3-sulfonamide | 0.089† | 37† |
| N-(4-chloro-3-methyl-5-isoxazolyl)-2-[3,4-(methylenedioxy)phenoxycarbonyl]thiophene-3-sulfonamide | 0.0065† | 7.4† |
| N-(4-bromo-3-methyl-5-isoxazolyl)-2-[(3,4-methylenedioxy)phenylacetyl]thiophene-3-sulfonamide | 0.0091† | 5.5† |
| N-(4-bromo-3-methyl-5-isoxazolyl)-2-[3,4-(methylenedioxy)phenoxycarbonylamino]thiophene-3-sulfonamide | 0.087† | 5.9† |
| N-(4-bromo-3-methyl-5-isoxazolyl)-2-[(2-chloro-3,4-methylenedioxy)phenoxymethyl]thiophene-3-sulfonamide | 13† | 0.76† |

TABLE 1-continued

| COMPOUND | $ET_A$ ($\mu$M)* | $ET_B$ ($\mu$M)* |
|---|---|---|
| N-(4-bromo-3-methyl-5-isoxazotyl)-2-[trans-(3,4-methylenedioxy)cinnamyl]thiophene-3-sulfonamide | 0.14[†] | 1.4[†] |
| N-(4-bromo-3-methyl-5-isoxazolyl)-2-[(3,4-methylenedioxy)phenylureido]thiophene-3-sulfonamide | 0.57[†] | 1.3[†] |
| N-(4-chloro-3-methyl-5-isoxazolyl)-2-[(3,4-(methylenedioxy)phenylacetyl]thiophene-3-sulfonamide | 0.021[†] | 6.5[†] |
| N-(4-chloro-3-methyl-5-isoxazolyl)-2-[3,4-(methylenedioxy)benzyloxycarbonyl]thiophene-3-sulfonamide | 0.42[†] | 12[†] |
| N-(4-chloro-3-methyl-5-isoxazolyl)-2-[2-(3,4-methylenedioxyphenyl)ethoxycarbonyl-3-sulfonamide | 0.23[†] | 6.2[†] |
| N-(4-chloro-3-methyl-5-isoxazolyl)-2-{[4-(3,4-methylenedioxybenzyl)piperazin-1-yl]carbonyl}thiophene-3-sulfonamide | 20[†] | >~100[†] |
| N-(4-chloro-3-methyl-5-isoxazolyl)-2-aminothiophene-3-sulfonamide | 14[†] | 6.2[†] |
| N-(4-chloro-3-methyl-5-isoxazolyl)-2-{1-cyano-1-[(3,4-methylenedioxy)phenyl]acetyl}thiophene-3-sulfonamide | 2.1[†] | 27[†] |
| N-(4-bromo-3-methyl-5-isoxazolyl)-2-[(3,4-methylenedioxy)phenethyl]thiophene-3-sulfonamide | 0.21[†] | 9.2[†] |
| N-(4-chloro-3-methyl-5-isoxazolyl)-2-[(3-dimethylamino)phenoxycarbonyl]thiophene-3-sulfonamide | 1.4[†] | 60[†] |
| N-(4-chloro-3-methyl-5-isoxazolyl)-2-β-hydroxy(3,4-methylenedioxy)phenylethyl]thiophene-3-sulfonamide | 0.053[†] | 16[†] |
| N-(4-chloro-3-methyl-5-isoxazolyl)-2-[(4-oxacyclohexyl)oxycarbonyl]thiophene-3-sulfonamide | 1.37[†] | — |
| N-2-[3,4-(methylenedioxy)phenylacetyl]thiophene-3-sulfonamide | 1.8[†] | 32.5[†] |
| N-(4-chloro-3-methyl-5-isoxazolyl)-2-[(4-methoxyphenoxy)carbonyl]thiophene-3-sulfonamide | 0.023[†] | 15[†] |
| N-(4-bromo-3-methyl-5-isoxazolyl)-2-[(4-methylphenoxy)carbonyl]thiophene-3-sulfonamide | 122[†] | 9.7[†] |
| N-(4-chloro-3-methyl-5-isoxazolyl)-2-[(4-methoxyphenyl)acetyl]thiophene-3-sulfonamide | 0.043[†] | 10.1[†] |
| N-(4-bromo-3-methyl-5-isoxazolyl)-3-[(4-methylphenoxy)methyl]thiophene-2-sulfonamide | 1.64[†] | 22.8[†] |
| N-(4-bromo-3-methyl-5-isoxazolyl)-2-[(4-methylphenoxy)methyl]thiophene-3-sulfonamide | 1.2[†] | 15[†] |
| N-(4-bromo-3-methyl-5-isoxazolyl)-3-(4-methyl-trans-styryl)thiophene-2-sulfonamide | 0.94[†] | 0.66[†] |
| N-(4-bromo-3-methyl-5-isoxazolyl)-3-(4-methyl-phenethyl)thiophene-2-sulfonamide | 0.347[†] | 9.4[†] |
| N-(4-bromo-3-methyl-5-isoxazolyl)-2-[(4-methyl-phenyl)acetyl]thiophene-3-sulfonamide | 0.198[†] | 9.13[†] |
| N-(4-bromo-3-methyl-5-isoxazolyl)-2-[(3-methoxyphenyl)acetyl]thiophene-3-sulfonamide | 0.030[†] | 19.1[†] |
| N-(4-chloro-3-methyl-5-isoxazolyl)-2-[β,β-(ethylenedioxy)-3,4-(methylenedioxy)phenethyl]thiophene-3-sulfonamide | 0.128[†] | 2.09[†] |
| N-(4-chloro-3-methyl-5-isoxazolyl)-2-[β-(dimethylamino)-3,4-(methylenedioxy)phenethyl]thiophene-3-sulfonamide | 20.9[†] | ~100[†] |
| N-(4-chloro-3-methyl-5-isoxazolyl)-2-{α-hydroxy-[3,4-(methylenedioxy)phenyl]acetyl}thiophene-3-sulfonamide | 2.5[†] | 30[†] |
| N-(4-chloro-3-methyl-5-isoxazolyl)-2-[5-methyl-3-isoxazolyl)aminocarbonyl]thiophene-3-sulfonamide | 0.056[†] | 92[†] |
| N-(4-bromo-3-methyl-5-isoxazolyl)-2-[(3-hydroxyl-6-pyridazinyl)aminocarbonyl]thiophene-3-sulfonamide | 0.066[†] | 81.3[†] |
| N-(4-chloro-3-methyl-5-isoxazolyl)2-{[2-acetyl-4,5-(methylenedioxy)phenyl]aminocarbonyl}thiophene-3-sulfonamide | 0.010[†] | 31.6[†] |
| N-(4-bromo-3-methyl-5-isoxazolyl)-3-{[3,4-(methylenedioxy)phenoxy]methyl}thiophene-2-sulfonamide | 0.513[†] | 9.6[†] |
| N-(4-bromo-3-methyl-5-isoxazolyl)-2-[(4-methyl)(cinnamyl)] thiophene-3-sulfonamide | 0.26[†] | 0.413[†] |
| N-(4-chloro-3-methyl-5-isoxazolyl)-2-[(4,5-dimethoxy-2-methoxycarbonylphenyl)aminocarbonyl]thiophene-3-sulfonamide | 0.55[†] | — |
| N-(4-chloro-3-methyl-5-isoxazolyl)-2-[(2-methyl-1,3,4-thiadiazol-5-yl)aminocarbonyl]thiophene-3-sulfonamide | 0.13[†] | — |
| N-(4-chloro-3-methyl-5-isoxazolyl)2-{[2-carboxyl-4,5-(methylenedioxy)phenyl]aminocarbonyl}thiophene-3-sulfonamide. | 1.43[†] | — |
| N-(4-brp,p-3-methyl-5-isoxazolyl)-3-[3,4-(methylenedioxy)phenethyl]thiophene-2-sulfonamide | 0.236[†] | 18[†] |
| N-(4-bromo-3-methyl-5-isoxazolyl)-3-[3,4-(methylenedioxy)-trans-styryl]thiophene-2-sulfonamide | 0.218[†] | 10[†] |
| N-(4-bromo-3-methyl-5-isoxazolyl)-2-[(4-methyl)-phenethyl]thiophene-3-sulfonamide | 0.106[†] | 40.1[†] |
| N-(4-chloro-3,4-dimethyl-5-isoxazolyl)-2-{[2-acetyl-4,5-(methylenedioxy)phenyl]aminocarbonyl}thiophene-3-sulfonamide | 0.032[†] | — |

TABLE 1-continued

| COMPOUND | ET$_A$ ($\mu$M)* | ET$_B$ ($\mu$M)* |
|---|---|---|
| N-(4-chloro-3-methyl-5-isoxazolyl)-2-[4-methoxy-2-methylphenyl)aminocarbonyl]thiophene-3-sulfonamide | 0.027† | 0.14† |
| N-(4-chloro-3-methyl-5-isoxazolyl)-2-[{2-cyano-4,5-dimethoxyphenyl)aminocarbonyl]thiophene-3-sulfonamide | 0.0039† | 12.2† |
| N-(3,4-dimethyl-5-isoxazolyl)-2-(4-tolylacetylphenyl)thiophene-3-sulfonamide | 0.0027† | 29.2† |
| N-(3,4-dimethyl-5-isoxazolyl)-2-[3,4-(methylene-dioxy)phenylacetyl]thiophene-3-sulfonamide | 0.0273† | 12.2† |
| N-(4-chloro-3-methyl-5-isoxazolyl)-2-[(2,4-dimethoxyphenyl)aminocarbonyl]thiophene-3-sulfonamide | 0.158† | 63.1† |
| N-(4-chloro-3-methyl-5-isoxazolyl)-2-[(2,4-pyridyl)aminocarbonyl]thiophene-3-sulfonamide | 0.023† | 43.7† |
| N-(4-chloro-3-methyl-5-isoxazolyl)-2-[2-hydroxy-4-methylphenyl)aminocarbonyl]thiophene-3-sulfonamide | 0.006† | — |
| N-(4-chloro-3-methyl-5-isoxazolyl)-2-{[2-cyano-4,5-(methylenedioxy)phenyl]aminocarbonyl}thiophene-3-sulfonamide | 0.0034† | 40.4† |
| N-(4-chloro-3-methyl-5-isoxazolyl)-2-[2-mthyl-4,5-(methylenedioxy)phenylaminocarbonyl]thiophene-3-sulfonamide | 0.0030† | 355† |
| N-(4-chloro-3-methyl-5-isoxazolyl)-2-(2-carboxamido-4,5-dimethoxyphenylaminocarbonyl)thiophene-3-sulfonamide | 0.011† | 61† |
| N-(3,4-dimethyl-5-isoxazolyl)-2-(2,4-dimethylphenylacetyl)thiophene-3-sulfonamide | 0.0027† | 17.4† |
| N-(4-chloro-3-methyl-5-isoxazolyl)-2-(2,4-dimethyl-phenylacetyl)thiophene-3-sulfonamide | 0.0004† | 4.8† |
| N-(4-bromo-3-methyl-5-isoxazolyl)-2-(2,4-dimethylphenylacetyl)thiophene-3-sulfonamide | 0.0008†** | 3.6† |
| N-(4-chloro-3-methyl-5-isoxazolyl)-2-[3,4-(methylenedioxy)]phenylaminocarbonyl-3-thio-phenesulfonamide | 0.0073† | 9.2† |
| N-(4-chloro-3-methyl-5-isoxazolyl)-2-[2-methyl-4,5-(methylenedioxy)phenylacetyl]thiophene-3-sulfonamide | 0.01464 ±0.00624† | 52.782 ±23.24† |
| N-(4-chloro-3-methyl-5-isoxazolyl)-2-[3,4-(methylenedioxy)-6-(2-acetoxyethyl)phenylaminocarbonyl]thiophene-3-sulfonamide | 0.0045† | 25.7† |
| N-(4-chloro-3-methyl-5-isoxazolyl)-2-[3,4-(methylenedioxy)-6-(2-hydroxyethyl)phenylaminocarbonyl]thiophene-3-sulfonamide | 0.0056† | 16.8† |
| N-(4-chloro-3-methyl-5-isoxazolyl)-2-(3,5-dimethyl-phenylacetyl)thiophene-3-sulfonamide | 0.045† | 17.7† |
| N-(4-chloro-3-methyl-5-isoxazolyl)-2-(2,5-dimethylphenylacetyl)thiophene-3-sulfonamide | 0.007† | 18† |
| N-(4-chloro-3-methyl-5-isoxazolyl)-2-[2-methanesulfonylaminomethyl)-4,5-(methylenedioxy)phenylaminocarbonyl]thiophene-3-sulfonamide | 0.0068† | 19.8† |
| N-(4-chloro-3-methyl-5-isoxazolyl)-2-[2-cyanomethyl-4,5-(methylenedioxy)-6-cyanomethyl]phenylamino-carbonylthiophene-3-sulfonamide | 0.0038† | 25† |
| N-(4-chloro-3-methyl-5-isoxazolyl)-2-[2-hydroxypropyl-4,5-(methylenedioxy)phenylaminocarbonyl]thiophene-3-sulfonamide | 0.0073† | 8.3† |
| N-(4-bromo-3-methyl-5-isoxazolyl)-3-[2-methyl-4,5-(methylenedioxy)cinnamyl]thiophene-2-sulfonamide | ~0.1†** | ~6†** |
| N-(4-bromo-3-methyl-5-isoxazolyl)-3-[2-methyl-4,5-(methylenedioxy)phenethyl]thiophene-2-sulfonamide | ~0.1†** | ~5†** |
| N-(4-bromo-3-methyl-5-isoxazolyl)-3-{[2-propyl-4,5-(methylenddioxy)phenoxy]methyl}thiophene-2-sulfonamide | ~0.2†** | ~1.5†** |
| N-(4-chloro-3-methyl-5-isoxazolyl)-2-[3,4-(methylenedioxy)-6-(2-acetoxyethoxy)]phenylamino-carbonyl]thiophene-3-sulfonamide | ~0.02†** | ~18† |
| N-(4-chloro-3-methyl-5-isoxazolyl)-2-[3,4-(methylenedioxy)-6-(2-hydroxyethoxy)phenylamino-carbonyl]thiophene-3-sulfonamide | ~0.01†** | ~18† |
| N-(4-chloro-3-methyl-5-isoxazolyl)-2-[2-cyano-4,5-(methylenedioxy)phenylacetyl]thiophene-3-sulfonamide | ~0.3†** | ~0.7† |
| N-(4-chloro-3-methyl-5-isoxazolyl)-2-{2-[(dimethylamino)carbonylmethyl]-4,5-(methylene-dioxy)phenylaminocarbonyl}thiophene-3-sulfonamide | 0.009† | 13.8† |
| N-(4-chloro-3-methyl-5-isoxazolyl)-2-[2-methyl-4,5-(methylenedioxy)phenylhydroxyimino]thiophene-3-sulfonamide | 0.794† | 6.49† |
| N-(4-bromo-3-methyl-5-isoxazolyl)-2-[2-methyl-4,5-(methylenedioxy)phenethyl]thiophene-3-sulfonamide | 0.0619† | 8.90† |
| N-(4-bromo-3-methyl-5-isoxazolyl)-3-[2-(hydroxymethyl)-4,5-(methylenedioxy)cinnamyl]thiophene-2-sulfonamide | 0.0795† | 3.24† |

TABLE 1-continued

| COMPOUND | ET$_A$ (µM)* | ET$_B$ (µM)* |
|---|---|---|
| N-(4-bromo-3-methyl-5-isoxazolyl)-3-{2-[(tetrahydro-4H-pyran-2-yloxy)methyl]-4,5-(methylenedioxy)cinnamyl}thiophene-2-sulfonamide | 0.0967† | 4.14† |
| N-(4-bromo-3-methyl-5-isoxazolyl)-3-(2,4-dimethylphenethyl)thiophene-2-sulfonamide | 0.1006† | 4.30† |
| N-(4-bromo-3-methyl-5-isoxazolyl)-3-(2,4-dimethylcinnamyl)thiophene-2-sulfonamide | 0.180† | 2.97† |
| N-(4-bromo-3-methyl-5-isoxazolyl)-2-(2,4-dimethylcinnamyl)thiophene-3-sulfonamide | 0.166† | 2.97† |
| N-(4-bromo-3-methyl-5-isoxazolyl)-3-[(2,4-dimethylphenoxy)methyl]thiophene-2-sulfonamide | 0.346† | 7.45† |
| N-(4-bromo-3-methyl-5-isoxazolyl)-2-[(2,4-dimethylphenoxy)methyl]thiophene-3-sulfonamide | 0.308† | 4.48† |
| N-(4-chloro-3-methyl-5-isoxazolyl)-5-(phenylaminocarbonyl)thiophene-2-sulfonamide | 28.1† | 60.6† |
| N-(4-chloro-3-methyl-5-isoxazolyl)-2-[β-acetoxy-2-methyl-4,5-(methylenedioxy)styryl]thiophene-3-sulfonamide | 0.00544† | 3.74† |
| N-(4-chloro-3-methyl-5-isoxazolyl)-2-[(2,3,4-trimethoxy-6-cyano)phenylaminocarbonyl]thiophene-3-sulfonamide | 0.00024† | 6.998† |
| N-(4-chloro-3-methyl-5-isoxazolyl)-2-[2-(cyano)phenyl]benzo[b]thiophene-3-sulfonamide | 6.33† | 8.82† |
| N-(4-chloro-3-methyl-5-isoxazolyl)-2-[3,4-(methylenedioxy)phenyl]benzo[b]thiophene-3-sulfonamide | 0.550† | 52.6† |
| N-(4-bromo-3-methyl-5-isoxazolyl)-3-(2-tolyl)thiophene-2-sulfonamide | 0.324† | 55.1† |
| N-(4-bromo-3-methyl-5-isoxazolyl)-3-(3-tolyl)thiophene-2-sulfonamide | 0.832† | 21.2† |
| N-(4-bromo-3-methyl-5-isoxazolyl)-3-(2-tolyl)thiophene-2-sulfonamide | 0.302† | 31%@100† |
| N-(4-bromo-3-methyl-5-isoxazolyl)-3-(3-methoxyphenyl)thiophene-2-sulfonamide | 0.334† | ** |
| N-(4-bromo-3-methyl-5-isoxazolyl)-3-(3-methoxyphenyl)thiophene-2-sulfonamide | 1.32† | 56.3† |
| N-(4-bromo-3-methyl-5-isoxazolyl)-3-(2-methoxyphenyl)thiophene-2-sulfonamide | 1.71† | 59.1† |
| N-(4-bromo-3-methyl-5-isoxazolyl)-3-(4-ethylphenyl)thiophene-2-sulfonamide | 0.184 | 43.9† |
| N-(4-bromo-3-methyl-5-isoxazolyl)-3-(4-propylphenyl)thiophene-2-sulfonamide | 0.0873 | 8.48† |
| N-(4-bromo-3-methyl-5-isoxazolyl)-3-(4-iso-propylphenyl)thiophene-2-sulfonamide | 0.218 | 28.3† |
| N-(4-bromo-3-methyl-5-isoxazolyl)-3-(4-butylphenyl)thiophene-2-sulfonamide | 0.160 | 6.11† |
| N-(3,4-dimethyl-5-isoxazolyl)-2-[2-methyl-4,5-(methylenedioxy)phenylacetyl]thiophene-3-sulfonamide | 0.00328† | 34.3† |
| N-(4-chloro-3-methyl-5-isoxazolyl)-2-(2,4,6-trimethylphenylaminocarbonyl)thiophene-3-sulfonamide | 0.00160† | 11.272† |
| N-(4-chloro-3-methyl-5-isoxazolyl)-2-(2,4,6-tri-methylphenylacetyl)thiophene-3-sulfonamide | 0.000238† | 3.82† |
| N-(4-chloro-5-methyl-3-isoxazolyl)-2-[2-methyl-4,5-(methylenedioxy)phenylacetyl]thiophene-3-sulfonamide | 0.000625† | 3.69† |
| N-(4-bromo-3-methyl-5-isoxazolyl)-2-[2-methyl-4,5-(methylenedioxy)cinnamyl]thiophene-3-sulfonamide | 0.0804† | 3.28† |
| N-(4-bromo-3-methyl-5-isoxazolyl)-2-(2,4-dimethylphenethyl)thiophene-3-sulfonamide | 0.0555† | 3.48† |
| N-(4-chloro-3-methyl-5-isoxazolyl)-2-[(4-methoxycarbonyl-2,6-dimethyl)phenylaminocarbonyl]thiophene-3-sulfonamide | 0.000266† | 9.78† |
| N-(4-chloro-3-methyl-5-isoxazolyl)-2-(phenoxycarbonyl)thiophene-3-sulfonamide | 4.41† | 31%@100† |
| N-(4-bromo-3-methyl-5-isoxazolyl)-2-(phenoxycarbonyl)thiophene-3-sulfonamide | 2.71† | 20%@100† |
| N-(3,4-dimethyl-5-isoxazolyl)-2-{[3,4-(methylenedioxy)phenoxy]carbonyl}thiophene-3-sulfonamide | 3.61† | 30%@100† |
| N-(4-bromo-3-methyl-5-isoxazolyl)-2-[(2-methylphenoxy)carbonyl]thiophene-3-sulfonamide | 0.684† | 105† |
| N-(4-bromo-3-methyl-5-isoxazolyl)-2-[(3-methylphenoxy)carbonyl]thiophene-3-sulfonamide | 1.20† | 111† |
| N-(4-bromo-3-methyl-5-isoxazolyl)-2-[(2,4-dimethylphenoxy)carbonyl]thiophene-3-sulfonamide | 0.291† | 43.2† |
| N-(4-bromo-3-methyl-5-isoxazolyl)-2-[(2-methoxylphenoxy)carbonyl]thiophene-3-sulfonamide | 0.761† | 29%@100† |
| N-(4-bromo-3-methyl-5-isoxazolyl)-2-[(3-methoxylphenoxy)carbonyl]thiophene-3-sulfonamide | 0.79† | 90† |
| N-(4-bromo-3-methyl-5-isoxazolyl)-2-[(4-methoxylphenoxy)carbonyl]thiophene-3-sulfonamide | 1.73† | 111† |

TABLE 1-continued

| COMPOUND | ET$_A$ (μM)* | ET$_B$ (μM)* |
|---|---|---|
| N-(3,4-dimethyl-5-isoxazolyl)-2-[(4-methoxylphenoxy)carbonyl]thiophene-3-sulfonamide | 5.88† | 13%@100† |
| N-(3,4-dimethyl-5-isoxazolyl)-2-[(4-methoxylphenoxy)carbonyl]thiophene-3-sulfonamide | 2.5† | 33%@100† |
| N-(4-chloro-3-methyl-5-isoxazolyl)-2-[(4-methylphenoxy)carbonyl]thiophene-3-sulfonamide | 3.2† | 43%@100† |
| N-(4-chloro-3-methyl-5-isoxazolyl)-2-[(2,4-dimethylphenoxy)carbonyl]thiophene-3-sulfonamide | 0.648† | 68.5† |
| N-(3,4-dimethyl-5-isoxazolyl)-2-[(2,4-dimethylphenoxy)carbonyl]thiophene-3-sulfonamide | 0.274† | 21%@100† |
| N-(4-bromo-3-methyl-5-isoxazolyl)-2-{[2-propyl-4,5-(methylenedioxy)phenox]carbonyl}thiophene-3-sulfonamide | 0.138† | 11.9† |
| N-(4-chloro-3-methyl-5-isoxazolyl)-2-(3-methoxycarbonyl-2,4,6-trimethylphenylaminocarbonyl)thiophene-3-sulfonamide | 0.000321†<br>0.00092† | 16.5†<br>— |
| N-(4-bromo-3-methyl-5-isoxazolyl)-3-(2,4-dimethylphenyl)thiophene-2-sulfonamide | 0.100† | 60.3† |
| N-(3,4-dimethyl-5-isoxazolyl)-2-(phenoxycarbonyl)thiophene-3-sulfonamide | 2.85† | 31%† |
| N-(4-bromo-3-methyl-5-isoxazolyl)-3-(4-iso-butylphenyl)thiophene-2-sulfonamide | 0.0823† | 2.76† |
| N-(4-bromo-3-methyl-5-isoxazolyl)-3-(4-iso-pentylphenyl)thiophene-2-sulfonamide | 0.155† | 3.31† |
| N-(4-bromo-3-methyl-5-isoxazolyl)-3-[(2,4,6-trimethylphenoxy)methyl]thiophene-2-sulfonamide | 0.0457† | 4.68† |
| N-(4-bromo-3-methyl-5-isoxazolyl)-2-[(2,4,6-trimethylphenoxy)methyl]thiophene-3-sulfonamide | 0.0562† | 3.39† |
| N-(4-bromo-3-methyl-5-isoxazolyl)-3-(2,4,6-trimethylcinnamyl)thiophene-2-sulfonamide | 0.0490† | 1.86† |
| N-(4-bromo-3-methyl-5-isoxazolyl)-3-(2,4,6-propylphenyl)thiophene-2-sulfonamide | 0.0468† | 3.63† |
| N-(4-bromo-3-methyl-5-isoxazolyl)-3-(4-iso-butyl-2-methylphenyl)thiophene-2-sulfonamide | 0.0468† | 1.66† |
| N-(4-bromo-3-methyl-5-isoxazolyl)-3-(4-iso-pentyl-2-methylphenyl)thiophene-2-sulfonamide | 0.107† | 2.40† |
| N-(4-bromo-3-methyl-5-isoxazolyl)-2-{[3,4-(methylenedioxy)phenoxy]methyl}thiophene-3-sulfonamide | 0.302† | 6.61† |
| N-(4-bromo-3-methyl-5-isoxazolyl)-2-{[4,5-(methylenedioxy)-2-propylphenoxy]methyl}thiophene-3-sulfonamide | 0.107† | 0.407† |
| N-(4-bromo-3-methyl-5-isoxazolyl)-2-(2,4,6-trimethylphenethyl)thiophene-3-sulfonamide | 0.0417† | 1.23† |
| N-(4-bromo-3-methyl-5-isoxazolyl)-3-(2,4,6-trimethylphenethyl)thiophene-2-sulfonamide | 0.055† | 1.62† |
| N-(3,4-dimethyl-5-isoxazolyl)-2-[(2,4,6-trimethylphenoxy)carbonyl]thiophene-3-sulfonamide | 0.537† | 8%@100† |
| N-(4-chloro-3-methyl-5-isoxazolyl)-2-[(2,4,6-trimethylphenoxy)carbonyl]thiophene-3-sulfonamide | 0.0776† | 30.2† |
| N-(4-bromo-3-methyl-5-isoxazolyl)-2-[(2,4,6-trimethylphenoxy)carbonyl]thiophene-3-sulfonamide | 0.479† | 24.5† |
| N-(4-chloro-3-methyl-5-isoxazolyl)-2-(3-cyanomethyl-2,4,6-trimethylphenylaminocarbonyl)thiophene-3-sulfonamide | 0.00118<br>±0.00065† | 38.782<br>±23.377† |
| N-(4-chloro-3-methyl-5-isoxazolyl)-2-(3-carboxymethyl-2,4,6-trimethylphenylaminocarbonyl)thiophene-3-sulfonamide | 0.00177<br>±0.00036† | 106.066<br>±14.632† |
| N-(4-chloro-3-methyl-5-isoxazolyl-2-(3-acetoxymethyl-2,4,6-trimethylphenylaminocarbonyl)thiophene-3-sulfonamide | 0.00086<br>±0.00012† | 729.577<br>± 094.031† |
| N-(4-chloro-3-methyl-5-isoxazolyl)-2-(3-hydroxymethyl-2,4,6-trimethylphenylaminocarbonyl)thiophene-3-sulfonamide | 0.00067<br>±0.00014† | 74.224<br>±48.771† |
| N-(4-chloro-3-methyl-5-isoxazolyl)-2-(3-methoxycarbonylmethyl-2,4,6-trimethylphenylaminocarbonyl)thiophene-3-sulfonamide | 0.00100<br>±0.00012† | 114.040<br>±2.599† |
| N-(4-chloro-3-methyl-5-isoxazolyl)-2-(3-dimethylaminomethyl-2,4,6-trimethylphenylaminocarbonyl)thiophene-3-sulfonamide, trifluoroacetic acid salt | 0.01337† | — |
| N-(4-chloro-3-methyl-5-isoxazolyl)-2-(α-methyl-2-)methyl-4,5-(methylenedioxy)phenylacetyl)thiophene-3-sulfonamide | 0.08531† | — |
| N-(4-chloro-3-methyl-5-isoxazolyl)-2-(α-carboxylmethyl-2-methyl-4,5-(methylenedioxy)phenylacetyl)thiophene-3-sulfonamide | 0.08110† | — |
| N-(4-chloro-3-methyl-5-isoxazolyl)-2-(3-methanesulfonylamino-2,4,6-trimethylphenylaminocarbonyl)thiophene-3-sulfonamide | 0.00162<br>±0.00026† | 67.622<br>±67.866† |

TABLE 1-continued

| COMPOUND | $ET_A$ ($\mu$M)* | $ET_B$ ($\mu$M)* |
|---|---|---|
| N-(4-chloro-3-methyl-5-isoxazolyl)-2-(2-carbamoyl-4,6-dimethylphenylaminocarbonyl)thiophene-3-sulfonamide | 0.00146† | 11.885† |
| N-(4-chloro-3-methyl-5-isoxazolyl)-2-(3-hydroxy-2,4,6-trimethylphenylaminocarbonyl)thiophene-3-sulfonamide | 0.00171 ±0.00082† | 18.676 ±8.672† |
| N-(4-chloro-3-methyl-5-isoxazolyl)-2-(3-carboxyl-2,4,6-trimethylphenylaminocarbonyl)thiophene-3-sulfonamide | 0.01191† | 22.387† |
| N-(4-chloro-3-methyl-5-isoxazolyl)-2-(2-carboxyl-4,6-dimethylphenylaminocarbonyl)thiophene-3-sulfonamide | 0.02831† | 16.982† |
| N-(4-chloro-3-methyl-5-isoxazolyl)-2-(2-phenyl-4,6-dimethylphenylaminocarbonyl)thiophene-3-sulfonamide | 0.01589† | 29.512† |
| N-(4-chloro-3-methyl-5-isoxazolyl)-2-(3-cyano-2,4,6-trimethylphenylaminocarbonyl)thiophene-3-sulfonamide | 0.00152 ±0.00036† | 57.231 ±17.270† |
| N-(4-chloro-3-methyl-5-isoxazolyl)-2-(3-sulfamoyl-2,4,6-trimethylphenylaminocarbonyl)thiophene-3-sulfonamide | 0.00092 ±0.00059† | 25.520 ±10.416† |
| N-(4-chloro-5-methyl-3-isoxazolyl)-2-(3-cyanomethyl-2,4,6-trimethylphenylaminocarbonyl)thiophene-3-sulfonamide | 0.00088 ±0.00007† | 7.540 ±1.740† |
| N-(4-chloro-5-methyl-3-isoxazolyl)-2-(3-acetoxymethyl-2,4,6-trimethylphenylaminocarbonyl)thiophene-3-sulfonamide | 0.00051 ±0.00039† | 19.699 ±9.597† |
| N-(4-chloro-5-methyl-3-isoxazolyl)-2-(3-hydroxymethyl-2,4,6-trimethylphenylaminocarbonyl)thiophene-3-sulfonamide | 0.00088† | 3.083† |
| -trimethylphenylaminocarbonyl)thiophene-3-sulfonamide | 0.00066† | 9.550† |
| N-(3,4-dimethyl-5-isoxazolyl)-2-(3-cyanomethyl-2,4,6-trimethylphenylaminocarbonyl)thiophene-3-sulfonamide | 0.00156 ±0.00025† | 22.772 ±2.590† |
| N-(3,4-dimethyl-5-isoxazolyl)-2-(3-acetoxymethyl-2,4,6-trimethylphenylaminocarbonyl)thiophene-3-sulfonamide | 0.00097† | 155.955† |
| N-(3,4-dimethyl-5-isoxazolyl)-2-(3-hydroxymethyl-2,4,6-trimethylphenylaminocarbonyl)thiophene-3-sulfonamide | 0.00111† | 33.806† |
| N-(4-chloro-3-methyl-5-isoxazolyl)-2-(pentamethylphenylaminocarbonyl)thiophene-3-sulfonamide | 0.02985† | 30.974† |
| N-(4-chloro-3-methyl-5-isoxazolyl)-2-(2,4,6-trimethylbenzylaminocarbonyl)thiophene-3-sulfonamide | 17,458.222† | 69.183† |
| N-4-chloro-3-methyl-5-isoxazolyl)-2-(3-cyanomethyl-2,4,6-trimethylbenzylaminocarbonyl)thiophene-3-sulfonamide | 0.5310† | 81.470† |

*results are generally the average of 2 to 5 experiments
**preliminary results or results in which one or more data points were only determined approximately
†assay performed with incubation at 24° C. As described in the Examples, incubation at the higher temperature reduces the activity by a factor of 2- to about 10-compared to the activity at 4° C.
—data not available or measured as % inhibition @ 100 $\mu$M
%% inhibition @ 100 $\mu$M It is understood that 4-bromo or 4-chloro groups can be replaced by other 4-halo substituents or other suitable substituents for $R^1$, such as alkyl. Among the preferred compounds are:

N-(4-chloro-3-methyl-5-isoxazolyl)-2-[(2,3,4-trimethoxy-6-cyano)phenylaminocarbonyl]thiophene-3-sulfonamide,
N-(4-chloro-3-methyl-5-isoxazolyl)-2-(3-methoxycarbonyl-2,4,6-trimethylphenylaminocarbonyl)thiophene-3-sulfonamide, N-(4-chloro-3-methyl-5-isoxazolyl)-2-(3-cyanomethyl-2,4,6-trimethylphenylaminocarbonyl)thiophene-3-sulfonamide, N-(4-chloro-3-methyl-5-isoxazolyl)-2-(3-carboxymethyl-2,4,6-trimethylphenylaminocarbonyl)thiophene-3-sulfonamide, N-(4-chloro-3-methyl-5-isoxazolyl)-2-(3-acetoxymethyl-2,4,6-trimethylphenylaminocarbonyl)thiophene-3-sulfonamide, N-(4-chloro-3-methyl-5-isoxazolyl)-2-(3-hydroxymethyl-2,4,6-trimethylphenylaminocarbonyl)thiophene-3-sulfonamide, N-(4-chloro-3-methyl-5-isoxazolyl)-2-(3-methoxycarbonylmethyl-2,4,6-trimethylphenylaminocarbonyl)thiophene-3-sulfonamide, N-(4-chloro-3-methyl-5-isoxazolyl)-2-(3-dimethylaminomethyl-2,4,6-trimethylphenylaminocarbonyl)thiophene-3-sulfonamide, trifluoroacetic acid salt,
N-(4-chloro-3-methyl-5-isoxazolyl)-2-(α-methyl-2-methyl-4,5-(methylenedioxy)phenylacetyl)thiophene-3-sulfonamide,
N-(4-chloro-3-methyl-5-isoxazolyl)-2-(α-carboxylmethyl-2-methyl-4,5-(methylenedioxy)phenylacetyl)thiophene-3-sulfonamide
N-(4-chloro-3-methyl-5-isoxazolyl)-2-(3-methanesulfonylamino-2,4,6-trimethylphenylaminocarbonyl)thiophene-3-sulfonamide
N-(4-chloro-3-methyl-5-isoxazolyl)-2-(2-carbamoyl-4,6-dimethylphenylaminocarbonyl)thiophene-3-sulfonamide,
N-(4-chloro-3-methyl-5-isoxazolyl)-2-(3-hydroxy-2,4,6-trimethylphenylaminocarbonyl)thiophene-3-sulfonamide,
N-(4-chloro-3-methyl-5-isoxazolyl)-2-(3-carboxyl-2,4,6-trimethylphenylaminocarbonyl)thiophene-3-sulfonamide,
N-(4-chloro-3-methyl-5-isoxazolyl)-2-(2-carboxyl-4,6-dimethylphenylaminocarbonyl)thiophene-3-sulfonamide,
N-(4-chloro-3-methyl-5-isoxazolyl)-2-(2-phenyl-4,6-dimethylphenylaminocarbonyl)thiophene-3-sulfonamide,
N-(4-chloro-3-methyl-5-isoxazolyl)-2-(3-cyano-2,4,6-trimethylphenylaminocarbonyl)thiophene-3-sulfonamide,
N-(4-chloro-3-methyl-5-isoxazolyl)-2-(3-sulfamoyl-2,4,6-trimethylphenylaminocarbonyl)thiophene-3-sulfonamide,
N-(4-chloro-5-methyl-3-isoxazolyl)-2-(3-cyanomethyl-2,4,6-trimethylphenylaminocarbonyl)thiophene-3-sulfonamide, N-(4-chloro-5-methyl-3-isoxazolyl)-2-(3-acetoxymethyl-2,
   4,6-trimethylphenylaminocarbonyl)thiophene-3-
   sulfonamide,
N-(4-chloro-5-methyl-3-isoxazolyl)-2-(3-hydroxymethyl-2,
   4,6-trimethylphenylaminocarbonyl)thiophene-3-
   sulfonamide, -trimethylphenylaminocarbonyl)thiophene-
   3-sulfonamide,
N-(3,4-dimethyl-5-isoxazolyl)-2-(3-cyanomethyl-2,4,6-
   trimethylphenylaminocarbonyl)thiophene-3-
   sulfonamide,
N-(3,4-dimethyl-5-isoxazolyl)-2-(3-acetoxymethyl-2,4,6-
   trimethylphenylaminocarbonyl)thiophene-3-
   sulfonamide,
N-(3,4-dimethyl-5-isoxazolyl)-2-(3-hydroxymethyl-2,4,6-
   trimethylphenylaminocarbonyl)thiophene-3-
   sulfonamide,
N-(4-chloro-3-methyl-5-isoxazolyl)-2-
   (pentamethylphenylaminocarbonyl)thiophene-3-
   sulfonamide Table 2 lists oral half-life, bioavailability, and in vivo activity of selected exemplary compounds. The in vivo activity was measured in a pulmonary hypertension model and is a measure of the activity of the compounds at selected dosages. As Table 2 indicates, the compounds claimed herein exhibit improved oral half-life, bioavailability, and/or in vivo activity over those disclosed previously (see, e.g., PCT International Publication No. WO 96/31492).

TABLE 2

| COMPOUND | $P_{app}{}^a$ | $POt_{1/2}$ in Rat[b] | Peak Plasma Levels[c] | in vivo Efficacy[d] |
|---|---|---|---|---|
| N-(4-chloro-3-methyl-5-isoxazolyl)-2-[2-methyl-4,5-(methylenedioxy)phenyl-acetyl]thiophene-3-sulfonamide | 2.32 | 4.1 | 173 | ++ |
| N-(4-chloro-3-methyl-5-isoxazolyl)-2-[(2,3,4-trimethoxy-6-cyano)phenyl-aminocarbonyl]thiophene-3-sulfonamide | 0.58 | | | |
| N-(4-chloro-3-methyl-5-isoxazolyl)-2-(3-cyanomethyl-2,4,6-trimethylphenyl-aminocarbonyl)thiophene-3-sulfonamide | 1.78 | 3.4 | 40.2 | ++ |
| N-(4-chloro-3-methyl-5-isoxazolyl)-2-(3-methoxycarbonylmethyl-2,4,6-trimethylphenylaminocarbonyl)thiophene-3-sulfonamide | 1.69 | | | |
| N-(4-chloro-3-methyl-5-isoxazolyl)-2-(3-carboxymethyl-2,4,6-trimethylphenylaminocarbonyl)thiophene-3-sulfonamide | 1.10 | | | |
| N-(4-chloro-3-methyl-5-isoxazolyl)-2-(3-acetoxymethyl-2,4,6-trimethylphenylaminocarbonyl)thiophene-3-sulfonamide | 1.46 | | | |
| N-(4-chloro-3-methyl-5-isoxazolyl)-2-(3-hydroxymethyl-2,4,6-trimethylphenylaminocarbonyl)thiophene-3-sulfonamide | 1.56 | 1.5 | 3 | -/+ |
| N-(4-chloro-3-methyl-5-isoxazolyl)-2-(3-methanesulfonylamino-2,4-6-trimethylphenylaminocarbonyl)thiophene-3-sulfonamide | | 5.9 | 2.6 | |
| N-(4-chloro-3-methyl-5-isoxazolyl)-2-(3-hydroxy-2,4,6-trimethylphenylamino-carbonyl)thiophene-3-sulfonamide | | 7 | 5.6 | ++ |
| N-(4-chloro-3-methyl-5-isoxazolyl)-2-(3-cyano-2,4,6-trimethylphenylamino-carbonyl)thiophene-3-sulfonamide | | 3.9 | 20 | ++ |
| N-(4-chloro-3-methyl-5-isoxazolyl)-2-(3-sulfamoyl-2,4,6-trimethylphenyl aminocarbonyl)thiophene-3-sulfonamide | | 3.4 | 2.8 | |
| N-(4-chloro-5-methyl-3-isoxazolyl)-2-(3-cyanomethyl-2,4,6-trimethylphenyl-aminocarbonyl)thiophene-3-sulfonamide | | 25.6 | 13 | – |
| N-(3,4-dimethyl-5-isoxazolyl)-2-(3-cyanomethyl-2,4,6-trimethylphenyl-aminocarbonyl)thiophene-3-sulfonamide | | 1.8 | 10.9 | |

[a]× $10^{-6}$ cm/sec
[b]in hours
[c]in μg/mL
[d]Pulmonary Hypertension model:
++ effective at 5 mg/kg
– no effect at 5 mg/kg
+ effective at 15 mg/kg B. Preparation of the Compounds The preparation of some of the above and other compounds that possess the requisite activities are set forth in the Examples. Compounds whose synthesis is not explicitly exemplified can be synthesized by routine modification of one or more methods described in detail in the Examples by substituting appropriate readily available reagents.

Many of the compounds described herein are 3-sulfamoyl-2-arylaminocarbonylthiophene derivatives. In general, these compounds may be prepared by coupling of the appropriate 3-sulfamoylthienylcarboxylic acid with a substituted or unsubstituted aniline.

The 3-sulfamoylthienylcarboxylic acids may be prepared by a variety of methods known the those of skill in the art. In general, most of the syntheses involve the condensation of a carboalkoxythienylsulfonyl chloride with an aminoisoxazole in dry pyridine or in tetrahydrofuran (THF) and sodium hydride. Subsequent hydrolysis of the carboalkoxy group provides the desired acids. The sulfonyl chlorides and aminoisoxazoles either can be obtained commercially or synthesized according to methods described in the Examples or using other methods available to those of skill in this art (see, e.g., U.S. Pat. Nos. 4,659,369, 4,861,366 and 4,753, 672).

For example, the thienylsulfonyl chlorides may be prepared by the following methods. A 3-sulfamoylthiophene precursor may be brominated at the 2-position by reaction with, for example, bromine or N-bromosuccinimide. Subsequent metal-halogen exchange with an alkyllithium, e.g., n-butyllithium, and reaction with carbon dioxide provides the desired acid. Alternatively, a 2-thienylcarboxylic acid derivative may be sulfonated at the 3-position by reaction with, e.g., sulfur trioxide in sulfuric acid. Conversion of the resulting sulfonic acid to a sulfonyl chloride (by reaction with phosphorous pentachloride, phosphorous trichloride, phosphorous oxychloride, thionyl chloride, or oxalyl choride) followed by reaction with the appropriate amine provides the desired sulfamoylthienylcarboxylic acid derivative. The intermediate sulfonyl chloride may also be prepared directly by reaction of the thienylcarboxylic acid derivative with chlorosulfonic acid.

The N-(alkylisoxazolyl)sulfonamides can be prepared by condensing an aminoisoxazole with a sulfonyl chloride in dry pyridine with or without the catalyst 4-(dimethylamino)

pyridine. The N-(3,4-dimethyl-5-isoxazolyl)sulfonamides and N-(4,5-dimethyl-3-isoxazolyl)sulfonamides can be prepared from the corresponding aminodimethylisoxazole, such as 5-amino-3,4-dimethylisoxazole. For example, N-(3,4-dimethyl-5-isoxazolyl)-2-(carbomethoxy)thiophene-3-sulfonamide was prepared from 2-methoxycarbonylthiophene-3-sulfonyl chloride and 5-amino-3,4-dimethylisoxazole in dry pyridine.

The N-(4-haloisoxazolyl)sulfonamides can be prepared by condensation of amino-4-haloisoxazole with a sulfonyl chloride in THF with sodium hydride as a base. For example, N-(4-bromo-3-methyl-5-isoxazolyl)thiophene-2-sulfonamide was prepared from 5-amino-4-bromo-3-methylisoxazole and thiophene-2-sulfonyl chloride in THF and sodium hydride.

These sulfonamides also can be prepared from the corresponding sulfonyl chloride and the aminoisoxazole in pyridine with or without a catalytic amount of 4-dimethylaminopyridine (DMAP). In some cases, the bis-sulfonyl compound is obtained as the major or exclusive product. The bis-sulfonated products can be readily hydrolyzed to the sulfonamide using aqueous sodium hydroxide and a suitable co-solvent, such as methanol or tetrahydrofuran, generally at room temperature.

The substituted anilines may be synthesized by nitration of the appropriate precursor substituted benzene with, e.g., a mixture of nitric and sulfuric acid, or nitronium tetrafluoroborate. Reduction of the resulting aromatic nitro compound with, e.g., zinc powder, catalytic hydrogenation, stannous chloride, or any other method known to those of skill in the art, affords the desired aniline.

Coupling of the thienylcarboxylic acid with the aniline may be accomplished by conversion of the acid to the corresponding acyl imidazole (by reaction with, e.g., carbonyldiimidazole) or acyl chloride (by reaction with, e.g., oxalyl choride or thionyl chloride), followed by reaction with the aniline to give the desired arylaminocarbonylthiophene compounds.

Some of the compounds described herein are 3-sulfamoyl-2-benzylaminocarbonylthiophene derivatives. In preparing these compounds, the aniline in the above preparation is replaced with a benzylamine. Appropriate benzylamines may be synthesized by reaction of the corresponding benzyl halide with azide, followed by reduction of the resulting benzyl azide by, e.g., catalytic hydrogenation or treatment with a trialkyl- or triarylphosphine.

Other compounds described herein are 3-sulfamoyl-2-arylacetylthiophene derivatives. These compounds may be generated by addition of an appropriate benzylmagnesium halide to a 3-sulfamoyl-2-thienylcarboxylic acid derivative, such as an N-methyl-N-methoxyamide. This amide may be prepared by reaction of the acid with carbonyldiimidazole, followed by reaction with N-methyl-N-methoxyamine.

Prodrugs and other derivatives of the compounds suitable for administration to humans may also be designed and prepared by methods known to those of skill in the art (see, e.g., Nogrady (1985) *Medicinal Chemistry A Biochemical Approach,* Oxford University Press, New York, pages 388–392).

Compounds described herein have been synthesized and tested for activity in in vitro assays and, in some cases, in in vivo animal models. Nuclear magnetic resonance spectroscopic (NMR), mass spectrometric, infrared spectroscopic and high performance liquid chromatographic analyses indicated that the synthesized compounds have structures consistent with those expected for such compounds and are generally at least about 98% pure. All of the compounds exemplified or described herein exhibited activity as endothelin antagonists.

C. Evaluation of the Bioactivity of the Compounds

Standard physiological, pharmacological and biochemical procedures are available for testing the compounds to identify those that possess any biological activities of an endothelin peptide or the ability to interfere with or inhibit endothelin peptides. Compounds that exhibit in vitro activities, such as the ability to bind to endothelin receptors or to compete with one or more of the endothelin peptides for binding to endothelin receptors can be used in the methods for isolation of endothelin receptors and the methods for distinguishing the specificities of endothelin receptors, and are candidates for use in the methods of treating endothelin-mediated disorders.

Thus, other preferred compounds of formulas I and II, in addition to those specifically identified herein, that are endothelin antagonists or agonists may be identified using such screening assays.

1. Identifying Compounds that Modulate the Activity of an Endothelin Peptide

The compounds are tested for the ability to modulate the activity of endothelin-1. Numerous assays are known to those of skill in the art for evaluating the ability of compounds to modulate the activity of endothelin (see, e.g., U.S. Pat. No. 5,114,918 to Ishikawa et al.; EP A1 0 436 189 to BANYU PHARMACEUTICAL CO., LTD. (Oct. 7, 1991); Borges et al. (1989) *Eur. J. Pharm.* 165: 223–230; Filep et al. (1991) *Biochem. Biophys. Res. Commun.* 177: 171–176). In vitro studies may be corroborated with in vivo studies (see, e.g., U.S. Pat. No. 5,114,918 to Ishikawa et al.; EP A1 0 436 189 to BANYU PHARMACEUTICAL CO., LTD. (Oct. 7, 1991)) and pharmaceutical activity thereby evaluated. Such assays are described in the Examples herein and include the ability to compete for binding to $ET_A$ and $ET_B$ receptors present on membranes isolated from cell lines that have been genetically engineered to express either $ET_A$ or $ET_B$ receptors on their cell surfaces.

The properties of a potential antagonist may be assessed as a function of its ability to inhibit an endothelin induced activity in vitro using a particular tissue, such as rat portal vein and aorta as well as rat uterus, trachea and vas deferens (see e.g., Borges, R., Von Grafenstein, H. and Knight, D. E., "Tissue selectivity of endothelin," *Eur. J. Pharmacol* 165:223–230, (1989)). The ability to act as an endothelin antagonist in vivo can be tested in hypertensive rats, ddy mice or other recognized animal models (see, Kaltenbronn et al. (1990) *J. Med. Chem.* 33:838–845, see, also, U.S. Pat. No. 5,114,918 to Ishikawa et al.; and EP A1 0 436 189 to BANYU PHARMACEUTICAL CO., LTD (Oct. 7, 1991); see, also Bolger et al. (1983) *J. Pharmacol. Exp. Ther.* 225291–309). Using the results of such animal studies, pharmaceutical effectiveness may be evaluated and pharmaceutically effective dosages determined. A potential agonist may also be evaluated using in vitro and in vivo assays known to those of skill in the art.

Endothelin activity can be identified by the ability of a test compound to stimulate constriction of isolated rat thoracic aorta (Borges et al. (1989) "Tissue selectivity of endothelin" *Eur. J. Pharmacol.* 165: 223–230). To perform the assay, the endothelium is abraded and ring segments mounted under tension in a tissue bath and treated with endothelin in the presence of the test compound. Changes in endothelin induced tension are recorded. Dose response curves may be generated and used to provide information regarding the relative inhibitory potency of the test compound. Other tissues, including heart, skeletal muscle, kidney, uterus, trachea and vas deferens, may be used for evaluating the effects of a particular test compound on tissue contraction.

Endothelin isotype specific antagonists may be identified by the ability of a test compound to interfere with endothelin binding to different tissues or cells expressing different endothelin-receptor subtypes, or to interfere with the biological effects of endothelin or an endothelin isotype (Takayanagi et al. (1991) *Reg. Pep.* 32: 23–37, Panek et al. (1992) *Biochem. Biophys. Res. Commun.* 183: 566–571). For example, $ET_B$ receptors are expressed in vascular endothelial cells, possibly mediating the release of prostacyclin and endothelium-derived relaxing factor (De Nucci et al. (1988) *Proc. Natl. Acad. Sci. USA* 85:9797). $ET_A$ receptors are not detected in cultured endothelial cells, which express $ET_B$ receptors.

The binding of compounds or inhibition of binding of endothelin to $ET_B$ receptors can be assessed by measuring the inhibition of endothelin-1-mediated release of prostacyclin, as measured by its major stable metabolite, 6-keto $PGF_{1\alpha}$, from cultured bovine aortic endothelial cells (see, e.g., Filep et al. (1991) *Biochem. and Biophys Res. Commun.* 177: 171–176). Thus, the relative affinity of the compounds for different endothelin receptors may be evaluated by determining the inhibitory dose response curves using tissues that differ in receptor subtype.

Using such assays, the relative affinities of the compounds for $ET_A$ receptors and $ET_B$ receptors have been and can be assessed. Those that possess the desired properties, such as specific inhibition of binding of endothelin-1, are selected. The selected compounds that exhibit desirable activities may be therapeutically useful and are tested for such uses using the above-described assays from which in vivo effectiveness may be evaluated (see, e.g., U.S. Pat. Nos. 5,248,807; 5,240,910; 5,198,548; 5,187,195; 5,082,838; 5,230,999; published Canadian Application Nos. 2,067,288 and 2071193; published Great Britain Application No. 2,259,450; Published International PCT Application No. WO 93/08799; Benigi et al. (1993) *Kidney International* 44:440–444; and Nirei et al. (1993) *Life Sciences* 52:1869–1874). Compounds that exhibit in vitro activities that correlate with in vivo effectiveness will then be formulated in suitable pharmaceutical compositions and used as therapeutics.

The compounds also may be used in methods for identifying and isolating endothelin-specific receptors and aiding in the design of compounds that are more potent endothelin antagonists or agonists or that are more specific for a particular endothelin receptor.

2. Isolation of Endothelin Receptors

A method for identifying endothelin receptors is provided. In practicing this method, one or more of the compounds is linked to a support and used in methods of affinity purification of receptors. By selecting compounds with particular specificities, distinct subclasses of ET receptors may be identified.

One or more of the compounds may be linked to an appropriate resin, such as Affi-gel, covalently or by other linkage, by methods known to those of skill in the art for linking endothelin to such resins (see, Schvartz et al. (1990) *Endocrinology* 126: 3218–3222). The linked compounds can be those that are specific for $ET_A$ or $ET_B$ receptors or other subclass of receptors.

The resin is pre-equilibrated with a suitable buffer generally at a physiological pH (7 to 8). A composition containing solubilized receptors from a selected tissue are mixed with the resin to which the compound is linked and the receptors are selectively eluted. The receptors can be identified by testing them for binding to an endothelin isopeptide or analog or by other methods by which proteins are identified and characterized. Preparation of the receptors, the resin and the elution method may be performed by modification of standard protocols known to those of skill in the art (see, e.g., Schvartz et al. (1990) *Endocrinology* 126: 3218–3222).

Other methods for distinguishing receptor type based on differential affinity to any of the compounds herein are provided. Any of the assays described herein for measuring the affinity of selected compounds for endothelin receptors may also be used to distinguish receptor subtypes based on affinity for particular compounds provided herein. In particular, an unknown receptor may be identified as an $ET_A$ or $ET_B$ receptor by measuring the binding affinity of the unknown receptor for a compound provided herein that has a known affinity for one receptor over the other. Such preferential interaction is useful for determining the particular disease that may be treated with a compound prepared as described herein. For example, compounds with high affinity for $ET_A$ receptors and little or no affinity for $ET_B$ receptors are candidates for use as hypertensive agents; whereas, compounds that preferentially interact with $ET_B$ receptors are candidates for use as anti-asthma agents.

D. Formulation and Administration of the Compositions

Formulations of the sulfonamides are provided herein. The formulations are compositions designed for administration of the pharmaceutically acceptable derivatives, particularly salts of the sulfonamide compounds provided herein. Because of the observed superior stability characteristics of the salts, compared to the neutral forms, such salts, particularly the sodium salts, are particularly suitable for oral and parenteral administration. Such compositions include solutions, suspensions, tablets, dispersible tablets, pills, capsules, powders, sustained release formulations and any other suitable formulation. Preferably the compositions will take the form of a pill or tablet. Methods for manufacture of tablets, capsules and other such formulations are known to those of skill in the art (see, e.g., Ansel, H. C (1985) *Introduction to Pharmaceutical Dosage Forms,* 4th Edition, pp. 126–163).

In the formulations, effective concentrations of one or more pharmaceutically acceptable derivatives is (are) mixed with a suitable pharmaceutical carrier or vehicle. Preferably, the sulfonamide compounds are derivatized as the corresponding salts, preferably sodium salts, prior to formulation, as described above. The concentrations of the salts of the compounds in the formulations are effective for delivery of an amount, upon administration, that ameliorates the symptoms of the endothelin-mediated disease. Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated.

Pharmaceutical carriers or vehicles suitable for administration of the compounds provided herein include any such carriers known to those skilled in the art to be suitable for the particular mode of administration. In addition, the compounds may be formulated as the sole pharmaceutically active ingredient in the composition or may be combined with other active ingredients. Liposomal suspensions, including tissue-targeted liposomes, may also be suitable as pharmaceutically acceptable carriers. These may be prepared according to methods known to those skilled in the art. For example, liposome formulations may be prepared as described in U.S. Pat. No. 4,522,811.

The active compound as salt, preferably as a sodium salt, is included in the pharmaceutically acceptable carrier in an amount sufficient to exert a therapeutically useful effect in the absence of undesirable side effects on the patient treated. The therapeutically effective concentration may be determined empirically by testing the compounds in known in vitro and in vivo systems (see, e.g., U.S. Pat. No. 5,114,918 to Ishikawa et al.; EP A1 0 436 189 to BANYU PHARMACEUTICAL CO., LTD (Oct. 7, 1991); Borges et al. (1989) *Eur. J. Pharm.* 165: 223–230;: Filep et al. (1991) *Biochem. Biophys. Res. Commun.* 177: 171–176) and then extrapolated therefrom for dosages for humans.

The concentration of active compound sodium salt in the drug composition will depend on absorption, inactivation and excretion rates of the active compound, the physicochemical characteristics of the compound, the dosage schedule, and amount administered as well as other factors known to those of skill in the art. For example, the amount that is delivered is sufficient to treat the symptoms of hypertension. The effective amounts for treating endothelin-mediated disorders are expected to be higher than the amount of the sulfonamide compound that would be administered for treating bacterial infections.

Typically a therapeutically effective dosage should produce a serum concentration of active ingredient of from about 0.1 ng/ml to about 50–100 $\mu$g/ml. The pharmaceutical compositions typically should provide a dosage of from about 0.001 mg to about 2000 mg of compound per kilogram of body weight per day. Pharmaceutical dosage unit forms are prepared to provide from about 1 mg to about 1000 mg and preferably from about 10 to about 500 mg of the essential active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Preferred pharmaceutically acceptable derivatives include acids, salts, esters, hydrates, solvates and prodrug forms. The derivative is selected to be a more stable form than the corresponding neutral compound. Preferred are pharmaceutically-acceptable salts. More preferred salts include alkali metal salts, particularly sodium salts, such as, but not limited to, a sodium hydrogen phosphate salt and a sodium salt, most preferrably the sodium salt.

Thus, effective concentrations or amounts of one or more of the compounds provided herein or pharmaceutically acceptable derivatives thereof are mixed with a suitable pharmaceutical carrier or vehicle for systemic, topical or local administration to form pharmaceutical compositions. Compounds are included in an amount effective for ameliorating or treating the endothelin-mediated disorder for which treatment is contemplated. The concentration of active compound in the composition will depend on absorption, inactivation, excretion rates of the active compound, the dosage schedule, amount administered, particular formulation as well as other factors known to those of skill in the art.

The compositions are intended to be administered by an suitable route, which includes orally, parenterally, rectally and topically and locally depending upon the disorder being treated. For example, for treatment of ophthalmic disorders, such as glaucoma, formulation for intraocular and also intravitreal injection is contemplated. For oral administration, capsules and tablets are presently preferred. For parenteral administration reconstitution of a lyophilized powder, prepared as described herein, is preferred. The compounds in liquid, semi-liquid or solid form and are formulated in a manner suitable for each route of administration. Preferred modes of administration include parenteral and oral modes of administration.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as tween, or dissolution in aqueous sodium bicarbonate. Derivatives of the compounds, such as prodrugs of the compounds may also be used in formulating effective pharmaceutical compositions.

Upon mixing or addition of the sodium salt of the sulfonamide compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The formulations are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these formulations are known to those skilled in the art. he contemplated compositions may contain 0.001 %–100% active ingredient, preferably 0.1–85%, typically 75–95%.

The salts, preferably sodium salts, of the active compounds may be prepared with carriers that protect the compound against rapid elimination from the body, such as time release formulations or coatings.

The formulations may be include other active compounds to obtain desired combinations of properties. The compounds of formula I, or a pharmaceutically acceptable salts and derivatives thereof as described herein, may also be advantageously administered for therapeutic or prophylactic purposes together with another pharmacological agent known in the general art to be of value in treating one or more of the diseases or medical conditions referred to hereinabove, such as beta-adrenergic blocker (for example atenolol), a calcium channel blocker (for example nifedipine), an angiotensin converting enzyme (ACE) inhibitor (for example lisinopril), a diuretic (for example furosemide or hydrochlorothiazide), an endothelin converting enzyme (ECE) inhibitor (for example phosphoramidon), a neutral endopeptidase (NEP) inhibitor, an HMGCoA reductase inhibitor, a nitric oxide donor, an anti-oxidant, a vasodilator, a dopamine agonist, a neuroprotective agent, a steroid, a beta-agonist, an anti-coagulant, or a thrombolytic agent. It is to be understood that such combination therapy constitutes a further aspect of the compositions and methods of treatment provided herein.

1. Formulations for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as sodium cyclamate and saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the salt of the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. For example, if the compound is used for treating asthma or hypertension, it may be used with other bronchodilators and antihypertensive agents, respectively. The active ingredient is a compound or salt thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substance used in effervescent granules, to be reconstituted into a liquid oral dosage form, include organic adds and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and other such carriers, and encapsulating these solutions or suspensions in hard or soft gelatin capsule shells. Other useful formulations include those set forth in U.S. Pat. Nos. Re 28,819 and 4,358,603.

In one embodiment, the formulations are solid dosage forms, preferably capsules or tablets. In a preferred embodiment, the formulations are solid dosage forms, preferably capsules or tablets, containing 10–100%, preferably 50–95%, more preferably 75–85%, most preferably 80–85%, by weight, of one or more sulfonamides or sulfonamide salts, preferably sodium hydrogen phosphate or sodium salts, more preferably the sodium salts, of one or more sulfonamide compounds of formula I; about 0–25%, preferably 8–15%, of a diluent or a binder, such as lactose or microcrystalline cellulose; about 0 to 10%, preferably about 0–7%, of a disintegrant, such as a modified starch or cellulose polymer, particularly a cross-linked sodium carboxymethyl cellulose, such as crosscarmellose sodium (Crosscarmellose sodium NF is available commercially under the name AC-DI-SOL, FMC Corporation, Philadelphia, Pa.) or sodium starch glycolate; and 0–2% of a lubricant, such a magnesium stearate, talc and calcium stearate. The disintegrant, such as crosscarmellose sodium or sodium starch glycolate, provides for rapid break-up of the cellulosic matrix for immediate release of active agent following dissolution of coating polymer. In all embodiments, the precise amount of active ingredient and auxilliary ingredients can be determined empirically and is a function of the route of administration and the diorder that is treated.

In an exemplary embodiment, the formulations are capsules containing about 50%–100%, preferably about 70–90%, more preferably about 80–90%, most preferably about 83% of one or more sodium salts of one or more sulfonamide compounds of formula I; about 0–15%, preferably about 11% of a diluent or a binder, such as lactose or microcrystalline cellulose; about 0–10%, preferably about 5% of a disintegrant, such as crosscarmellose sodium or sodium starch glycolate; and about 0 to 5%, preferably about 1% of a lubricant, such as magnesium stearate. Solid forms for administration as tablets are also contemplated herein.

In an exemplary preferred embodiment, the formulations are capsules containing 83% of one or more sodium salts of one or more sulfonamide compounds; 11% of microcrystalline cellulose; 5% of a disintegrant, such as Crosscarmellose sodium or sodium starch glycolate; and 1% of magnesium stearate.

The above embodiments may also be formulated in the form of a tablet, which may optionally be coated. Tablets will contain the compositions described herein.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (Tween 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is know and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

In many instances, the solutions of sodium salts, including the sodium salt and sodium hydrogen phosphate salts exhibit compared to the neutral compound. These salts also exhibit improved solubility over the neutral compound in aqueous media. The sodium salt was found, in certain aqueous formulations, to be as stable as the sodium hydrogen phosphate salt.

3. Lyophilized Powders

Of particular interest herein are lyophilized powders, which can be reconstituted for administration as solutions, emulsions and other mixtures. They may also be reconstituted and formulated as solids or gels.

In particular embodiments, formulations of sodium hydrogen phosphate or sodium, preferably sodium, salts of the sulfonamide compounds, which possess increased stability relative to formulations of the neutral sulfonamides are provided. Specifically, formulation of sulfonamide sodium salts as a sterile, lyophilized powder are provided. These powders were found to have increased stability relative to formulations of the neutral sulfonamides.

The sterile, lyophilized powder is prepared by dissolving the sodium salt in a sodium phosphate buffer solution containing dextrose or other suitable excipient. Subsequent sterile filtration of the solution followed by lyophilization under standard conditions known to those of skill in the art provides the desired formulation. Briefly, the lyophilized powder is prepared by dissolving dextrose, sorbital, fructose, corn syrup, xylitol, glycerin, glucose, sucrose or other suitable agent, about 1–20%, preferably about 5 to 15%, in a suitable buffer, such as citrate, sodium or potassium phosphate or other such buffer known to those of skill in the art at, typically, about neutral pH. Then, a selected salt, preferably the sodium salt of the sulfonamide (about 1 gm of the salt per 10–100 gms of the buffer solution, typically about 1 gm/30 gms), is added to the resulting mixture, preferably above room temperature, more preferably at about 30–35° C., and stirred until it dissolves. The resulting mixture is diluted by adding more buffer (so that the resulting concentration of the salt decreases by about 10–50%, typically about 15–25%). The resulting mixture is sterile filtered or treated to remove particulates and to insure sterility, and apportioned into vials for lyophilization. Each vial will contain a single dosage (100–500 mg, preferably 250 mg) or multiple dosages of the sulfonamide salt. The lyophilized powder can be stored under appropriate conditions, such as at about 4° C. to room temperature. Details of an exemplary procedure are set forth in the Examples.

Reconstitution of this lyophilized powder with water for injection provides a formulation for use in parenteral administration of sodium salts of the sulfonamides. For reconstitution about 1–50 mg, preferably 5–35, more preferably about 9–30 is added per ml of sterile water or other suitable carrier. The precise amount depends upon the indication treated and selected compound. Such amount can be empirically determined.

In one embodiment, the formulations contain lyophilized solids containing one or more sodium hydrogen phosphate or sodium, preferably sodium, salts of one or more sulfonamide compounds of formula I, and also contain one or more of the following:

a buffer, such as sodium or potassium phosphate, or citrate;
a solubilizing agent, such as LABRASOL, DMSO, bis (trimethylsilyl)acetamide, ethanol, propyleneglycol (PG), or polyvinylpyrrolidine (PVP); and
a sugar, such as sorbitol or dextrose.

In more preferred embodiments, the formulations contain one or more sodium hydrogen phosphate or sodium, preferably sodium, salts of one or more sulfonamide compounds of formula I; a buffer, such as sodium or potassium phosphate, or citrate; and a sugar, such as sorbitol or dextrose.

In the most preferred embodiments, the formulations contain one or more sodium salts of one or more sulfonamide compounds of formula I; a sodium phosphate buffer; and dextrose.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The sodium salts and other derivatives of the compounds may be formulated as aerosols for topical application, such as by inhalation (see, e.g., U.S. Pat. Nos. 4,044,126, 4,414, 209, and 4,364,923, which describe aerosols for delivery of a steroid useful for treatment inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically diameters of less than 50 microns, preferably less than 10 microns.

The sodium salts of the compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%–10% isotonic solutions, pH about 5–7, with appropriate salts.

5. Articles of Manufacture

Finally, the derivatives, particularly the salts, acids, esters and prodrugs, preferably the sodium salts, of the compounds may be packaged as articles of manufacture containing packaging material, a salt, acid, ester or prodrug, preferably a sodium salt, of a compound provided herein, which is effective for antagonizing the effects of endothelin, ameliorating the symptoms of an endothelin-mediated disorder, or inhibiting binding of an endothelin peptide to an ET receptor with an $IC_{50}$ of less than about 10 $\mu$M, within the packaging material, and a label that indicates that the compound or salt thereof is used for antagonizing the effects of endothelin, treating endothelin-mediated disorders or inhibiting the binding of an endothelin peptide to an ET receptor.

6. Formulations for Other Routes of Administration

Depending upon the condition treated other routes of administration, such as topical application, transdermal patches, an rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

The following examples are included for illustrative purposes only and are not intended to limit the scope of the invention.

EXAMPLE 1

Methyl 2-(3-(3-(4-Chloro-3-methyl-5-isoxazolylsulfamoyl)-2-thienylcarboxamido)-2,4,6-trimethylphenyl)acetate A. Methyl 3-Amino-2,4,6-trimethylphenylacetate To a solution of 3-cyanomethyl-2,4,6-trimethylaniline (see Example 14, procedure C) (5 g, 28.7 mmol) in methanol (30 mL) was added concentrated sulfuric acid (30 mL) with cooling. The resulting mixture was heated under reflux for 8 h before it was allowed to cool to rt and diluted with water (100 mL). The mixture was stripped off methanol and the residue was basified with sodium carbonate and then extracted with ethyl acetate. The organic layer was worked up and concentrated as usual to give the desired compound as an oil (5.2 g, 88%).

B. Methyl 2-(3-(3-(4-Chloro-3-methyl-5-isoxazolylsulfamoyl)-2-thienylcarboxamido)-2,4,6-trimethylphenyl)acetate To a solution of N-(4-chloro-3-methyl-5-isoxazolyl)-3-sulfamoylthiophene-2-carboxylic acid (1 g, 3.1 mmol) in anhydrous N,N-dimethylformamide (20 mL) was added 1,1'-carbonyldiimidazole (553 mg, 3.41 mmol). After the gas evolution ceased, methyl 3-amino-2,4,6-trimethylphenylacetate (3.1 g, 15 mmol) was added and the resulting mixture was heated at 80° C. for 24 h. The mixture was allowed to cool to room temperature and poured to cold 0.5 M HCl (100 mL). The resulted precipitate was filtered and then purified by HPLC to give the desired compound as solid (mp 75–78° C., 238 mg, 15%).

EXAMPLE 2

2-(3-(3-(4-Chloro-3-methyl-5-isoxazolylsulfamoyl)-2-thienylcarboxamido)-2,4,6-trimethylphenyl)acetic acid A solution of methyl 2-(3-(3-(4-chloro-3-methyl-5-isoxazolylsulfamoyl)-2-thienylcarboxamido)-2,4,6-trimethylphenyl)acetate (100 mg, 0.195 mmol) (Example 1) in 1N NaOH (50 mL) was stirred at rt for 4 h before it was acidified with concentrated HCl to pH-1.2. The resulted white precipitate was filtered and dried on lyophilizer to give 2-(3-(3-(4-chloro-3-methyl-5-isoxazolylsulfamoyl)-2-thienylcarboxamido)-2,4,6-trimethylphenyl)acetic acid as a white solid (mp 110–113° C., 74 mg, 76%).

EXAMPLE 3

$N^2$-(3-dimethylaminomethyl-2,4,6-trimethylphenyl)-3-(4-chloro-3-methyl-5-isoxazolylsulfamoyl)-2-thiophenecarboxamide trifluoroacetate A. 3-Dimethylaminomethyl-2,4,6-trimethylaniline To a mixture of THF (20 mL) and dimethylamine (20 mL, 40% wt in water) at 0° C. was added 2,4,6-trimethylbenzyl chloride (5 g, 29.64 mmol). The mixture was allowed to warm up to room temperature and stirred for 4 h before THF was evaporated and the aqueous residue was extracted with ether. The organic layer was worked up and concentrated as usual to give 2,4,6-trimethylphenyl-dimethylamine in quantitative yield. This compound was then nitrated and the resulted nitro compound reduced to the corresponding aniline as demonstrated in Example 14.

B. $N^2$-(3-dimethylaminomethyl-2,4,6-trimethylphenyl)-3-(4-chloro-3-methyl-5-isoxazolylsulfamoyl)-2-thiophenecarboxamide trifluoroacetate $N^2$-(3-dimethylaminomethyl-2,4,6-trimethylphenyl)-3-(4-chloro-3-methyl-5-isoxazolylsulfamoyl)-2-thiophenecarboxamide trifluoroacetate was synthesized and purified in the same fashion as for Example 1 as a powder (mp 92–94° C., 18% yield).

EXAMPLE 4

$N^2$-(3-Methanesulfonamido-2,4,6-trimethyl)phenyl-3-(4-chloro-3-methyl-5-isoxazolyl)-2-thiophenecarboxamide A. 3-Methanesulfamido-2,4,6-trimethylaniline To a solution of 2,4,6-trimethyl-1,3-phenylenediamine (5.82 g, 38.76 mmol) and triethylamine (3.6 mL, 25.84 mmol) in ethyl acetate (100 mL) at 0° C. was added methanesulfonyl chloride (2 mL, 25.84 mmol) dropwise. The mixture was stirred overnight. The resulted precipitate was filtered off and the filtrate was concentrated. The resulted solid was recrystallized from MeOH to give the desired product (3 g, 50% yield).

B. $N^2$-(3-Methanesulfonamido-2,4,6-trimethyl)phenyl-3-(4-chloro-3-methyl-5-isoxazolyl)-2-thiophenecarboxamide $N^2$-(3-Methanesulfonamido-2,4,6-trimethyl)phenyl-3-(4-chloro-3-methyl-5-isoxazolyl)-2-thiophenecarboxamide was synthesized and purified in the same fashion as in Example 1 as a powder (mp 130–133° C., 19% yield).

EXAMPLE 5

N-(4-Chloro-3-methyl-5-isoxazolyl)-2-(2,4-dimethyl-6-aminocarbonylphenylaminocarbonyl)thiophene-3-sulfonamide A. 2-Cyano-4,6-dimethylaniline To a solution of 2,4-dimethylaniline (9.80 g, 80.9 mmol) in dichloromethane (200 mL) at 0° C. was added N-bromosuccinimide (15.1 g, 84.9 mmol) slowly. The mixture was allowed to warmed to room temperature and stirred at room temperature overnight before it was washed with 1 N NaOH. The organic layer was worked up and concentrated as usual. The residue was dissolved in N,N-dimethylformamide (120 mL) followed by the addition of cuprous cyanide (14.5 g, 161.8 mmol). The mixture was heated under reflux for 8 h and then allowed to cool to rt and poured into water (1 L). The mixture was treated with excess ethylenediamine and the precipitate was filtered, redissolved in ethyl acetate, dried with $MgSO_4$ and then concentrated to give the desired compound as an oil (6.7 g, 55%).

B. N-(4-Chloro-3-methyl-5-isoxazolyl)-2-(2,4-dimethyl-6-aminocarbonylphenylaminocarbonyl)thiophene-3-sulfonamide N-(4-Chloro-3-methyl-5-isoxazolyl)-2-(2,4-dimethyl-6-aminocarbonylphenylaminocarbonyl)thiophene-3-sulfonamide was synthesized and purified in the same fashion as for Example 14. The cyano group was hydrolyzed to the corresponding amide during deprotection of the MOM group. N-(4-Chloro-3-methyl-5-isoxazolyl)-2-(2,4-dimethyl-6-aminocarbonylphenylaminocarbonyl)thiophene-3-sulfonamide was obtained as a solid (mp 40–43° C., 61%).

EXAMPLE 6

$N^2$-(3-Hydroxy-2,4,6-trimethyl)phenyl-3-(4-chloro-3-methyl-5-isoxazolyl)sulfamoyl-2-thiophenecarboxamide A. 3-Acetoxy-2,4,6-trimethylaniline To a solution of 2,4,6-trimethylphenol (10 g, 73.5 mmol) and triethylamine (11.1 g, 110.3 mmol) in ethyl acetate (200 mL) was added acetyl chloride (7.5 g, 95.6 mmol) dropwise at 0° C. The mixture was stirred overnight. The reaction was quenched with water and the organic layer was washed with 1 N HCl. The organic layer was dried and concentrated as usual. The residue was nitrated Example 14 (procedure B) and reduced as demonstrated for Example 14 (procedure C) to give 3-acetoxy-2,4,6-trimethylaniline.

B. $N^2$-(3-Hydroxy-2,4,6-trimethyl)phenyl-3-(4-chloro-3-methyl-5-isoxazolyl)sulfamoyl-2-thiophenecarboxamide $N^2$-(3-Hydroxy-2,4,6-trimethyl)phenyl-3-(4-chloro-3-methyl-5-isoxazolyl)sulfamoyl-2-thiophenecarboxamide was synthesized and purified in the same fashion as for Example 14. The acetoxy group was hydrolyzed to the corresponding hydroxyl during deprotection of the MOM group. $N^2$-(3-Hydroxy-2,4,6-trimethyl)phenyl-3-(4-chloro-3-methyl-5-isoxazolyl)sulfamoyl-2-thiophenecarboxamide was obtained as a solid (mp 75–78° C., 54%).

EXAMPLE 7

3-(4-Chloro-3-methyl-5-isoxazolyl)sulfamoyl-$N^2$-(3-carboxyl-2,4,6-trimethylphenyl)-2-thiophenecarboxamide A. Allyl 3-amino-2,4,6-trimethylbenzoate To a solution of 2,4,6-trimethylbenzoic acid (10 g, 61 mmol) in DMF (100 mL) were sequentially added potassium carbonate (17 g, 122 mmol) and allyl bromide (11 g, 91.5 mmol). The mixture was stirred at rt overnight before it was poured into water (~1 L). The resulted precipitate was filtered and washed with water, then dried in vacuo to give allyl 2,4,6-trimethylbenzoate as a solid (10.2 g, 82%) which was nitrated and then reduced as shown for Example 14 (procedure B and C) to give allyl 3-amino-2,4,6-trimethylbenzoate.

B. 3-(4-Chloro-3-methyl-5-isoxazolyl)sulfamoyl-$N^2$-(3-carboxyl-2,4,6-trimethylphenyl)-2-thiophenecarboxamide 3-(4-Chloro-3-methyl-5-isoxazolyl)sulfamoyl-$N^2$-(3-carboxyl-2,4,6-trimethylphenyl)-2-thiophenecarboxamide was synthesized and purified in the same fashion as for Example 14. The allyl group was deprotected using a literature procedure. 3-(4-Chloro-3-methyl-5-isoxazolyl) sulfamoyl-$N^2$-(3-carboxyl-2,4,6-trimethylphenyl)-2-thiophenecarboxamide was obtained as a solid (mp 179–181° C., 24%).

EXAMPLE 8

3-(4-Chloro-3-methyl-5-isoxazolyl)sulfamoyl-$N^2$-(2-carboxyl-4,6-dimethyl)phenyl-2-thiophenecarboxamide 3-(4-Chloro-3-methyl-5-isoxazolyl)sulfamoyl-$N^2$-(2-carboxyl-4,6-dimethyl)phenyl-2-thiophenecarboxamide was synthesized and purified in the same fashion as for Example 14 using 2-amino-3,4-dimethylbenzoic acid. 3-(4-Chloro-3-methyl-5-isoxazolyl)sulfamoyl-$N^2$-(2-carboxyl-4,6-dimethyl)phenyl-2-thiophenecarboxamide was obtained as a solid (mp 171–174° C., 66%).

EXAMPLE 9

3-(4-Chloro-3-methyl-5-isoxazolyl)sulfamoyl-$N^2$-(2-phenyl-4,6-dimethyl)phenyl-2-thiophenecarboxamide A. 2-Amino-3,5-dimethylbiphenyl 2-Bromo-4,6-dimethylaniline was coupled with phenyl boronic acid under Suzuki conditions to give 2-amino-3,5-dimethylbiphenyl in 68% yield.

B. 3-(4-Chloro-3-methyl-5-isoxazolyl)sulfamoyl-$N^2$-(2-phenyl-4,6-dimethyl)phenyl-2-thiophenecarboxamide 3-(4-Chloro-3-methyl-5-isoxazolyl)sulfamoyl-$N^2$-(2-phenyl-4,6-dimethyl)phenyl-2-thiophenecarboxamide was synthesized and purified in the same fashion as in Example 14. 3-(4-Chloro-3-methyl-5-isoxazolyl)sulfamoyl-$N^2$-(2-phenyl-4,6-dimethyl)phenyl-2-thiophenecarboxamide was obtained as a solid (mp 178–181° C., 59%).

EXAMPLE 10

3-(4-Chloro-3-methyl-5-isoxazolyl)sulfamoyl-$N^2$-(3-sulfamoyl-2,4,6-trimethyl)phenyl-2-thiophenecarboxamide A. 3-Sulfamoyl-2,4,6-trimethylaniline To a solution of mesitylenesulfonyl chloride (5 g, 22.9 mmol) in THF (50 mL) at 0° C. was added ammonium hydroxide (20 mL). The mixture was stirred at rt for 30 min before all the volatiles were evaporated. The resulted white solid was filtered off water and nitrated and reduced as demonstrated in Example 14 (procedure B and C) to give 3-sulfamoyl-2,4,6-trimethylaniline in 47% yield.

B. 3-(4-Chloro-3-methyl-5-isoxazolyl)sulfamoyl-$N^2$-(3-sulfamoyl-2,4,6-trimethyl)phenyl-2-thiophenecarboxamide 3-(4-Chloro-3-methyl-5-isoxazolyl)sulfamoyl-$N^2$-(3-sulfamoyl-2,4,6-trimethyl)phenyl-2-thiophenecarboxamide was synthesized and purified in the same fashion as in Example 14. 3-(4-Chloro-3-methyl-5-isoxazolyl)sulfamoyl-$N^2$-(3-sulfamoyl-2,4,6-trimethyl)phenyl-2-thiophenecarboxamide was obtained as a solid (mp 214–217° C., 69%).

EXAMPLE 11

N-(4-Chloro-3-methyl-5-isoxazolyl)-2-(pentamethylphenylaminocarbonyl)thiophene-3-sulfonamide A. Pentamethylaniline To a solution of pentamethylbenzene (5 g, 33.8 mmol) in dichloromethane (250 mL) at 0° C. was quickly added nitronium tetrafluoroborate (5 g). The mixture was stirred for 4 h before it was quenched with cold water. The organic layer was concentrated and the residue was reduced (Example 14, procedure C) to give pentamethylaniline in 52% yield.

B. N-(4-Chloro-3-methyl-5-isoxazolyl)-2-(pentamethylphenylaminocarbonyl)thiophene-3-sulfonamide N-(4-Chloro-3-methyl-5-isoxazolyl)-2-(pentamethylphenylaminocarbonyl)thiophene-3-sulfonamide was synthesized and purified in the same fashion as in Example 14. N-(4-Chloro-3-methyl-5-isoxazolyl)-2-(pentamethylphenylaminocarbonyl)thiophene-3-sulfonamide was obtained as a solid (mp 196–198° C., 69%).

EXAMPLE 12

N-(4-Chloro-3-methyl-5-isoxazolyl)-2-(2,4,6-trimethylphenylmethylaminocarbonyl)thiophene-3-sulfonamide

A. 2,4,6-Trimethylbenzylamine

To a solution of 2,4,6-trimethylbenzyl chloride (5 g, 29.7 mmol) in DMSO (20 mL) was added sodium azide (2.9 g, 44.6 mmol). The mixture was heated at 60° C. for 3 h before it was allowed to cool to rt and poured to water (200 mL). The resulted precipitate was filtered dissolved in wet THF (50 mL) followed by the addition of triphenylphosphine (15.6, 59.4 mmol). The mixture was heated under reflux for 3 h and the volatiles were evaporated. The residue was added to 1 N HCl (200 mL) and the solids were filtered off. The filtrate was basified and the resulted precipitate was filtered, dried under vacuum to give 2,4,6-trimethylbenzylamine (2.7 g, 61 % yield).

B. N-(4-Chloro-3-methyl-5-isoxazolyl)-2-(2,4,6-trimethylphenylmethylaminocarbonyl)thiophene-3-sulfonamide

N-(4-Chloro-3-methyl-5-isoxazolyl)-2-(2,4,6-trimethylphenylmethylaminocarbonyl)thiophene-3-sulfonamide was synthesized and purified in the same fashion as in Example 14. N-(4-Chloro-3-methyl-5-isoxazolyl)-2-(2,4,6-trimethylphenylmethylaminocarbonyl)thiophene-3-sulfonamide was obtained as a solid (mp 175–177° C., 73%).

EXAMPLE 13

N-(4-Chloro-3-methyl-5-isoxazolyl)-2-(3-cyanomethyl-2,4,6-trimethylphenylmethylaminocarbonyl)thiophene-3-sulfonamide

A. 3-Cyanomethyl-2,4,6-trimethylbenzylamine

To a solution of 1,3-bis(chloromethyl)-2,4,6-trimethylbenzene (10 g, 46 mmol) in DMSO (30 mL) was added sodium cyanide (2.25 g, 46 mmol). The mixture was stirred at rt overnight before sodium azide (4.5 g, 69 mmol) was added. The mixture was heated at 80° C. for 3 h before it was poured into water (300 mL). The resulting precipitate was filtered to give a 2:1:1.5 mixture of 3-cyanomethyl-2,4,6-trimethylbenzyl azide, 1,3-bis(cyanomethyl)-2,4,6-trimethylbenzene and 1,3-bis(azidomethyl)-2,4,6-trimethylbenzene. This mixture was not separated but was treated with triphenylphosphine (18 g, 69 mmol) in wet THF. The reaction was conducted and worked up as in Example 12 (procedure A) only that the HCl solution was basified with $K_2CO_3$ until no more gas evolution observed. The mixture was extracted with dichloromethane and concentrated to give only the desired 3-cyanomethyl-2,4,6-trimethylbenzylamine (2 g, 25% yield).

B. N-(4-Chloro-3-methyl-5-isoxazolyl)-2-(3-cyanomethyl-2,4,6-trimethylphenylmethylaminocarbonyl)thiophene-3-sulfonamide

N-(4-Chloro-3-methyl-5-isoxazolyl)-2-(3-cyanomethyl-2,4,6-trimethylphenylmethylaminocarbonyl)thiophene-3-sulfonamide was synthesized and purified in the same fashion as in Example 14. N-(4-Chloro-3-methyl-5-isoxazolyl)-2-(3-cyanomethyl-2,4,6-trimethylphenylmethylaminocarbonyl)thiophene-3-sulfonamide was obtained as a solid (mp 76–79 ° C., 53%).

EXAMPLE 14

N-(3-Cyanomethyl-2,4,6-trimethylphenyl)-3-(4-chloro-3-methyl-5-isoxazolylsulfamoyl)-2-thiophenecarboxamide, N (sulfonamide)-Na-salt

A. 2,4,6-Trimethylphenylacetonitrile

To a mixture of α-chloroisodurene (5 g, 29.64 mmol) and sodium cyanide (5.8 g, 118.6 mmol) was added anhydrous DMSO (16 mL). The exothermic reaction was stirred until the reaction mixture was a room temperature again, then heated at 80° C. for 30 min. To work up the reaction mixture was poured into water (200 mL). The resulted white precipitate was filtered, washed with water, dried to give 2,4,6-trimethylphenylacetonitrile as a white powder (4.5 g, 95%).

B. 3-Cyanomethyl-1-nitro-2,4,6-trimethylbenzene

To a suspension of 2,4,6-trimethylphenylacetonitrile (4.5 g) in acetic acid (40 mL) at RT was added dropwise 70% $HNO_3$ (20 mL) and conc. $H_2SO_4$ (5 mL). The brown reaction mixture was stirred for 1 h, poured into ice-water (500 mL). The product was extracted into ethyl acetate, the extract was washed with water, dried over $MgSO_4$ and concentrated to give 3-cyanomethyl-1-nitro-2,4,6-trimethylbenzene as an oil (5.8 g, quantitative yield).

C. 3-Cyanomethyl-2,4,6-trimethylaniline

To a solution of 3-cyanomethyl-1-nitro-2,4,6-trimethylbenzene (5.8 g in methanol (150 mL) were sequentially added ammonium chloride (6 g in 50 mL of water), zinc powder (6 g). The exothermic reaction was vigorously stirred until it was back to RT (2 h). To work up the crude mixture was filtered off and the cake was washed with methanol. The methanolic solutions were concentrated and the residue partitioned between ethyl acetate and 1N NaOH. The organic layer was dried over $MgSO_4$ and concentrated to give 3-cyanomethyl-2,4,6-trimethylaniline as a light brown solid (3.4 g, 69%).

D. 5-Amino-4-chloro-3-methylisoxazole

To a solution of 5-Amino-3-methylisoxazole (9.8 g, 100 mmol) in methylene chloride (200 mL) was added N-Chlorosuccinimide (14.7 g, 110 mmol) at 0° C. over the period of 20 min. The reaction mixture was stirred for 2 h at RT. To work up the reaction mixture was concentrated and partitioned between 1N NaOH (150 mL)/ethyl acetate (400 mL). The organic layer was washed with 1N NaOH, water, brine, dried over $MgSO_4$ then concentrated to a brown solid. For purification the product was reprecipitated from chloroform/hexane then recrystallized from ethyl acetate/hexane to give 5-amino-4-chloro-3-methylisoxazole as a brownish solid (5.5 g, 41%).

E. 2-Carbomethoxy-3-[N-(4-chloro-3-methylisoxazol-5-yl)]thiophenesulfonamide

To a slurry of 60% mineral oil suspension of NaH (8.5 g, 0.21 mol) in THF (100 mL) at −20° C. was added a solution of 5-amino-4-chloro-3-methylisoxazole (12.4 g, 92.4 mmol) in anhydrous THF (65 mL) under nitrogen over a period of 20 min. After 10 min stirring was added a solution of 2-Carbomethoxy-3-thiophenesulfonyl chloride (22.2 g, 92.4 mmol) in THF (65 mL) at −20° C. over 15 min. The reaction mixture was stirred for 10 min then quenched with $H_2O$ (5 mL) at the same temperature. To work up the reaction mixture was poured into 4N HCl and the product was extracted with ethyl acetate. The combined organics were washed with water then the compound was extracted with half-saturated $NaHCO_3$. The combined basic solutions were decolorized with activated charcoal, cooled to 0° C. and acidified with 4N HCl. The product was isolated by filtration, washed with water, dried to give 2-carbomethoxy-3-[N-(4-chloro-3-methylisoxazol-5-yl)]thiophenesulfonamide as a white powder (23.4 g, 75%).

F. 2-Carbomethoxy-3-[N-(4-chloro-3-methylisoxazol-5-yl)-N-MOM]thiophenesulfonamide To a solution of 2-carbomethoxy-3-[N-(4-chloro-3-methylisoxazol-5-yl)]thiophenesulfonamide (3.3 g, 10.0 mmol) in THF (50 mL) diisopropyl ethyl amine (1.99 g, 15.0 mmol) was added at 0° C. followed by addition of bromomethyl methyl ether (1.5 g, 12.0 mmol). The reaction mixture was stirred overnight at RT. To work up the reaction mixture was concentrated and partitioned between water and ethyl acetate. The organic layer was washed with water, brine, dried over MgSO$_4$, concentrated to give 2-carbomethoxy-3-[N-(4-chloro-3-methylisoxazol-5-yl)-N-MOM]thiophenesulfonamide as a greenish oil (3.5 g, 90%).

G. 2-Carboxy-3-[N-(4-chloro-3-methylisoxazol-5-yl)-N-MOM]thiophenesulfonamide

2-Carbomethoxy-3-[N-(4-chloro-3-methylisoxazol-5-yl)-N-MOM]thiophenesulfonamide (3.0 g, 7.8 mmol) in a mixture of THF (30 mL) and 1N NaOH (30 mL) was stirred for 3 h at RT. The reaction mixture was diluted with water (20 mL) and extracted with ethyl acetate (5 mL). The water solution was acidified with 1N HCl then extracted with ethyl acetate. The organics were washed with water, brine, dried over MgSO$_4$ and concentrated to give 2-carboxy-3-[N-(4-chloro-3-methylisoxazol-5-yl)-N-MOM]]thiophenesulfonamide as an oil (quantitative yield).

H. 3-[N-MOM-N-(4-Chloro-3-methylisoxazol-5-yl) aminosulfonyl]thiophene-2-carbonyl chloride To a solution of 2-carboxy-3-[N-(4-chloro-3-methylisoxazol-5-yl)-N-MOM]thiophenesulfonamide (1.5 g, 4.1 mmol) in a mixture of THF (10 mL) and chloroform (5 mL) pyridine (1 drop) was added at 0° C. followed by addition of 2M solution of oxalyl chloride (4.5 mL, 9.0 mmol). The reaction mixture was stirred overnight at RT. To work up the reaction mixture was concentrated under reduced pressure to remove all volatiles. The desired product was obtained as a sticky oil which solidifies upon standing.

I. 3-[N-MOM-N-(4-Chloro-e-methylisoxazol-5-yl)aminosulfonyl]thiophene-2-carboxylic acid, 3-cyanomethyl-2,4,6-trimethylanilide To a solution of 3-cyanomethyl-2,4,6-trimethylaniline (1.2 g, 6.9 mmol) in THF (20 mL) under nitrogen was added a solution of 3-[N-MOM-N-(4-Chloro-3-methylisoxazol-5-yl)aminosulfonyl]thiophene-2-carbonyl chloride (1.3 mg, 3.3 mmol) in THF (10 mL) at 0° C. The reaction mixture was allowed to warm up to RT and stirred for 2 h. To work up the reaction mixture was poured into 0.05N HCl and the product was extracted with ethyl acetate. The organics were washed with 0.05N HCl, water, half-saturated NaHCO$_3$, water, brine, dried over MgSO$_4$, concentrated. Purification via column chromatography (silica, 40% ethyl acetate/hexane) gave 3-[N-MOM-N-(4-chloro-3-methylisoxazol-5-yl)aminosulfonyl]thiophene-2-carboxylic acid, 3-cyanomethyl-2,4,6-trimethylanilide as a clear oil (1.3 g, 76%).

J. N-(3-Cyanomethyl-2,4,6-trimethylphenyl)-3-(4-chloro-3-methyl-5-isoxazolylsulfamoyl)-2-thiophenecarboxamide, N(sulfonamide)-Na-salt A solution of 3-[N-MOM-N-(4-chloro-3-methylisoxazol-5-yl)aminosulfonyl]thiophene-2-carboxylic acid, 3-cyanomethyl-2,4,6-trimethylanilide (500 mg, 0.95 mmol) in THF (4 mL) and conc. HCl (2 mL) was stirred at 65–72° C. for 3.5 h. To work up the reaction mixture was cooled and poured into water (50 mL). The product was taken into ethyl acetate. The extract was washed with water, brine saturated NaHCO$_3$, brine, dried over MgSO$_4$, concentrated as an oil. The oil was recrystallized from ethyl acetate/hexane to give N-(3-cyanomethyl-2,4,6-trimethylphenyl)-3-(4-chloro-3-methyl-5-isoxazolylsulfamoyl)-2-thiophenecarboxamide as a white solid (410 mg, 91 %). The product (300 mg, 0.63 mmol) was dissolved in ethyl acetate (70 mL). The solution was washed with saturated NaHCO$_3$, brine, dried over MgSO$_4$, concentrated under reduced pressure. Methylene chloride (10 mL) was added with stirring followed by addition of ether. Na-salt of N-(3-cyanomethyl-2,4,6-trimethylphenyl)-3-(4-chloro-3-methyl-5-isoxazolylsulfamoyl)-2-thiophenecarboxamide was precipitated as a white solid which was isolated by filtration (292 mg, 92%). $^1$H NMR (DMSO-d$_6$)δ 1.99 (s, 3H); 2.13(s, 3H); 2.21 (s, 3H); 2.33 (s, 3H); 3.90 (s, 2H); 7.03 (s, 1H); 7.43 (d, 2H); 7.72 (d, 1H); 11.15 (s, 1H). IR (KBr) 3445, 2977, 2258, 1602, 1417, 1292, 1132, 1090 cm$^{-1}$. Elemental analysis found: C, 44.68; H, 3.92; N, 10.18 C$_{20}$H$_{18}$ClN$_4$NaO$_4$S$_2$.2.0H$_2$O requires: C, 44.73; H, 4.13; N, 10.43.

EXAMPLE 15

2-(3-Acetoxymethyl-2,4,6-trimethylphenyl)-3-(4-chloro-3-methyl-5-isoxazolylsulfamoyl)-2-thiophenecarboxamide, N(sulfonamide)-Na-salt A. 3-Nitro-2,4,6-trimethylbenzoic acid To a suspension of 2,4,6-trimethylbenzoic acid (4.6 g, 28 mmol) in 70% HNO$_3$ (85 mL) conc. H$_2$SO$_4$ (5 mL). was added dropwise at RT. The brown reaction mixture was stirred for 1 h, poured into ice-water (500 mL). The product was extracted into ethyl acetate, the extract was washed with water, dried over MgSO$_4$ and concentrated to give 3-nitro-2,4,6-trimethylbenzoic acid as a yellow solid (6.7 g, 94%).

B. 3-Nitro-2,4,6-trimethylbenzyl alcohol

To a solution of 3-nitro-2,4,6-trimethylbenzoic acid (6.7 g, 31.9 mmol) in anhydrous THF (100 mL) was added 1 m solution of BH3.THF in THF (63.8 mL, 63.8 mmol) dropwise at 0° C. The reaction mixture was stirred overnight at RT, cooled to 0° C. and quenched with water. The product was extracted into ethyl acetate, the extract was washed with water, dried over MgSO$_4$ and concentrated to give 1-acetoxymethyl-3-nitro-2,4,6-trimethylbenzene as a light yellow oil (6.3 g, 89%).

C. 3-Acetoxymethyl-2,4,6-trimethylaniline

To a solution of 1-acetoxymethyl-3-nitro-2,4,6-trimethybenzene (6.0 g, 25.2 mmol) in methanol (100 mL) were sequentially added ammonium chloride (2.7 g in 25 mL of water), zinc powder (11 g). The exothermic reaction was vigorously stirred until it was back to RT (2 h). To work up the crude mixture was filtered off and the cake was washed with methanol. The methanolic solutions were concentrated to a volume of 20 mL, added 1N HCl (300 mL). The insoluble material was removed by filtration, the solution was basified with solid NaHCO$_3$. The semicrystalline precipitate was taken into ethyl acetate. The extract was concentrated and the residual product purified by means of column chromatography (25% ethyl acetate/hexane) to give 3-Acetoxymethyl-2,4,6-trimethylaniline as a pink oil (3.8 g, 75%).

D. 3-[N-MOM-N-(4-Chloro-3-methylisoxazol-5-yl)aminosulfonyl]thiophene-2-carboxylic acid, 3-acetoxymethyl-2,4,6-trimethylanilide This compound was synthesized in the same fashion as for 3-[N-MOM-N-(4-chloro-3-methylisoxazol-5-yl)aminosulfonyl]thiophene-2-carboxylic acid, 3-cyanomethyl-2,4,6-trimethylanilide.

E. 2-(3-Acetoxymethyl-2,4,6-trimethylphenyl)-3-(4-chloro-3-methyl-5-isoxazolylsulfamoyl)-2-thiophenecarboxamide, N(sulfonamide)-Na-salt To a solution of 3-[N-MOM-N-(4-Chloro-5-methylisoxazol-3-yl)aminosulfonyl]thiophene-2-carboxylic acid, 3-acetoxymethylanilide (400 mg, 0.90 mmol) in acetic acid (4 mL) at 50° C. water (2 mL) and 2N $H_2SO_4$ (2 drops) were added afterwards the reaction mixture was stirred for 3.0 h at 75–80° C. To work up the reaction mixture was cooled and poured into water (20 mL). The product was taken into ethyl acetate. The extract was washed with water, brine, dried over $MgSO_4$, concentrated to an oil. Column chromatography (10% methanol/,methylene chloride) followed by trituration of the obtained oily material with ethyl acetate/hexane afforded 2-(3-acetoxymethyl-2,4,6-trimethylphenyl)-3-(4-chloro-3-methyl-5-isoxazolylsulfamoyl)-2-thiophenecarboxamide as a white powder (180 mg, 49%). The above-material (240 mg, 0.47 mmol) was dissolved in ethyl acetate (70 mL). The solution was washed with saturated $NaHCO_3$, brine, dried over $MgSO_4$, concentrated under reduced pressure. Methylene chloride (10 mL) was added with stirring followed by addition of ether. Na-salt of 2-(3-acetoxymethyl-2,4,6-trimethylphenyl)-3-(4-chloro-3-methyl-5-isoxazolylsulfamoyl)-2-thiophenecarboxamide was precipitated as a white solid which was isolated by filtration (209 mg, 83%). $^1$H NMR (DMSO-$d_6$);δ1.98 (s, 3H); 2.02 (s, 3H); 2.13 (s, 3H); 2.17 (s, 3H); 2.31 (s, 3H); 5.11 (s, 2H); 6.99 (s, 1H); 7.41 (d, 2H); 7.71 (d, 1H); 11.09 (s, 1H). IR (KBr) 3447, 2963, 1730, 1602, 1497, 1417, 1261, 1133, 1089 cm. Elemental analysis found: C, 44.94; H, 4.20; N, 7.12. $C_{21}H_{21}ClN_3NaO_6S_2.1.5H_2O$ requires: C, 44.96; H, 4.31; N, 7.44.

EXAMPLE 16

2-(3-Hydroxymethyl-2,4,6-trimethylphenyl)-3-(4-chloro-3-methyl-5-isoxazolylsulfamoyl)-2-thiophenecarboxamide A solution of 2-(3-acetoxymethyl-2,4,6-trimethylphenyl)-3-(4-chloro-3-methyl-5-isoxazolylsulfamoyl)-2-thiophenecarboxamide (Example 15) (250 mg, 0.49 mmol) in anh. MeOH (5 mL) was cooled to 0° C. and charged with 25% solution of sodium methoxide in MeOH (1.08 g, 5.0 mmol). Stirred for 30 min at 0° C. then the methanol was removed. Added 1N HCl (10 mL). The compound was taken into ethyl acetate. The extract was washed with water, brine, dried over $MgSO_4$, concentrated. The residue was dissolved in ethyl acetate then the product was precipitated by addition of hexane. This gave 2-(3-hydroxymethyl-2,4,6-trimethylphenyl)-3-(4-chloro-3-methyl-5-isoxazolylsulfamoyl)-2-thiophenecarboxamide as a white powder (205 mg, 90%). $^1$H NMR (DMSO-$d_6$)δ 1.99 (s, 3H); 2.11 (s, 3H); 2.22(s, 3H); 2.31 (s, 3H); 4.47 (s, 2H); 6.91 (s, 1H); 7.41 (d, 2H); 7.73 (d, 1H); 10.83 (s, 1H). IR (KBr) 3424, 2963, 1637, 1527, 1492, 1411, 1267, 1186, 1151, 1109 cm$^{-1}$. Elemental analysis found: C, 48.50; H, 4.10; N, 8.63. $C_{19}H_{20}ClN_3O_5S_2$ requires: C, 48.56; H, 4.29; N, 8.94.

EXAMPLE 17

3-(4-Chloro-5-methylisoxazolyl-3-aminosulfonyl) thiophene-2-carboxylic acid, N-(3-cyanomethyl-2,4, 6-trimethyl)anilide, Na-salt A. 3-Cyanomethyl-2,4,6-trimethylaniline
 3-Cyanomethyl-2,4,6-trimethylaniline was synthesized and purified as in Example 14.

B. 3-Amino-4-chloro-5-methylisoxazole
 To a solution of 3-amino-5-methylisoxazole (9.8 g, 100 mmol) in methylene chloride (200 mL) was added N-chlorosuccinimide (14.6 g, 110 mmol) at 0° C. over the period of 20 min. The reaction mixture was stirred overnight. To work up the reaction mixture was concentrated and partitioned between 1N NaOH (150 mL) ethyl acetate (400 mL). The organic layer was washed with 1N NaOH, water, brine, dried over $MgSO_4$ then concentrated to a brown solid. For purification the product was reprecipitated from chloroform/hexane to give 3-amino-4-chloro-5-methylisoxazole as a brownish solid (9.5 g, 71%).

C. 2-Carbomethoxy-3-[N-(4-chloro-5-methylisoxazol-3-yl)]thiophenesulfonamide
 To a solution of 3-amino-4-chloro-5-methylisoxazole (6.1 g, 45.4 mmol) in anhydrous pyridine (7 mL) under nitrogen was added 2-carbomethoxy-3-thiophenesulfonyl chloride (14.2 g, 59.0 mmol) at 0° C. The reaction mixture was allowed to warm up to RT and stirred for 2 h. To work up the reaction mixture was poured into 1N HCl and the product was extracted with ethyl acetate. The combined organics were washed with 1N HCl, water then the compound was extracted with half-saturated $NaHCO_3$. The combined basic solutions were cooled to 0° C. and acidified with 4N HCl. The product was isolated by filtration, washed with water, dried to give 2-carbomethoxy-3-[N-(4-chloro-5-methylisoxazol-3-yl)]thiophenesulfonamide as a white powder (5.3 g, 34%).

D. 3-[N-MOM-N-(4-Chloro-5-methylisoxazol-3-yl) aminosulfonyl]thiophene-2-carbonyl chloride
 3-[N-MOM-N-(4-Chloro-5-methylisoxazol-3-yl) aminosulfonyl]thiophene-2-carbonyl chloride was synthesized in the same fashion as for 3-[N-MOM-N-(4-Chloro-3-methylisoxazol-5-yl)aminosulfonyl]thiophene-2-carbonyl chloride (see EXAMPLE 14).

E. 3-[N-MOM-N-(4-Chloro-5-methylisoxazol-3-yl) aminosulfonyl]thiophene-2-carboxylic acid, 3-cyanomethyl-2,4,6-trimethylanilide
 3-[N-MOM-N-(4-Chloro-5-methylisoxazol-3-yl) aminosulfonyl]thiophene-2-carboxylic acid, 3-cyanomethyl-2,4,6-trimethylanilide was synthesized in the same fashion as for 3-[N-MOM-N-(4-Chloro-3-methylisoxazol-5-yl)aminosulfonyl]thiophene-2-carboxylic acid, 3-cyanomethyl-2,4,6-trimethylanilide (see EXAMPLE 14).

EXAMPLE 18

3-(4-Chloro-5-methylisoxazolyl-3-aminosulfonyl) thiophene-2-carboxylic acid, N-(3-acetoxymethyl-2, 4,6-trimethyl)anilide 3-(4-Chloro-5-methylisoxazolyl-3-aminosulfonyl) thiophene-2-carboxylic acid, N-(3-acetoxymethyl-2,4,6-trimethyl)anilide as a free acid was synthesized in the same fashion as in Example 15. $^1$H NMR (DMSO-$d_6$δ2.02 (3, 3H); 2.17 (m, 9H); 2.33 (s, 3H); 5.12 (s, 2H); 6.97 (s, 1H); 7.35 (d, 2H); 7.62 (d, 1H); 11.38 (s, 1H). IR (KBr) 3444, 2963, 1734, 1634, 1544, 1485, 1412, 1256, 1159, 1122 cm$^{-1}$. Elemental analysis found: C, 45.03; H, 4.27; N, 7.16. $C_{21}H_{22}ClN_3O_6S_2.1.5H_2O$ requires: C, 44.96; H, 4.31; N, 7.44.

EXAMPLE 19

3-(4-Chloro-5-methylisoxazolyl-3-aminosulfonyl) thiophene-2-carboxylic acid, N-(3-hydroxymethyl-2, 4,6-trimethyl)anilide 3-(4-Chloro-5-methylisoxazolyl-3-aminosulfonyl) thiophene-2-carboxylic acid, N-(3-hydroxymethyl-2,4,6-trimethyl)anilide as a free acid was synthesized in the same fashion as in Example 16. $^1$H NMR (DMSO-$d_6$δ2.15(s, 3H); 2.24 (s, 3H); 2.33 (m, 6H); 4.48 (s, 2H); 6.92 (s, 1H); 7.43

(d, 2H); 7.80 (d, 1H). IR(KBr) 3443, 2963, 1641, 1522, 1490, 1184 cm$^{-1}$. Elemental analysis found: C, 47.69; H, 4.24; N, 8.63. $C_{19}H_{20}ClN_3O_5S_2 \cdot 0.5H_2O$ requires: C, 47.65; H, 4.42; N, 8.77.

EXAMPLE 20

3-[N-(Benzo-2,1,3-tiadiazol-5yl-; aminosulfonyl] thiophene-2-carboxylic acid, 3-cyanomethyl-2,4,6-trimethylanilide A. 3-Cyanomethyl-2,4,6-trimethylaniline 3-Cyanomethyl-2,4,6-trimethylaniline was synthesized and purified as in EXAMPLE 14.

B. 5-Aminobenzo-2,1,3-thiadiazole

To a solution of 5-nitrobenzo-2,1,3-thiadiazole in a mixture of dioxane (22 mL) and ethanol (22 mL) at RT added solid $SnCl_2$ followed by addition of water (1 mL). The reaction mixture was warmed up to 50° C. and stirred for 10 min, cooled to RT, concentrated and partitioned between ethyl acetate/1N NaOH. The organic layer was washed with 1N NaOH, water, brine, dried over $MgSO_4$ and charcoal. Evaporation of the solvent gave 5-aminobenzo-2,1,3-thiadiazole as a yellow powder (3.0 g, 88%).

C. 2-Carbomethoxy-3-[N-(benzo-2,1,3-thiadiazol-5-yl)] thiophenesulfonamide

2-Carboxmethoxy-3[N-(benzo-2,1,3-thiadiazol-5-yl)] thiophenesulfonamide was synthesized in the same fashion as for 2-carbomethoxy-3-[N-(4-chloro-5-methylisoxazol-3-yl)]thiophenesulfonamide (Example 17).

D. 3-[N-MOM-N-(Benzo-2,1,3-thiadiazol-5-yl) aminosulfonyl]-2-thiophenecarbonyl chloride 3-[N-MOM-N-(Benzo-2,1,3-thiadiazol-5-yl) aminosulfonyl]-2-thiophenecarbonyl chloride was synthesized in the same fashion as for 3-[N-MOM-N-(4-chloro-5-methylisoxazol-3-yl)aminosulfonyl]-thiophene-2-carbonyl chloride (Example 14).

E. 3-[N-(Benzo-2,1,3-thiadiazol-5-yl)aminosulfonyl] thiophene-2-carboxylic acid, 3-cyanomethyl-2,4,6-trimethylanilide To a solution of 3-cyanomethyl-2,4,6-trimethylaniline (400 mg, 2.27 mmol) in THF (3 mL) at 0° C. a solution of 3-[N-MOM-N-(benzo-2,1,3-thiadiazol-5-yl) aminosulfonyl]-2-thiophenecarbonyl chloride (442 mg, 1.08 mmol) in THF (5 mL) was added. The reaction mixture stirred for 2 h at RT. The reaction mixture was poured into 1N HCl and extracted with ethyl acetate. The extract was washed with 1N HCl, water, brine, dried over $MgSO_4$, concentrated. Column chromatography (25% ethyl acetate/hexane on Silica Gel) followed by recrystallization of the obtained material from ethyl acetate/hexane gave 3-[N-(benzo-2,1,3-thiadiazol-5-yl)aminosulfonyl]thiophene-2-carboxylic acid, 3-cyanomethyl-2,4,6-trimethylanilide as a white solid (19 mg, 3.5%). $^1$H NMR (DMSO-$d_6$ $\delta$2.21 (s, 3H); 2.26 (s, 3H); 2.34 (s, 3H); 3.93 (s, 2H); 7.06 (s, 1H); 7.48 (d, 1H); 7.55 (m, 1H); 7.72 (m, 1H); 7.82 (d, 1H); 7.99 (m, 1H); 10.18 (s, 1H); 10.80 (s, 1H). IR(KBr) 3447, 3240, 2974, 1651, 1529, 1458, 1271, 1187, 1145 cm$^{-1}$.

EXAMPLE 21

$N^2$-(3-Cyanomethyl-2,4,6-trimethylphenyl)-3-[(3,4-dimethyl-5-isoxazolyl)sulfamoyl]-2-thiophenecarboxamide, Na-salt A. 5-[N-(2-Carbomethoxythienyl-3-sulfonyl)amino]-3,4-dimethylisoxazole To a solution of 5-amino-3,4-dimethylisoxazole (2.0 g, 17.83 mmol) in dichloromethane (60 mL) were added triethylamine (5.5 mL, 39.24 mmol) and 4-dimethylaminopyridine (0.2 g, 0.89 mmol), then cooled to 0° C. 2-(Methoxycarbonyl)thiophenesulfonyl chloride (9.44 g, 39.22 mmol) was added. The resulting mixture was stirred at room temperature overnight, then mixed with water (60 mL). The organic material was separated, and the aqueous layer was extracted with dichloromethane (2×30 mL). The extracts were combined and washed with water (60 mL) and saturated sodium chloride (60 mL), dried ($MgSO_4$), then concentrated to give 5-[N,N-bis(2-carbomethoxythienyl-3-sulfonyl)amino]-3,4-dimethylisoxazole (10.02 g, >100%) as a brown oil. This crude product (10.02 g, 19.25 mmol) was dissolved in anhydrous methanol (64 mL). Potassium hydroxide (1.1 g, 19.25 mmol) was added at 0° C., and stirred at 0° C. for 15 minutes. The mixture was acidified to pH 2 with concentrated hydrochloric acid, extracted with ethyl acetate (3×100 mL), washed with water (250 mL) and saturated sodium chloride (250 mL), dried ($MgSO_4$), then concentrated. The residue was purified by flash chromatography ($SiO_2$, hexane: ethyl acetate/3:1) to give 5-[N-(2-carbomethoxythienyl-3-sulfonyl)amino]-3,4-dimethylisoxazole (5.43 g, 84%) as a yellow oil.

B. 5-[N-Methoxymethyl-(2-carbomethoxythienyl-3-sulfonyl)amino]-3,4-dimethylisoxazole To a solution of 5-[N-(2-carbomethoxythienyl-3-sulfonyl) amino]-3,4-dimethylisoxazole (5.43 g, 17.16 mmol) in dichloromethane (50 mL) at 0° C. was added N,N-diisopropylethylamine (9.0 mL, 51.49 mmol) followed by bromomethyl methyl ether (1.5 mL, 18.88 mmol). The resulting mixture was stirred at room temperature for 15 minutes, then quenched with saturated sodium bicarbonate. The organic material was separated, and the aqueous layer was extracted with dichloromethane (2×25 mL). The extracts were combined and washed with water (50 mL) and saturated sodium chloride (50 mL), dried ($MgSO_4$), then concentrated. The residue was purified by flash chromatography ($SiO_2$, hexane:ethylacetate/6:1, then 3:1) to give 5-[N-methoxymethyl-(2-carbomethoxythienyl-3-sulfonyl)amino]-3,4-dimethylisoxazole (5.71 g, 92%) as a yellow oil.

C. 5-[N-Methoxymethyl-(2-carboxythienyl-3-sulfonyl)amino]-3,4-dimethylisoxazole

To a solution of 5-[N-methoxymethyl-(2-carbomethoxythienyl-3-sulfonyl)amino]-3,4-dimethylisoxazole (5.71 g, 15.84 mmol) in THF (30 mL) was added a solution of sodium hydroxide (0.95 g, 23.77 mmol) in water (15 mL). The mixture was stirred at room temperature overnight. The reaction was acidified to pH 3 with 2N hydrochloric acid while cooling at 0° C., then extracted with ethyl acetate (3×50 mL). The organic layer was washed with saturated sodium chloride (100 mL), dried ($MgSO_4$), and concentrated to give 5-[N-methoxymethyl-(2-carboxythienyl-3-sulfonyl)amino]-3,4-dimethylisoxazole (3.50 g, 64%) as a yellow solid.

D. 3-[N-3,4-Dimethylisoxazol-5-yl)-N-methoxymethylaminosulfonyl]-2-thiophenecarbonyl chloride To a solution of 5-[N-methoxymethyl-(2-cargoxythienyl-3-sulfonyl)amino]-3,4-dimethylisoxazole (3.49 g, 10.08 mmol) in dichloromethane (20 mL) at 0° C. was added pyridine (3 drops) followed by oxalyl chloride (11 mL, 22.17 mmol). The mixture was stirred at room temperature overnight, then concentrated to dryness to give 3-[N-(3,4-dimethylisoxazol-5-yl)-N-methoxymethylaminosulfonyl]-2-thiophenecarbonyl chloride (4.01 g, >100%) as a yellow oil.

E. $N^2$-(3-Cyanomethyl-2,4,6-trimethylphenyl)-3-[N-(3,4-dimethylisoxazol-5-yl)-N-methoxymethylaminosulfonyl]-2-thiophenecarboxamide To a solution of 3-[N-(3,4-dimethylisoxazol-5-yl)-N-methoxymethylaminosulfonyl]-2-thiophenecarbonyl chloride (0.49 g, 1.34 mmol) in dichloromethane (4 mL) was added 3-cyanomethyl-2,4,6-trimethylaniline (0.24 g, 1.34 mmol) at 0° C. Triethylamine (0.21 mL, 1.47 mmol) and 4-dimethylaminopyridine (16 mg, 0.13 mmol) were added. The mixture was stirred at room temperature for 2 hours, then mixed with water (10 mL). The organic material was separated, and the aqueous layer was extracted with dichloromethane (2×5 mL). The extracts were combined and washed with water (10 mL) and saturated sodium chloride (10 mL), dried (MgSO$_4$), then concentrated. The residue was purified by flash chromatography (SiO$_2$, hexane:ethyl acetate/3:1, then 1:1) to give $N^2$-(3-cyanomethyl-2,4,6-trimethylphenyl)-3-[N-(3,4-dimethylisoxazol-5-yl)-N-methoxymethylaminosulfonyl]-2-thiophenecarboxamide (0.28 g, 41%) as a yellow oil.

F. $N^2$-(3-Cyanomethyl-2,4,6-trimethylphenyl)-3-[(3,4-dimethyl-5-isoxazolyl)sulfamoyl]-2-thiophenecarboxamide, Na-salt To a solution of $N^2$-(3-cyanomethyl-2,4,6-trimethylphenyl)-3-[N-(3,4-dimethylisoxazol-5-yl)-N-methoxymethylaminosulfonyl]-2-thiophenecarboxamide (2.29 g, 4.56 mmol) in THF (10 mL) was added concentrated hydrochloric acid (5 mL). The reaction was heated at 65° C. for 2 hours, then allowed to cool to room temperature. The mixture was poured into ice water (100 mL), extracted with ethyl acetate (3×100 mL), washed with saturated sodium chloride (150 mL), dried (MgSO$_4$), then concentrated. The residue was purified by reverse-phase HPLC (20–80% acetonitrile in water). Acetonitrile was removed in vacuo. The aqueous layer was extracted with ethyl acetate (3×100 mL). The extracts were combined and washed with saturated sodium chloride (200 mL), then with saturated sodium bicarbonate (3×200 mL). The organic layer was washed with saturated sodium chloride (200 mL), dried (MgSO$_4$), then concentrated. The residue was purified by reverse-phase HPLC (20–80% acetonitrile in water). Acetonitrile was removed in vacuo. The aqueous layer was extracted with ethyl acetate (3×100 mL). The extracts were combined and washed with saturated sodium chloride (200 mL), then with saturated sodium bicarbonate (3×200 mL). The organic layer was washed with saturated sodium chloride (200 mL), dried (MgSO$_4$), then concentrated. The residue was dissolved in water (300 mL) and lyophilized to give $N^2$-(3-cyanomethyl-2,4,6-trimethylphenyl)-3-[(3,4-dimethyl-5-isoxazolyl)sulfamoyl]-2-thiophenecarboxamide, Na-salt (0.45 g, 21%) as a white powder, mp 153–173° C. $^1$H NMR (400 MHZ, DMSO-d$_6$δ7.69 (d, J=4.76 Hz, 1H), 7.35 (d, J=5.16 Hz, 1H), 7.02 (s, 1H), 3.90 (s, 2H), 2.32 (s, 3H), 2.20 (s, 3H), 2.13 (s, 3H), 1.95 (s, 3H), 1.55 (s, 3H) IR (KBr) 3449, 2249, 1623, 1421, 1121 cm$^{-1}$.

EXAMPLE 22

$N^2$-(3-Acetoxymethyl-2,4,6-trimethylphenyl)-3-[(3,4-dimethyl-5-isoxazolyl)sulfamoyl]-2-thiophenecarboxamide and $N^2$-(3-Hydroxymethyl-2,4,6-trimethylphenyl)-3-[(3,4-dimethyl-5-isoxazolyl)sulfamoyl]-2-thiophenecarboxamide A. $N^2$-(3-Acetoxymethyl-2,4,6-trimethylphenyl)-3-[N-(3,4-dimethylisoxazol-5-yl)-N-methoxymethylaminosulfonyl]-2-thiophenecarboxamide To a solution of 3-[N-(3,4-dimethylisoxazol-5-yl)-N-methoxymethylaminosulfonyl]-2-thiophenecarbonyl chloride (1.1 g, 2.97 mmol) in dichloromethane (9 mL) was added 3-acetoxymethyl-2,4,6-trimethylaniline (0.6 g, 2.97 mmol) at 0° C. Triethylamine (0.46 mL, 3.26 mmol) and 4-dimethylaminopyridine (36 mg, 0.30 mmol) were added. The mixture was stirred at room temperature overnight, then mixed with water (10 mL). The organic material was separated, and the aqueous layer was extracted with dichloromethane (2×10 mL). The extracts were combined and washed with water (20 mL) and saturated sodium chloride (20 mL), dried (MgSO$_4$), then concentrated. The residue was purified by flash chromatography (SiO$_2$, hexane:ethyl acetate/2:1) to give $N^2$-(3-acetoxymethyl-2,4,6-trimethylphenyl)-3-[N-(3,4-dimethylisoxazol-5-yl)-N-methoxymethylaminosulfonyl]-2-thiophenecarboxamide (0.79 g, 50%) as a yellow oil.

B. $N^2$-(3-Acetoxymethyl-2,4,6-trimethylphenyl)-3-[(3,4-dimethyl-5-isoxazolyl)sulfamoyl]-2-thiophenecarboxamide and $N^2$-(3-Hydroxymethyl-2,4,6-trimethylphenyl)-3-[(3,4-dimethyl-5-isoxazolyl)sulfamoyl]-2-thiophenecarboxamide To a solution of $N^2$-(3-acetoxymethyl-2,4,6-trimethylphenyl)-3-[N-(3,4-dimethylisoxazol-5-yl)-N-methoxymethylaminosulfonyl]-2-thiophenecarboxamide (0.78 g, 1.46 mmol) in acetic acid (7 mL) and water (3 mL) was added 2N sulfuric acid (3 drops). The reaction was heated at 80° C. for 4 hours, then allowed to cool to room temperature. The mixture was poured into ice water (50 mL), extracted with ethyl acetate (3×50 mL), washed with saturated sodium chloride (50 mL), dried (MgSO$_4$), then concentrated. The residue was purified by reverse-phase HPLC (20–80% acetonitrile in water) which gave $N^2$-(3-acetoxymethyl-2,4,6-trimethylphenyl)-3-[(3,4-dimethyl-5-isoxazolyl)sulfamoyl]-2-thiophenecarboxamide (0.2 g, 28%) as an off-white powder, mp 75–77° C. $^1$H NMR (400 MHZ, DMSO-d$_6$δ7.84 (d, J=5.12 Hz, 1H), 7.34 (d, J=5.12 Hz, 1H), 7.00 (s, 1H), 5.12 (s, 2H), 2.30 (s, 3H), 2.20 (s, 3H), 2.17 (s, 3H), 2.07 (s, 3H), 2.02 (s, 3H), 1.65 (s, 3H) IR (KBr) 3458, 1738, 1646, 1356, 1181 cm$^{-1}$. And $N^2$-(3-hydroxymethyl-2,4,6-trimethylphenyl)-3-[(3,4-dimethyl-5-isoxazolyl)sulfamoyl]-2-thiophenecarboxamide (45 mg, 6.9%), ratio 4:1 respectively, as a white powder, mp 100–115° C. $^1$H NMR (400 MHZ, DMSO-d$_6$δ7.84 (3, J=5.12 Hz, 1H), 7.34 (d, J=5.16 Hz, 1H), 6.92 (s, 1H), 4.48 (s, 2H), 2.33 (s, 3H), 2.23 (s, 3H), 2.14 (s, 3H), 2.07 (s, 3H), 1.65 (s, 3H) IR (KBr) 3439, 1651, 1341, 1181 cm$^{-1}$.

EXAMPLE 23

Formulations of Sulfonamide Sodium Salts

A. Formulation of Sulfonamide Sodium Salts for Intravenous Administration

Phosphate buffer is prepared by adding 3200 mL of sterile water for injection, USP, to a 4 L graduated cylinder. Sodium phosphate dibasic heptahydrate, USP (21.44 g) is added to the sterile water and the mixture is stirred for 5 minutes or until the solid had dissolved. Sodium phosphate monobasic, USP (11.04 g) is added and the mixture was stirred until the solids had dissolved. The solution was diluted to 4.0 L and stirred. 3000 g of the sodium phosphate buffer is added to an eight liter beaker. Dextrose, USP (200.0 g) is added, and the mixture is heated to 30–35° C. in a water bath and stirred until a complete solution formed. A sulfonamide sodium salt (100.0 g) is added with efficient mixing. This mixture is stirred for a minimum of ten minutes or until a solution formed. The solution was removed from the water bath after the sodium salt dissolved. The solution was diluted to 4000 g with sodium phosphate buffer and stirred for five minutes. This solution is sterile filtered using a sterile 0.22 micron pre-size Durapore Millipak 200 filter. The filtered solution is filled into sterile vials and lyophilized under standard conditions. The vials are stoppered. The lyophilized product was then reconstituted with either 9.4 mL or 19.4 mL of water for injection, to give a final concentration of 25 mg/mL or 12.5 mg/mL, respectively.

B. Formulation of Sulfonamide Sodium Salts for Oral Administration

These formulations may be prepared by methods known to those of skill in the art (see, e.g., Ansel *Introduction to Pharmaceutical Dosage Forms* (4th Edition) 1985 (Lea & Febiger)). In general, the tablets may be prepared by wet or dry granulation of the ingredients, followed by compression. Alternatively, the combined ingredients may be formed into tablets by direct compression. In the preparation of capsules, the combined sulfonamide sodium salt, excipient (diluent), binder, disintegrating agent and lubricant are filled directly into the capsule shell. The optimal amount of active and inert ingredients in these formulations may be determined empirically by methods known to those of skill in the art. In general, the amount of active ingredient (i.e., sulfonamide sodium salt) will be sufficient to provide a therapeutically-effective dose of the active ingredient. The therapeutically effective dose may be determined empirically by testing the compounds in known in vitro and in vivo systems (see, e.g., U.S. Pat. No. 5,114,918 to Ishikawa et al.; EP A1 0 436 189 to BANYU PHARMACEUTICAL CO., LTD (Oct. 7, 1991); Borges et al. (1989) *Eur. J. Pharm.* 165: 223–230;: Filep et al. (1991) *Biochem. Biophys. Res. Commun.* 177: 171–176) and then extrapolated therefrom for dosages for humans.

EXAMPLE 24
Assays for Identifying Compounds that Exhibit Endothelin Antagonistic and/or Agonist Activity Compounds that are potential endothelin antagonists are identified by testing their ability to compete with $^{125}$I-labeled ET-1 for binding to human $ET_A$ receptors or $ET_B$ receptors present on isolated cell membranes. The effectiveness of the test compound as an antagonist or agonist of the biological tissue response of endothelin can also be assessed by measuring the effect on endothelin induced contraction of isolated rat thoracic aortic rings. The ability of the compounds to act as antagonists or agonists for $ET_B$ receptors can be assess by testing the ability of the compounds are to inhibit endothelin-1 induced prostacyclin release from cultured bovine aortic endothelial cells.

A. Endothelin Binding Inhibition—Binding Test #1: Inhibition of Binding to $ET_A$ Receptors TE 671 cells (ATCC Accession No. HTB 139) express $ET_A$ receptors. These cells were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. at 57,800×g for 15 min, the pellet was resuspended in 5 mL of buffer A (5 mM HEPES buffer, pH 7.4 containing aprotinin (100 KIU/ml)) and then frozen and thawed once. 5 mL of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/mL) to give a final protein concentration of 2 mg/mL and stored at −70° C. until use.

The membrane suspension was diluted with binding buffer (30 mM HEPES buffer, pH 7.4 containing 150 mM NaCl, 5 mM $MgCl_2$, 0.5% Bacitracin) to a concentration of 8 µg/50 µL. $^{125}$I-endothelin-1 (3,000 cpm, 50 mL) was added to 50 µL of either: (A) endothelin-1 (for non specific binding) to give a final concentration 80 nM); (B) binding buffer (for total binding); or (C) a test compound (final concentration 1 nM to 100 µM). The membrane suspension (50 µL), containing up to 8 µg of membrane protein, was added to each of (A), (B), or (C). Mixtures were shaken, and incubated at 4° C. for 16–18 hours, and then centrifuged at 4° C. for 25 min at 2,500×g. Alternatively, the incubation was conducted at 24° C. When incubated at 24° C., the $IC_{50}$ concentrations are 2- to 10-fold higher than when the incubation is conducted at 4° C. This, must be kept in mind when comparing $IC_{50}$ concentrations among compounds provided herein.

The supernatant, containing unbound radioactivity, was decanted and the pellet counted on a Genesys multiwell gamma counter. The degree of inhibition of binding (D) was calculated according to the following equation:

$$\% D = 100 - \frac{(C) - (A)}{(B) - (A)} \times 100$$

Each test was generally performed in triplicate.

B. Endothelin Binding Inhibition—Binding Test #2: Inhibition of Binding to $ET_B$ Receptors COS7 cells were transfected with DNA encoding the $ET_B$ receptor, The resulting cells, which express the human $ET_B$ receptor, were grown to confluence in T-150 flasks. Membrane was prepared as described above. The binding assay was performed as described above using the membrane preparation diluted with binding buffer to a concentration of 1 µg/50 µL.

Briefly, the COS7 cells, described above, that had been transfected with DNA encoding the $ET_B$ receptor and express the human $ET_B$ receptor on their surfaces were grown to confluence in T-175 flasks. Cells from multiple flasks were collected by scraping, pooled and centrifuged for 10 min at 190×g. The cells were resuspended in phosphate buffered saline (PBS) containing 10 mM EDTA using a Tenbroeck homogenizer. The suspension was centrifuged at 4° C. 57,800×g for 15 min, the pellet was resuspended in 5 mL of buffer A (5 mM HEPES buffer, pH 7.4 containing aprotinin (100 KIU/mL)) and then frozen and thawed once. Five mL of Buffer B (5 mM HEPES Buffer, pH 7.4 containing 10 mM $MnCl_2$ and 0.001% deoxyribonuclease Type 1) was added, the suspension mixed by inversion and then incubated at 37° C. for 30 minutes. The mixture was centrifuged at 57,800×g as described above, the pellet washed twice with buffer A and then resuspended in buffer C (30 mM HEPES buffer, pH 7.4 containing aprotinin (100 KIU/mL) to give a final protein concentration of 2 mg/ml.

The binding assay was performed as described above using the membrane preparation diluted to give 1 µg/50 µL of binding buffer.

C. Test for Activity Against Endothelin-induced Contraction of Isolated Rat Thoracic Aortic Rings The effectiveness of the test compound as an antagonist or agonist of the biological tissue response of endothelin also is assessed by measuring the effect on endothelin induced contraction of isolated rat thoracic aortic rings (see, e.g., Borges et al. (1989) *Eur. J. Pharmacol.* 165:223–230) or by measuring the ability to contract the tissue when added alone.

Compounds to be tested are prepared as 100 µM stocks. If necessary to effect dissolution, the compounds are first dissolved in a minimum amount of DMSO and diluted with 150 mM NaCl. Because DMSO can cause relaxation of the aortic ring, control solutions containing varying concentrations of DMSO were tested.

The thoracic portion of the adult rat aorta is excised, the endothelium abraded by gentle rubbing and then cut into 3 mm ring segments. Segments are suspended under a 2 g preload in a 10 mL organ bath filled with Krebs'-Henseleit solution saturated with a gas mixture of 95% $O_2$ and 5% $CO_2$ (118 mM NaCl, 4.7 mM KCl, 1.2 mM $MgSO_4$, 1.2 mM $KH_2PO_4$, 25 mM $NaHCO_3$, 2.5 mM $CaCl_2$, 10 mM D-glucose).

There is a correlation between activity as an antagonist of endothelin-induced thoracic aortic ring contraction and activity as an inhibitor of binding of endothelin to endothelin receptors. The $pA_2$ is a linear function of the log of the $IC_{50}$.

D. Assay for Identifying Compounds that have Agonist and/or Antagonistic Activity Against $ET_B$ Receptors 1. Stimulation of Prostacyclin Release Since endothelin-1 stimulates the release of prostacyclin from cultured bovine aortic endothelial cells, the compounds that have agonist or antagonist activity are identified by their ability to inhibit endothelin-1 induced prostacyclin release from such endothelial cells by measuring 6-keto $PGF_{1\alpha}$ substantially as described by (Filep et al. (1991) *Biochem. Biophys. Res. Commun.* 177 171–176. Bovine aortic cells are obtained from collagenase-treated bovine aorta, seeded into culture plates, grown in Medium 199 supplemented with heat inactivated 15% fetal calf serum, and L-glutamine (2 mM), penicillin, streptomycin and fungizone, and subcultured at least four times. The cells are then seeded in six-well plates in the same medium. Eight hours before the assay, after the cells reach confluence, the medium is replaced. The cells are then incubated with a) medium alone, b) medium containing endothelin-1 (10 nM), c) test compound alone, and d) test compound+endothelin-1 (10 nM).

After a 15 min incubation, the medium is removed from each well and the concentrations of 6-keto $PGF_{1\alpha}$ are measured by a direct immunoassay. Prostacyclin production is calculated as the difference between the amount of 6-keto $PGF_{1\alpha}$ released by the cells challenged with the endothelin-1 minus the amount released by identically treated unchallenged cells. Compounds that stimulate 6-keto $PGF_{1\alpha}$ release possess agonist activity and those which inhibit endothelin-1 6-keto $PGF_{1\alpha}$ release possess antagonist activity.

2. Inhibition of Sarafotoxin 6c Induced Contraction

Sarafotoxin 6c is a specific $ET_B$ antagonist that contracts rat fundal stomach strips. The effectiveness of tests compounds to inhibit this sarafotoxin 6c-induced contraction of rat fundal stomach strips is used as a measure $ET_B$ antagonist activity. Two isolated rat fundal stomach strips are suspended under a 1 g load in a 10 mL organ bath filled with Krebs'-Henseleit solution containing 10 μM cyclo(D-Asp-Pro-D-Val-Leu-D-Trp) (BQ-123; see, U.S. Pat. No. 5,114,918 to Ishikawa et al.), 5 μM indomethacin, and saturated with a gas mixture of 95% $O_2$/5% $CO_2$. Changes in tension are measured isometrically and recorded using a Grass Polygraph coupled to a force transducer. Sarafotoxin 6c is added cumulatively to one strip while the second strip is preincubated for 15 min with a test compound prior to addition of cumulative doses of sarafotoxin 6c. The effects of the test compounds on the concentration-response curve for sarafotoxin 6c are examined.

E. Deoxycorticosterone Acetate (DOCA)-salt Hypertensive Rat Model for Assessing In Vivo Activity of Selected Compounds Selected compounds disclosed herein have been tested for activity in the deoxycorticosterone acetate (DOCA)-salt hypertensive rat model. To perform these tests, silastic MDX4-4210 elastomer implants containing 47 mg (DOCA) were prepared according to the method of Ornmsbee et al. ((1973) the *J. Pharm. Sci.* 62:255–257). Briefly, DOCA is incorporated into silicon rubber implants for sustained release. To prepare the implants the DOCA is incorporated into unpolymerized silicone rubber, catalyst is added and the mixture is cast in a hemicylindrical shape.

Sprague Dawley rats (7–8 weeks old) were unilaterally nephrectomized under ketamine anesthesia and a DOCA-implant was placed on the left lateral dorsal abdomen of the animal. The rats were allowed to recover for three weeks. During recovery they were permitted free access to normal rat chow and 0.9% NaCl drinking solution in place of drinking water. The rats develop hypertension within 3 weeks.

All animals were used in the tests between 21 and 30 days post surgery. The mean arterial blood pressure in these animals ranged from 165–200 mm Hg.

On the day of experimentation, catheters were inserted under brevital anesthesia into the right femoral artery for measurement of blood pressure, and into the right femoral vein for administration of a selected compound. The animals were placed in a restrainer and allowed to recover for a minimum of 60 min or until a steady mean arterial blood pressure was recorded. At that time, the selected compound or control vehicle was administered either intravenously, as a 60 minute infusion, or orally by oral gavage. Blood pressure was recorded continuously for a further 10 hrs.

F. Effect of Intravenous Administration on ET-1-induced Pressor Responses in Conscious, Autonomically Blocked Rats; A Model for Assessing In Vivo Activity of Selected Compounds Male Sprague Dawley rats (250–450 g) were anesthetized (Brevital 50 mg/kg, IP) and cannulae were placed in the femoral artery to measure mean arterial pressure (MAP) and in the femoral vein for intravenous drug administration. Animals were placed in a restrainer and allowed to regain consciousness. Thirty minutes later autonomic blockade was administered (atropine methyl nitrate, 3 mg/kg, IV, followed by propranalol, 2 mg/kg, IV). An hour later animals received a bolus injection of vehicle (0.5 mL) followed thirty minutes later by intravenous bolus administration of ET-1 (Control, 1 μg/kg). Following recovery from this challenge, test-compounds were administered by intravenous bolus administration (0.5 mL) and then re-challenged with ET-1 thirty minutes later. Results are expressed as the percent inhibition of the ET-1-induced pressor response after administration of the test compound compared to the pressor response induced by the control ET-1 challenge. In some cases a third ET-1 challenge was administered ninety minutes after administration of the test compound.

G. Results

1. In Vitro

The $IC_{50}$ for each of the compounds of the preceding Examples for $ET_A$ and $ET_B$ receptors has been measured. Almost all of the compounds have an $IC_{50}$ of less than 10 μM for either or both of the $ET_A$ and $ET_B$ receptors. Many of the compounds have an $IC_{50}$ less than about 10 μM, others have an $IC_{50}$ less than about 1 μM and some of the compounds have an $IC_{50}$ less than about 0.1 μM. A number of the compounds have an $IC_{50}$ for $ET_A$ receptors that is substantially less (10 to 100-fold or more) than for $ET_B$ receptors, and, thus are selective for $ET_A$ receptors. Others of the compounds are $ET_B$ selective.

2. In Vivo

Selected compounds, such as N-(4-chloro-3-methyl-5-isoxazolyl)-2-(3-hydroxy-2,4,6-trimethylphenylaminocarbonyl)thiophene-3-sulfonamide, have been tested in the hypertensive rat model, and were effective in decreasing blood pressure.

Since modifications will be apparent to those of skill in this art, it is intended that this invention be limited only by the scope of the appended claims.

What is claimed is:

1. A sulfonamide compound of formula (A):

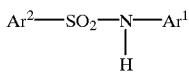

or a pharmaceutically acceptable salt, acid or ester thereof, wherein:

$Ar^1$ is a substituted with one or more substituents or an unsubstituted monocyclic or polycyclic heteroaryl group in which each substituent is independently selected from the group consisting of H, $NH_2$, halide, pseudohalide, alkyl, alkylcarbonyl, formyl, aryl, heteroaryl, alkoxyalkyl, alkylamino, alkylthio, arylcarbonyl, aryloxy, arylamino, arylthio, haloalkyl, haloaryl, and carbonyl, in which the aryl and alkyl portions are unsubstituted or substituted with any of the preceeding groups, or straight or branched chains of from about 1 up to about 12 carbons;

$Ar^2$ has the formula:

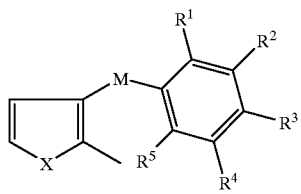

or

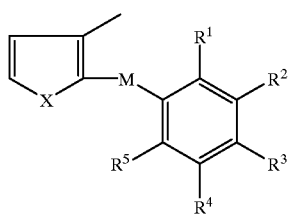

in which M is $(CH_2)_mC(O)(CH_2)_r$, $(CH_2)_mC(O)NH(CH_2)_r$, $(CH_2)_m(CH=CH)(CH_2)_r$, $(CH_2)_mC(O)(CH_2)_sNH(CH_2)_r$, $(CH_2)_m(CH=CH)(CH_2)_r$, $C=N(OH)(CH)_r$, $(CH_2)_mC(O)(CH=CH)_sNH(CH_2)_r$, $CH(OH)(CH_2)_r$, $CH(CH_3)C(O)(CH_2)_r$, $CH(CH_3)C(O)(CH_2)_m(CH=CH)(CH_2)_r$, $(CH_2)_r$, $(CH_2)_xO$, $(CH_2)S(O)_n$ wherein n is 0–2, or C(O)O, in which m, s and r are each independently 0 to 6; and $R^1$, $R^2$, $R^3$, $R^4$ and $R^5$ are each independently selected from (i) or (ii) as follows:

(i) $R^1$, $R^2$, $R^3$, $R^4$ and $R^5$ are each independently selected from among H, OH, $NHR^{38}$, $CONR^{38}R^{39}$, $NO_2$, cyano, halide, pseudohalide, alkyl, alkenyl, alkynyl, aryl, arylalkyl, heteroaryl, alkoxy, alkylamino, alkylthio, haloalkyl, alkylsulfinyl, alkylsulfonyl, alkoxycarbonyl, alkylcarbonyl, alkenylthio, alkenylamino, alkenyloxy, alkenylsulfinyl, alkenylsulfonyl, alkoxycarbonyl, arylaminocarbonyl, alkylaminocarbonyl, aminocarbonyl, (alkyl-aminocarbonyl)alkyl, acetoxy, hydroxyl, carboxyl, carboxyalkyl, carboxyalkenyl, alkylsulfonylaminoalkyl, cyanoalkyl, acetyl, acetoxyalkyl, hydroxyalkyl, alkyoxyalkoxy, hydroxyalkyl, (acetoxy)alkoxy, (hydroxy)alkoxy, formyl, sulfonyl chlorides, amino acids, hexoses, O-glycosides, riboses, lower alkyl, CN, $—(CH_2)_xC(O)(CH_2)_x$, $—(CH_2)_x$, $(CH_2)_xN$-lower alkyl, $—(CH_2)_xC(O)NH_2$, a D-, L- or racemic amino acid, a primary or secondary amide, $—S(O)_2NH_2$, acetoxyalkyl, $—(CH_2)_xCOOH$; $—(CH_2)_xCOOH—$, $CO_2$-lower alkyl, $—COC(O)(CH_2)_xCH_3$, $—(CH_2)_xN(CH_3)_2$, a sulfonyl chloride, $S(O)_2NHR^{50}$, alkylaryl, alkylheteroaryl, $C(O)NHR^{50}$, $—(CH_2)_xOH$, and $—C(O)N(H)N(H)M$; or (ii) at least two of $R^1$, $R^2$, $R^3$, $R^4$ and $R^5$, which substitute adjacent carbons on the ring, together form alkylenedioxy, alkylenethioxyoxy or alkylenedithioxy, which is unsubstituted or substituted by replacing one or more hydrogens with halide, lower alkyl, lower alkoxy or halo lower alkyl, and the others of $R^1$, $R^2$, $R^3$, $R^4$ and $R^5$ are selected as in (i);

at least four of $R^1$, $R^2$, $R^3$, $R^4$ and $R^5$ are not hydrogen, unless:

(a) $R^1$ and $R^3$ are alkyl and $R^5$ is $R^{20}$, which is selected from the group consisting of aryl, heteroaryl, heterocyclyl, OH, CN, $C(O)R^{16}$, $CO_2R^{16}$, SH, $S(O)_nR^{16}$ in which n is 0–2, a D, L or racemic amino acid, a ribose or hexose, an O-glycoside, a sulfonyl chloride, $—(CH_2)_xOH$, NHOH, $NR^{12}R^{16}$, $NO_2$, $N_3$, $OR^{16}$, $R^{12}NCOR^{16}$ and $CONR^{12}R^{16}$, then $R^2$ and $R^4$ are H or are selected as in (i) or (ii), above; or (b) when M is $—CONHC(R^{12})(R^{16})—$, then $R^1$, $R^2$, $R^3$, $R^4$ and $R^5$ may all be H; or (c) when M is $—COCHR^6—$, $Ar^1$ is not an isoxazolyl, $R^1$ is alkyl, and $R^3$ and $R^4$ form alkylenedioxy, then $R^2$ and $R^5$ are H or are selected as in (i) or (ii), above;

$R^{38}$ and $R^{39}$ are each independently selected from hydrogen, alkyl, alkenyl, alkynyl, aryl, haloalkyl alkylaryl, heterocyclyl, arylalkyl, arylalkoxy, alkoxy, aryloxy, cycloalkyl, cycloalkenyl and cycloalkynyl;

$R^6$ is H, or substituted or unsubstituted alkyl or aryl;

X is S, O or $NR^{11}$, where $R^{11}$ is hydrogen or has up to about 30 carbon atoms and is selected from the group consisting of hydrogen, alkyl, alkenyl, alkynyl, aryl, alkylaryl, heterocyclyl, aralkyl, aralkoxy, cycloalkyl, cycloalkenyl, cycloalkynyl, $C(O)R^{15}$ and $S(O)_nR^{15}$ in which n is 0–2;

$R^{15}$ is hydrogen, alkyl, alkenyl, alkynyl, aryl, alkylaryl, heterocyclyl, aralkyl, aralkoxy, cycloalkyl, cycloalkenyl, or cycloalkynyl;

$R^{11}$ and $R^{15}$ are unsubstituted or are substituted with one or more substituents each selected independently from Z;

Z is hydrogen, halide, pseudohalide, alkyl, alkoxy, alkenyl, alkynyl, aryl, amino acids, primary and secondary amides, O-glycosides, hexoses, riboses, alkylaryl, alkylheteroaryl, heterocyclyl, aralkyl, aralkoxy, cycloalkyl, cycloalkenyl, cycloalkynyl, OH, CN, $C(O)R^{16}$, $OC(O)R^{16}$, $CO_2R^{16}$, $OCO_2R^{16}$, SH, $S(O)_nR^{16}$ in which n is 0–2, NHOH, $NR^{12}R^{16}$, $NO_2$, $N_3$, $OR^{16}$, $R^{12}NCOR^{16}$ and $CONR^{12}R^{16}$; $R^{16}$ is hydrogen, alkyl, alkenyl, alkynyl, aryl, alkylaryl, heterocyclyl, aralkyl, aralkoxy, cycloalkyl, cycloalkenyl, cycloalkynyl, chloride, NHR$^{50}$, alkylaryl, alkylheteroaryl, or —(CH$_2$)$_x$OH; R$^{50}$ is a substituent such as hydrogen, lower alkyl, or lower alkoxy; R$^{12}$, which is selected independently from R$^{11}$ and Z, is selected from hydrogen, alkyl, alkenyl, alkynyl, aryl, alkylaryl, heterocyclyl, aralkyl, aralkoxy, cycloalkyl, cycloalkenyl, cycloalkynyl, C(O)R$^{17}$ and S(O)$_n$R$^{17}$ in which n is 0–2; R$^{17}$ is hydrogen, alkyl, alkenyl, alkynyl, aryl, alkylaryl, heterocyclyl, aralkyl, aralkoxy, cycloalkyl, cycloalkenyl or cycloalkynyl; or R$^{12}$ and R$^{16}$ together form alkylene; and each of R$^{12}$, R$^{15}$ and R$^{16}$ are unsubstituted or substituted with any group set forth for Z.

2. A compound or pharmaceutically acceptable salt, acid or ester thereof of claim 1, wherein M is selected from

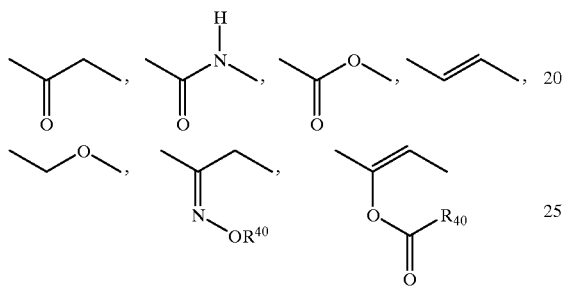

and

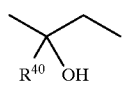

in which R$^{40}$ is hydrogen, alkyl, alkoxy, alkoxyalkyl or haloalkyl.

3. A compound or pharmaceutically acceptable salt, acid or ester thereof of claim 1, wherein M is C(O)CH$_2$, C(O)NH, —CH=CH—, CH$_2$CH$_2$C(O)(CH)$_2$, or CH$_2$CHC(O)CH$_2$.

4. A compound or pharmaceutically acceptable salt, acid or ester thereof of claim 1, wherein M is selected from among:

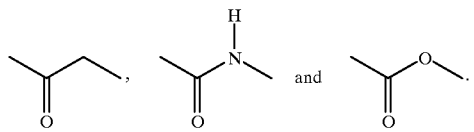

5. A sulfonamide compound or pharmaceutically acceptable salt, acid or ester thereof of claim 1 that has formula (I):

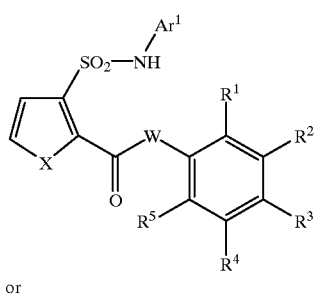

or

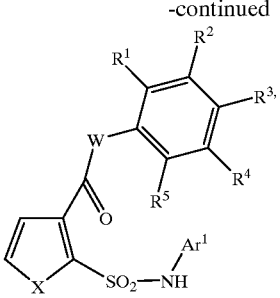

wherein:

Ar$^1$ is a substituted with one or more substituents or an unsubstituted monocyclic or polycyclic heteroaryl group in which each substituent is independently selected from the group consisting of H, NH$_2$, halide, pseudohalide, alkyl, alkylcarbonyl, formyl, aryl, heteroaryl, alkoxyalkyl, alkylamino, alkylthio, arylcarbonyl, aryloxy, arylamino, arylthio, haloalkyl, haloaryl, and carbonyl, in which the aryl and alkyl portions are unsubstituted or substituted with any of the preceeding groups, or straight or branched chains of from about 1 up to about 12 carbons;

X is S;

R$^{15}$ is hydrogen, alkyl, alkenyl, alkynyl, aryl, alkylaryl, heterocyclyl, aralkyl, aralkoxy, cycloalkyl, cycloalkenyl, or cycloalkynyl;

R$^{11}$ and R$^{15}$ are unsubstituted or are substituted with one or more substituents each selected independently from Z;

Z is selected from the group consisting of hydrogen, halide, pseudohalide, alkyl, alkoxy, alkenyl, alkynyl, aryl, amino acids, primary and secondary amides, O-glycosides, hexoses, riboses, alkylaryl, alkylheteroaryl, heterocyclyl, aralkyl, aralkoxy, cycloalkyl, cycloalkenyl, cycloalkynyl, OH, CN, C(O)R$^{16}$, OC(O)R$^{16}$, CO$_2$R$^{16}$, OCO$_2$R$^{16}$, SH, S(O)$_n$R$^{16}$ in which n is 0–2, NHOH, NR$^{12}$R$^{16}$, NO$_2$, N$_3$, OR$^{16}$, R$^{12}$NCOR$^{16}$ and CONR$^{12}$R$^{16}$;

R$^{16}$ is hydrogen, alkyl, alkenyl, alkynyl, aryl, alkylaryl, heterocyclyl, aralkyl, aralkoxy, cycloalkyl, cycloalkenyl, cycloalkynyl, chloride, NHR$^{50}$, alkylaryl, alkylheteroaryl, or —(CH$_2$)$_x$OH;

R$^{50}$ is hydrogen, lower alkyl, or lower alkoxy;

R$^{12}$, which is selected independently from R$^{11}$ and Z, is selected from the group consisting of hydrogen, alkyl, alkenyl, alkynyl, aryl, alkylaryl, heterocyclyl, aralkyl, aralkoxy, cycloalkyl, cycloalkenyl, cycloalkynyl, C(O)R$^{17}$ and S(O)$_n$R$^{17}$ in which n is 0–2;

R$^{17}$ is hydrogen, alkyl, alkenyl, alkynyl, aryl, alkylaryl, heterocyclyl, aralkyl, aralkoxy, cycloalkyl, cycloalkenyl or cycloalkynyl;

or R$^{12}$ and R$^{16}$ together form alkylene;

each of R$^{11}$, R$^{12}$, R$^{15}$ and R$^{16}$ are unsubstituted or substituted with the any of the appropriate groups of those set forth for Z;

W is =C(halo)$_2$, —(CH$_2$)$_x$—, =N(lower alkyl), —C(O)—, =C(lower alkyl)$_2$, —NH—, =NCOR$^{16}$, —NHC(R$^{12}$)(R$^{16}$)—, =NCO$_2$R$^{16}$, —CH$_2$— or =CHR$^6$; and each $_x$ is 0–3.

6. A sulfonamide or pharmaceutically acceptable salt, acid or ester thereof of claim 1, wherein the compounds of formula (A) are of formula (II):

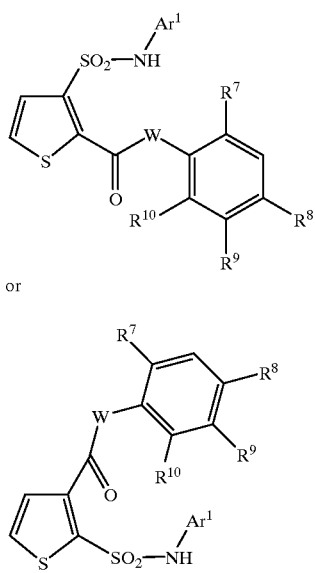

(II)

or wherein:
Ar¹ is a substituted or unsubstituted monocyclic or polycyclic heteroaryl group with one or more substituents, selected from the group consisting of H, NH₂, halide, pseudohalide, alkyl, alkylcarbonyl, formyl, aryl, heteroaryl, alkoxyalkyl, alkylamino, alkylthio, arylcarbonyl, aryloxy, arylamino, arylthio, haloalkyl, haloaryl, and carbonyl, in which the aryl and alkyl portions are unsubstituted or substituted with any of the preceeding groups, and straight or branched chains of from about 1 up to about 10–12 carbons;
R⁷ is R¹, R⁸ is R³, R⁹ is R⁴ and R¹⁰ is R⁵.

7. A sulfonamide or pharmaceutically acceptable salt, acid or ester thereof of claim 6, wherein R⁷, R⁸ and R¹⁰ are alkyl, haloalkyl, polyhaloalkyl, alkenyl having 1 to 2 double bonds, alkynyl having 1 to 2 triple bonds, cycloalkyl, cycloalkylalkyl, aryl, heteroaryl, arylalkyl, or heteroarylalkyl.

8. A sulfonamide or pharmaceutically acceptable salt, acid or ester thereof of claim 7, wherein R⁷, R⁸ and R¹⁰ are lower alkyl, lower alkenyl, lower alkynyl, or aryl.

9. A sulfonamide or pharmaceutically acceptable salt, acid or ester thereof of claim 8, wherein R⁷, R⁸ and R¹⁰ are methyl.

10. A sulfonamide or pharmaceutically acceptable salt, acid or ester thereof of claim 6, wherein R⁷, R⁸, R⁹ and R¹⁰ do not have cyano groups, and W is not —CH₂—.

11. A sulfonamide or pharmaceutically acceptable salt, acid or ester thereof of claim 6, wherein:
Ar¹ is benzo-2,1,3-thiadiazol-5-yl, benzo-2,1,3-oxadiazol-5-yl, 3-methoxy-2-pyrazinyl, 3,4-dimethyl-5-isoxazolyl, 4-chloro-3-methyl-5-isoxazolyl or 4-chloro-5-methyl-3-isoxazolyl;
W is —NH—, =NCO₂R¹⁶, or is —CH₂— when R⁹ is hydroxyl;
R⁷, R⁸ and R¹⁰ are methyl; and
R⁹ is selected from the group consisting of Z-substituted and unsubstituted alkyl, hydroxyl, substituted and unsubstituted alkoxy, OC(O)R¹⁶, OCO₂R¹⁶, NR¹²R¹⁶ and S(O)ₙR¹⁶ in which n is 0–2.

12. A sulfonamide or pharmaceutically acceptable salt, acid or ester thereof of claim 11, wherein R⁹ is selected from the group consisting of methoxy, methoxycarbonylmethoxy, 2-(2-methoxyethoxy)ethoxyacetoxy, 2-hydroxyethoxy, N,N-dimethylthiocarbonyloxy, N,N-dimethylthiocarbonyloxymethyl, dimethylamino, pyrrolidinyl, acetoxy, hydroxy, cyanomethyl, acetoxymethyl, hydroxymethyl, carboxylmethyl, methanesulfonylamino, N,N-dimethylaminomethyl, SO₂NH₂, and methoxycarbonylmethyl.

13. A sulfonamide or pharmaceutically acceptable salt, acid or ester thereof of claim 11, wherein R⁹ does not have a cyano group.

14. A sulfonamide or pharmaceutically acceptable salt, acid or ester thereof of claim 11, wherein R⁹ is selected from the group consisting of methoxy, methoxycarbonylmethoxy, 2-(2-methoxyethoxy)ethoxyacetoxy, 2-hydroxyethoxy, N,N-dimethylthiocarbonyloxy, N,N-dimethylthiocarbonyloxymethyl, dimethylamino, pyrrolidinyl, acetoxymethyl, methoxycarbonylmethyl, hydroxy and acetoxy.

15. A sulfonamide or pharmaceutically acceptable salt, acid or ester thereof of claim 6, selected from the group consisting of:
N-(4-chloro-3-methyl-5-isoxazolyl)-2-(3-carboxylmethyl-2,4,6-trimethylphenylaminocarbonyl)thiophene-3-sulfonamide;
N-(4-chloro-3-methyl-5-isoxazolyl)-2-(3-acetoxy-2,4,6-trimethylphenylaminocarbonyl)thiophene-3-sulfonamide;
N-(4-chloro-3-methyl-5-isoxazolyl)-2-(3-pyrrolidinyl-2,4,6-trimethylphenylaminocarbonyl)thiophene-3-sulfonamide;
N-(4-chloro-3-methyl-5-isoxazolyl)-2-(3-dimethylamino-2,4,6-trimethylphenylaminocarbonyl)thiophene-3-sulfonamide;
N-(4-chloro-3-methyl-5-isoxazolyl)-2-(3-(N,N-dimethylthiocarbonyloxymethyl-2,4,6-trimethylphenylaminocarbonyl)thiophene-3-sulfonamide;
N-(4-chloro-3-methyl-5-isoxazolyl)-2-(3-(N,N-dimethylthiocarbonyloxy)-2,4,6-trimethylphenylaminocarbonyl)thiophene-3-sulfonamide;
N-(4-chloro-3-methyl-5-isoxazolyl)-2-(3-(2-hydroxyethoxy)-2,4,6-trimethylphenylaminocarbonyl)thiophene-3-sulfonamide;
N-(4-chloro-3-methyl-5-isoxazolyl)-2-(3-(2-(2-methoxyethoxy)ethoxy)acetoxy-2,4,6-trimethylphenylaminocarbonyl)thiophene-3-sulfonamide;
N-(4-chloro-3-methyl-5-isoxazolyl)-2-(3-methoxycarbonylmethoxy-2,4,6-trimethylphenylaminocarbonyl)thiophene-3-sulfonamide;
N-(4-chloro-3-methyl-5-isoxazolyl)-2-(3-methoxy-2,4,6-trimethylphenylaminocarbonyl)thiophene-3-sulfonamide;
N-(4-chloro-3-methyl-5-isoxazolyl)-2-(3-methoxycarbonylmethyl-2,4,6-trimethylphenylaminocarbonyl)thiophene-3-sulfonamide;
N-(4-chloro-3-methyl-5-isoxazolyl)-2-(3-acetoxymethyl-2,4,6-trimethylphenylaminocarbonyl)thiophene-3-sulfonamide;
N-(4-chloro-3-methyl-5-isoxazolyl)-2-(3-hydroxy-2,4,6-trimethylphenylaminocarbonyl)thiophene-3-sulfonamide;

N-(4-chloro-3-methyl-5-isoxazolyl)-2-(3-dimethylaminomethyl-2,4,6-trimethylphenylaminocarbonyl)thiophene-3-sulfonamide;

N-(4-chloro-3-methyl-5-isoxazolyl)-2-(3-methanesulfonylamino-2,4,6-trimethylphenylaminocarbonyl)thiophene-3-sulfonamide;

N-(4-chloro-3-methyl-5-isoxazolyl)-2-(3-sulfamoyl-2,4,6-trimethylphenylaminocarbonyl)thiophene-3-sulfonamide;

N-(4-chloro-5-methyl-3-isoxazolyl)-2-(3-cyanomethyl-2,4,6-trimethylphenylaminocarbonyl)thiophene-3-sulfonamide;

N-(4-chloro-5-methyl-3-isoxazolyl)-2-(3-methoxycarbonylmethyl-2,4,6-trimethylphenylaminocarbonyl)thiophene-3-sulfonamide;

N-(4-chloro-5-methyl-3-isoxazolyl)-2-(3-carboxylmethyl-2,4,6-trimethylphenylaminocarbonyl)thiophene-3-sulfonamide;

N-(4-chloro-5-methyl-3-isoxazolyl)-2-(3-acetoxymethyl-2,4,6-trimethylphenylaminocarbonyl)thiophene-3-sulfonamide;

N-(4-chloro-5-methyl-3-isoxazolyl)-2-(3-hydroxymethyl-2,4,6-trimethylphenylaminocarbonyl)thiophene-3-sulfonamide;

N-(4-chloro-5-methyl-3-isoxazolyl)-2-(3-dimethylaminomethyl-2,4,6-trimethylphenylaminocarbonyl)thiophene-3-sulfonamide;

N-(4-chloro-5-methyl-3-isoxazolyl)-2-(3-methanesulfonylamino-2,4,6-trimethylphenylaminocarbonyl)thiophene-3-sulfonamide;

N-(4-chloro-5-methyl-3-isoxazolyl)-2-(3-hydroxy-2,4,6-trimethylphenylaminocarbonyl)thiophene-3-sulfonamide;

N-(4-chloro-5-methyl-3-isoxazolyl)-2-(3-carboxy-2,4,6-trimethylphenylaminocarbonyl)thiophene-3-sulfonamide;

N-(4-chloro-5-methyl-3-isoxazolyl)-2-(3-cyano-2,4,6-trimethylphenylaminocarbonyl)thiophene-3-sulfonamide;

N-(4-chloro-5-methyl-3-isoxazolyl)-2-(3-sulfamoyl-2,4,6-trimethylphenylaminocarbonyl)thiophene-3-sulfonamide;

N-(3,4-dimethyl-5-isoxazolyl)-2-(3-cyanomethyl-2,4,6-trimethylphenylaminocarbonyl)thiophene-3-sulfonamide;

N-(3,4-dimethyl-5-isoxazolyl)-2-(3-methoxycarbonylmethyl-2,4,6-trimethylphenylaminocarbonyl)thiophene-3-sulfonamide;

N-(3,4-dimethyl-5-isoxazolyl)-2-(3-carboxylmethyl-2,4,6-trimethylphenylaminocarbonyl)thiophene-3-sulfonamide;

N-(3,4-dimethyl-5-isoxazolyl)-2-(3-acetoxymethyl-2,4,6-trimethylphenylaminocarbonyl)thiophene-3-sulfonamide;

N-(3,4-dimethyl-5-isoxazolyl)-2-(3-hydroxymethyl-2,4,6-trimethylphenylaminocarbonyl)thiophene-3-sulfonamide;

N-(3,4-dimethyl-5-isoxazolyl)-2-(3-dimethylaminomethyl-2,4,6-trimethylphenylaminocarbonyl)thiophene-3-sulfonamide;

N-(3,4-dimethyl-5-isoxazolyl)-2-(3-methanesulfonylamino-2,4,6-trimethylphenylaminocarbonyl)thiophene-3-sulfonamide;

N-(3,4-dimethyl-5-isoxazolyl)-2-(3-hydroxy-2,4,6-trimethylphenylaminocarbonyl)thiophene-3-sulfonamide;

N-(3,4-dimethyl-5-isoxazolyl)-2-(3-carboxy-2,4,6-trimethylphenylaminocarbonyl)thiophene-3-sulfonamide;

N-(3,4-dimethyl-5-isoxazolyl)-2-(3-cyano-2,4,6-trimethylphenylaminocarbonyl)thiophene-3-sulfonamide;

N-(3,4-dimethyl-5-isoxazolyl)-2-(3-sulfamoyl-2,4,6-trimethylphenylaminocarbonyl)thiophene-3-sulfonamide;

N-(benzo-2,1,3-thiadiazol-5-yl)-2-(3-cyanomethyl-2,4,6-trimethylphenylaminocarbonyl)thiophene-3-sulfonamide;

N-(benzo-2,1,3-thiadiazol-5-yl)-2-(3-methoxycarbonylmethyl-2,4,6-trimethylphenylaminocarbonyl)thiophene-3-sulfonamide;

N-(benzo-2,1,3-thiadiazol-5-yl)-2-(3-carboxylmethyl-2,4,6-trimethylphenylaminocarbonyl)thiophene-3-sulfonamide;

N-(benzo-2,1,3-thiadiazol-5-yl)-2-(3-acetoxymethyl-2,4,6-trimethylphenylaminocarbonyl)thiophene-3-sulfonamide;

N-(benzo-2,1,3-thiadiazol-5-yl)-2-(3-hydroxymethyl-2,4,6-trimethylphenylaminocarbonyl)thiophene-3-sulfonamide;

N-(benzo-2,1,3-thiadiazol-5-yl)-2-(3-dimethylaminomethyl-2,4,6-trimethylphenylaminocarbonyl)thiophene-3-sulfonamide;

N-(benzo-2,1,3-thiadiazol-5-yl)-2-(3-methanesulfonylamino-2,4,6-trimethylphenylaminocarbonyl)thiophene-3-sulfonamide;

N-(benzo-2,1,3-thiadiazol-5-yl)-2-(3-hydroxy-2,4,6-trimethylphenylaminocarbonyl)thiophene-3-sulfonamide;

N-(benzo-2,1,3-thiadiazol-5-yl)-2-(3-carboxy-2,4,6-trimethylphenylaminocarbonyl)thiophene-3-sulfonamide;

N-(benzo-2,1,3-thiadiazol-5-yl)-2-(3-cyano-2,4,6-trimethylphenylaminocarbonyl)thiophene-3-sulfonamide;

N-(benzo-2,1,3-thiadiazol-5-yl)-2-(3-sulfamoyl-2,4,6-trimethylphenylaminocarbonyl)thiophene-3-sulfonamide;

N-(3-methoxy-2-pyrazinyl)-2-(3-cyanomethyl-2,4,6-trimethylphenylaminocarbonyl)thiophene-3-sulfonamide;

N-(3-methoxy-2-pyrazinyl)-2-(3-methoxycarbonylmethyl-2,4,6-trimethylphenylaminocarbonyl)thiophene-3-sulfonamide;

N-(3-methoxy-2-pyrazinyl)-2-(3-carboxylmethyl-2,4,6-trimethylphenylaminocarbonyl)thiophpene-3-sulfonamide;

N-(3-methoxy-2-pyrazinyl)-2-(3-acetoxymethyl-2,4,6-trimethylphenylaminocarbonyl)thiophene-3-sulfonamide;

N-(3-methoxy-2-pyrazinyl)-2-(3-hydroxymethyl-2,4,6-trimethylphenylaminocarbonyl)thiophene-3-sulfonamide;

N-(3-methoxy-2-pyrazinyl)-2-(3-dimethylaminomethyl-2,4,6-trimethylphenylaminocarbonyl)thiophene-3-sulfonamide;

N-(3-methoxy-2-pyrazinyl)-2-(3-methanesulfonylamino-2,4,6-trimethylphenylaminocarbonyl)thiophene-3-sulfonamide;

N-(3-methoxy-2-pyrazinyl)-2-(3-hydroxy-2,4,6-trimethylphenylaminocarbonyl)thiophene-3-sulfonamide;

N-(3-methoxy-2-pyrazinyl)-2-(3-carboxy-2,4,6-trimethylphenylaminocarbonyl)thiophene-3-sulfonamide;

N-(3-methoxy-2-pyrazinyl)-2-(3-cyano-2,4,6-trimethylphenylaminocarbonyl)thiophene-3-sulfonamide;

N-(3-methoxy-2-pyrazinyl)-2-(3-sulfamoyl-2,4,6-trimethylphenylaminocarbonyl)thiophene-3-sulfonamide;

N-(4-chloro-3-methyl-5-isoxazolyl)-2-(1-methyl-1-phenyl-1-ethylaminocarbonyl)thiophene-3-sulfonamide;

N-(4-chloro-3-methyl-5-isoxazolyl)-2-((R)-1-phenyl-1-ethylaminocarbonyl)thiophene-3-sulfonamide;

N-(4-chloro-3-methyl-5-isoxazolyl)-2-((S)-1-phenyl-1-ethylaminocarbonyl)thiophene-3-sulfonamide; and pharmaceutically acceptable salts, acids and esters thereof.

16. A sulfonamide or pharmaceutically acceptable salt, acid or ester thereof of claim 6, selected from the group consisting of:

N-(4-chloro-3-methyl-5-isoxazolyl)-2-(3-methoxycarbonylmethyl-2,4,6-trimethylphenylaminocarbonyl)thiophene-3-sulfonamide;

N-(4-chloro-3-methyl-5-isoxazolyl)-2-(3-acetoxymethyl-2,4,6-trimethylphenylaminocarbonyl)thiophene-3-sulfonamide;

N-(4-chloro-3-methyl-5-isoxazolyl)-2-(3-hydroxy-2,4,6-trimethylphenylaminocarbonyl)thiophene-3-sulfonamide;

N-(4-chloro-3-methyl-5-isoxazolyl)-2-(3-methoxy-2,4,6-trimethylphenylaminocarbonyl)thiophene-3-sulfonamide;

N-(4-chloro-3-methyl-5-isoxazolyl)-2-(3-methoxycarbonylmethoxy-2,4,6-trimethylphenylaminocarbonyl)thiophene-3-sulfonamide;

N-(4-chloro-3-methyl-5-isoxazolyl)-2-(3-(2-(2-methoxyethoxy)ethoxy)acetoxy-2,4,6-trimethylphenylaminocarbonyl)thiophene-3-sulfonamide;

N-(4-chloro-3-methyl-5-isoxazolyl)-2-(3-(2-hydroxyethoxy)-2,4,6-trimethylphenylaminocarbonyl)thiophene-3-sulfonamide;

N-(4-chloro-3-methyl-5-isoxazolyl)-2-(3-(N,N-dimethylthiocarbonyloxy)-2,4,6-trimethylphenylaminocarbonyl)thiophene-3-sulfonamide;

N-(4-chloro-3-methyl-5-isoxazolyl)-2-(3-(N,N-dimethylthiocarbonyloxymethyl-2,4,6-trimethylphenylaminocarbonyl)thiophene-3-sulfonamide;

N-(4-chloro-3-methyl-5-isoxazolyl)-2-(3-dimethylamino-2,4,6-trimethylphenylaminocarbonyl)thiophene-3-sulfonamide;

N-(4-chloro-3-methyl-5-isoxazolyl)-2-(3-pyrrolidinyl-2,4,6-trimethylphenylaminocarbonyl)thiophene-3-sulfonamide;

N-(4-chloro-3-methyl-5-isoxazolyl)-2-(3-acetoxy-2,4,6-trimethylphenylaminocarbonyl)thiophene-3-sulfonamide; and pharmaceutically acceptable salts, acids and esters thereof.

17. A sulfonamide compound or pharmaceutically acceptable salt, acid or ester thereof of claim 1, wherein $Ar^1$ has formula:

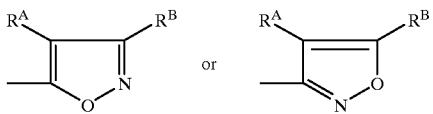

in which $R^A$ and $R^B$ are either (i), (ii) or (iii) as follows:
(i) $R^A$ and $R^B$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, and substituted or unsubstituted ureido, in which the alkyl, alkenyl and alkynyl portions have from 1 up to about 14 carbon atoms and are either straight or branched chains or cyclic, and the aryl portions have from about 4 to about 16 carbons, except that $R^2$ is not halide or pseudohalide; or,
(ii) $R^A$ and $R^B$ together form $—(CH_2)_n$, where n is 3 to 6; or,
(iii) $R^A$ and $R^B$ together form 1,3-butadienyl.

18. A sulfonamide compound or pharmaceutically acceptable salt, acid or ester thereof of claim 17, wherein $R^A$ and $R^B$ are each selected independently from among alkyl, lower alkenyl, lower alkynyl, lower haloalkyl, halide, pseudohalide or H, except that $R^B$ is not halide.

19. A sulfonamide compound or pharmaceutically acceptable salt, acid or ester thereof of claim 1 that is a thiophene-3-sulfonamide.

20. A sulfonamide compound or pharmaceutically acceptable salt, acid or ester thereof of claim 6, wherein $Ar^1$ has formula:

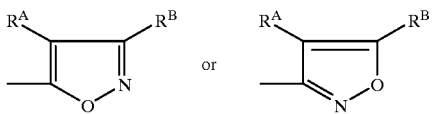

in which $R^A$ and $R^B$ are either (i), (ii) or (iii) as follows:
(i) $R^A$ and $R^B$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, and substituted or unsubstituted ureido, in which the alkyl, alkenyl and alkynyl portions have from 1 up to about 14 carbon atoms and are either straight or branched chains or cyclic, and the aryl portions have from about 4 to about 16 carbons, except that $R^2$ is not halide or pseudohalide; or,
(ii) $R^A$ and $R^B$ together form $—(CH_2)_n$, where n is 3 to 6; or,
(iii) $R^A$ and $R^B$ together form 1,3-butadienyl.-

21. A sulfonamide compound or pharmaceutically acceptable salt, acid or ester thereof of claim 20, wherein $R^A$ and $R^B$ are each selected independently from among alkyl, lower alkenyl, lower alkynyl, lower haloalkyl, halide, pseudohalide or H, except that $R^B$ is not halide.

22. A sulfonamide compound or pharmaceutically acceptable salt, acid or ester thereof of claim 6 that is a thiophene-3-sulfonamide.

23. A sulfonamide compound or pharmaceutically acceptable salt, acid or ester thereof of claim 1 that has formula III:

(III)

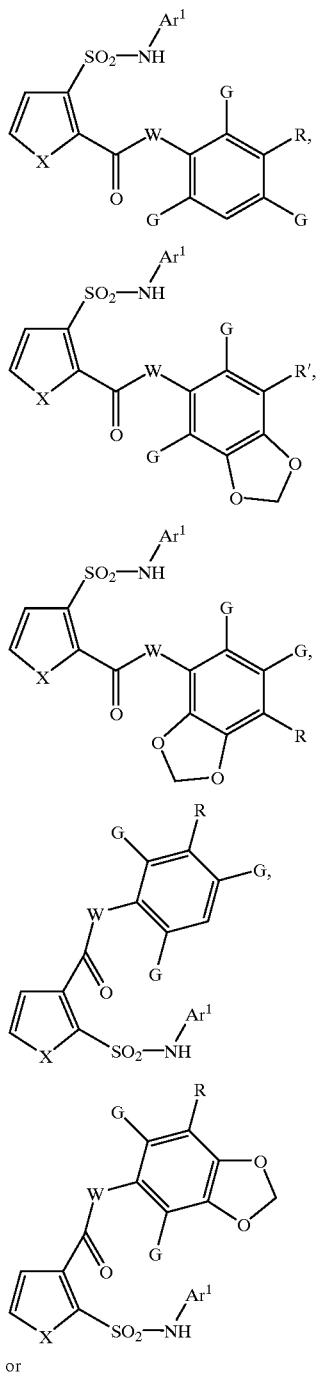

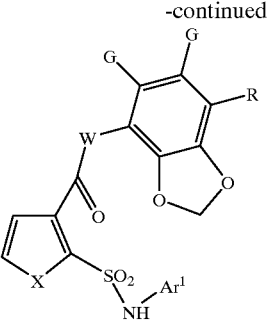

wherein:

X is S, O or $NR^{11}$;

each G and R is independently selected from lower alkyl, CN, $-(CH_2)_xC(O)(CH_2)_x$, $-(CH_2)_x$, $(CH_2)_x$N-lower alkyl, $-(CH_2)_xC(O)NH_2$, a D-, L- or racemic amino acid, a primary or secondary amide, O-glycoside, a hexose or ribose, $-S(O)_2NH_2$, hydroxy, alkoxy, alkoxycarbonyl, acetoxyalkyl, $-(CH_2)_xCOOH$; $-(CH_2)_xCOOH-$, $CO_2$-lower alkyl, heteroaryl, $-COC(O)(CH_2)_xCH_3$, $-(CH_2)_xN(CH_3)_2$, a sulfonyl chloride, $S(O)_2NHR^{50}$, alkylaryl, alkylheteroaryl, $C(O)NHR^{50}$, $-(CH_2)_xOH$, and $-C(O)N(H)N(H)M$;

$R^{50}$ is hydrogen, lower alkyl, or lower alkoxy;

M is H or $R^{50}$;

R' is independently selected from hydrogen, G and R;

W is $=C(halo)_2$, $=N(H)$, $-(CH_2)_x-$, $=N(lower\ alkyl)$, $-C(O)-$, $=C(lower\ alkyl)_2$; and each x is independently is 0–3.

24. The sulfonamides of claim 23, wherein $Ar^1$ is an isoxazolyl, a thiazolyl, a pyrimidinyl or a pyridazinyl group.

25. The sulfonamides of claim 23, wherein $Ar^1$ is isoxazolyl.

26. The sulfonamides of claim 23, wherein: R, G and R' are selected where the amino acid is L-Asp or L-Glu; the hexose is D-mannose, the heteroaryl is triazolyl, and X is S.

27. The sulfonamides of claim 25, wherein: R, G and R' are selected where the amino acid is L-Asp or L-Glu; the hexose is D-mannose, the heteroaryl is triazo and X is S.

28. A sulfonamide or pharmaceutically acceptable acid, salt or ester of a compound of claim 1, with the provisos that where $Ar^1$ is 4-chloro-3-methyl-5-isoxazolyl and W is $-NH-$:

(a) if $R^1$, $R^3$ and $R^5$ are methyl, and $R^4$ is H; then $R^2$ is not cyanomethyl, hydroxymethyl, cyano, methoxycarbonyl, carboxyl, methanesulfonyl, 2-hydroxyethyl;

(b) if $R^1$ is methoxy or is methyl when $R^2$ and $R^3$ together form methylenedioxy, $R^2$ and $R^3$ are methoxy or together form methylenedioxy, and $R^4$ is H; then $R^5$ is not methyl, cyano, acetyl, methoxycarbonyl, carboxyl, methanesulfonyl, cyanomethyl or 2-hydroxyethyl, and is not methoxy when $R^1$ is methyl;

(c) if $R^1$ is cyano or acetyl, $R^2$ and $R^3$ together form methylenedioxy, and $R^4$ is H; then $R^5$ is not methyl or methoxy; and (d) if $R^1$ is cyanomethyl, $R^2$ and $R^3$ together form methylenedioxy, and $R^4$ is H; then $R^5$ is not cyanomethyl.

29. A sulfonamide compound or pharmaceutically acceptable acid, salt or ester of a compound of claim 28, wherein, when $Ar^1$ is 4-chloro-3-methyl-5-isoxazolyl and W is $-CH_2-$:

(a) if R¹, R³ and R⁵ are methyl, and R⁴ is H; then R² is not cyanomethyl, hydroxymethyl, cyano, methoxycarbonyl, carboxyl, methanesulfonyl, 2-hydroxyethyl;

(b) if R¹ is methoxy when R² and R³ are methoxy or together form methylenedioxy, or is methyl when R² and R³ together form methylenedioxy, and R⁴ is H; then R⁵ is not: (i) methyl, acetyl, methoxycarbonyl, carboxyl, methanesulfonyl, cyanomethyl or 2-hydroxyethyl, and additionally (ii) is not methoxy or cyano when R¹ is methyl, and (iii) is not cyano when R¹ is methoxy and R² and R³ together form methylenedioxy; and (c) if R¹ is cyano or acetyl, R² and R³ together form methylenedioxy, and R⁴ is H; then R⁵ is not methyl or methoxy.

30. The sulfonamides of claim 23, wherein:
W is =CH₂, =NH, =NCH₃, =NCH₂CH₃, =C(CH₃)₂ or CF₂; and
G is —CH₃, —CN, —COCH₃, —CH₂CH₃, —(CH₂)ₓCO₂H.

31. The sulfonamides of claim 24, wherein:
W is =CH₂, =NH, =NCH₃, =NCH₂CH₃, =C(CH₃)₂ or CF₂; and
G is —CH₃, —CN, —COCH₃, —CH₂CH₃, —(CH₂)ₓCO₂H.

32. The sulfonamides of claim 25, wherein:
W is =CH₂, =NH, =NCH₃, =NCH₂CH₃, =C(CH₃)₂ or CF₂; and
G is —CH₃, —CN, —COCH₃, —CH₂CH₃, —(CH₂)ₓCO₂H.

33. A sulfonamide or pharmaceutically acceptable salt, acid or ester thereof of claim 23 is selected from the group consisting of:

N²-(3-cyanomethyl-2,4,6-trimethylphenyl)-3-(4-chloro-3-methyl-5-isoxazolylsulfamoyl)-2-thiophenecarboxamide;
methyl-2-(3-(3-(4-chloro-3-methyl-5-isoxazolylsulfamoyl)-2-thienylcarboxamido)-2,4,6-trimethylphenyl)acetate;
2-(3-(3-(4-chloro-3-methyl-5-isoxazolylsulfamoyl)-2-thienylcarboxamido)-2,4,6-trimethylphenyl)acetic acid;
N²-(3-acetyloxymethyl-2,4,6-trimethylphenyl)-3-(4-chloro-3-methyl-5-isoxazolylsulfamoyl)-2-thiophenecarboxamide;
N²-(3-hydroxymethyl-2,4,6-trimethylphenyl)-3-(4-chloro-3-methyl-5-isoxazolylsulfamoyl)-2-thiophenecarboxamide;
N²-(3-dimethylaminomethyl-2,4,6-trimethylphenyl)-3-(4-chloro-3-methyl-5-isoxazolylsulfamoyl)-2-thiophenecarboxamide trifluoroacetate;
N²-(3-(4,5-dihydro-1,3-oxazol-2-yl)-2,4,6-trimethylphenyl)-3-(4-chloro-3-methyl-5-isoxazolylsulfamoyl)-2-thiophenecarboxamide;
3-(3-(4-chloro-3-methyl-5-isoxazolylsulfamoyl)-2-thienylcarboxamido)-2,4,6-trimethylbenzoic acid;
N-[3-(3-(4-chloro-3-methyl-5-isoxazolylsulfamoyl)-2-thienylcarboxamido)-2,4,6-trimethylbenzoyl]glutamic acid;
N-[3-(3-(4-chloro-3-methyl-5-isoxazolylsulfamoyl)-2-thienylcarboxamido)-2,4,6-trimethylbenzoyl]aspartic acid;
N-[2-(3-(3-(4-chloro-3-methyl-5-isoxazolylsulfamoyl)-2-thienylcarboxamido)-2,4,6-trimethylphenyl)acetyl]glutamic acid;
N-[2-(3-(3-(4-chloro-3-methyl-5-isoxazolylsulfamoyl)-2-thienylcarboxamido)-2,4,6-trimethylphenyl)acetyl]aspartic acid;
N²-(3-cyano-2,4,6-trimethylphenyl)-3-(4-chloro-3-methyl-5-isoxazolylsulfamoyl)-2-thiophenecarboxamide;
2-(3-(3-(4-chloro-3-methyl-5-isoxazolylsulfamoyl)-2-thienylcarboxamido)-2,4,6-trimethylphenoxy)acetic acid;
N²-(3-alkylsulfonamido-2,4,6-trimethylphenyl)-3-(4-chloro-3-methyl-5-isoxazolylsulfamoyl)-2-thiophenecarboxamide;
N²-(3-arylsulfonamido-2,4,6-trimethylphenyl)-3-(4-chloro-3-methyl-5-isoxazolylsulfamoyl)-2-thiophenecarboxamide;
N²-(3-sulfamoyl-2,4,6-trimethylphenyl)-3-(4-chloro-3-methyl-5-isoxazolylsulfamoyl)-2-thiophenecarboxamide;
N²-(3-alkylsulfamoyl-2,4,6-trimethylphenyl)-3-(4-chloro-3-methyl-5-isoxazolylsulfamoyl)-2-thiophenecarboxamide;
N²-(3-arylsulfamoyl-2,4,6-trimethylphenyl)-3-(4-chloro-3-methyl-5-isoxazolylsulfamoyl)-2-thiophenecarboxamide;
N²-(3-(1H-1,2,3,4-tetraazol-5-ylmethyl)-2,4,6-trimethylphenyl)-3-(4-chloro-3-methyl-5-isoxazolylsulfamoyl)-2-thiophenecarboxamide;
N²-(3-(2-pyridylmethyl)-2,4,6-trimethylphenyl)-3-(4-chloro-3-methyl-5-isoxazolylsulfamoyl)-2-thiophenecarboxamide;
N²-(3-hydrazinocarbonyl-2,4,6-trimethylphenyl)-3-(4-chloro-3-methyl-5-isoxazolylsulfamoyl)-2-thiophenecarboxamide;
N²-(3-aminomethyl-2,4,6-trimethylphenyl)-3-(4-chloro-3-methyl-5-isoxazolylsulfamoyl)-2-thiophenecarboxamide;
N²-(3-(α-D-mannopyranosyloxymethyl)-2,4,6-trimethylphenyl)-3-(4-chloro-3-methyl-5-isoxazolylsulfamoyl)-2-thiophenecarboxamide;
5-(3-(4-chloro-3-methyl-5-isoxazolylsulfamoyl)-2-thienylcarboxamido)-4-cyano-6-methylbenzo[d][1,3]dioxole;
5-(3-(4-chloro-3-methyl-5-isoxazolylsulfamoyl)-2-thienylcarboxamido)-6-cyano-4-methylbenzo[d][1,3]dioxole;
2-(5-(3-(4-chloro-3-methyl-5-isoxazolylsulfamoyl)-2-thienylcarboxamido)-4-methylbenzo[d][1,3]dioxole)-6-acetic acid;
5-(3-(4-chloro-3-methyl-5-isoxazolylsulfamoyl)-2-thienylcarboxamido)-4-acetyl-6-methylbenzo[d][1,3]dioxole;
5-(3-(4-chloro-3-methyl-5-isoxazolylsulfamoyl)-2-thienylcarboxamido)-6-acetyl-4-methylbenzo[d][1,3]dioxole;
5-(3-(4-chloro-3-methyl-5-isoxazolylsulfamoyl)-2-thienylcarboxamido)-7-cyano-4,6-dimethylbenzo[d][1,3]dioxole;
6-(3-(4-chloro-3-methyl-5-isoxazolylsulfamoyl)-2-thienylcarboxamido)-5,7-dimethylbenzo[d][1,3]dioxole-4-carboxylic acid;
7-(3-(4-chloro-3-methyl-5-isoxazolylsulfamoyl)-2-thienylcarboxamido)-5,6-dimethylbenzo[d][1,3]dioxole-4-carboxylic acid;
7-(3-(4-chloro-3-methyl-5-isoxazolylsulfamoyl)-2-thienylcarboxamido)-4-cyano-5,6-dimethylbenzo[d][1,3]dioxole;
7-(3-(4-chloro-3-methyl-5-isoxazolylsulfamoyl)-2-thienylcarboxamido)-4-acetyl-5,6-dimethylbenzo[d][1,3]dioxole;
7-(3-(4-chloro-3-methyl-5-isoxazolylsulfamoyl)-2-thienylcarboxamido)-4-carboxamido-5,6-dimethylbenzo[d][1,3]dioxole;
7-(3-(4-chloro-3-methyl-5-isoxazolylsulfamoyl)-2-thienylcarboxamido)-4-aminomethyl-5,6-dimethylbenzo[d][1,3]dioxole;

7-(3-(4-chloro-3-methyl-5-isoxazolylsulfamoyl)-2-thienylcarboxamido)-4-dimethylaminomethyl-5,6-dimethylbenzo[d][1,3]dioxole;

N-(4-chloro-3-methyl-5-isoxazolyl)-2-(3-cyanomethyl-2,4,6-trimethylphenylaminocarbonyl)thiophene-3-sulfonamide, N-(4-chloro-3-methyl-5-isoxazolyl)-2-(3-carboxymethyl-2,4,6-trimethylphenylaminocarbonyl)thiophene-3-sulfonamide;

N-(4-chloro-3-methyl-5-isoxazolyl)-2-(3-acetoxymethyl-2,4,6-trimethylphenylaminocarbonyl)thiophene-3-sulfonamide;

N-(4-chloro-3-methyl-5-isoxazolyl)-2-(3-hydroxymethyl-2,4,6-trimethylphenylaminocarbonyl)thiophene-3-sulfonamide; and pharmaceutically acceptable salts, esters and acids thereof.

34. A compound of claim 33 that is a sodium salt.

35. A sulfonamide compound or pharmaceutically acceptable salt, acid or ester thereof of claim 23, wherein $Ar^1$ has formula:

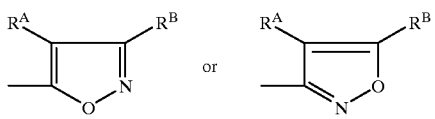

in which $R^A$ and $R^B$ are either (i), (ii) or (iii) as follows:
(i) $R^A$ and $R^B$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, and substituted or unsubstituted ureido, in which the alkyl, alkenyl and alkynyl portions have from 1 up to about 14 carbon atoms and are either straight or branched chains or cyclic, and the aryl portions have from about 4 to about 16 carbons, except that $R^2$ is not halide or pseudohalide; or,
(ii) $R^A$ and $R^B$ together form $-(CH_2)_n$-, where n is 3 to 6; or,
(iii) $R^A$ and $R^B$ together form 1,3-butadienyl.

36. A sulfonamide compound or pharmaceutically acceptable salt, acid or ester thereof of claim 35, wherein $R^A$ and $R^B$ are each selected independently from among alkyl, lower alkenyl, lower alkynyl, lower haloalkyl, halide, pseudohalide and H, except that $R^B$ is not halide.

37. A sulfonamide compound or pharmaceutically acceptable salt, acid or ester thereof of claim 23 that is a thiophene-3-sulfonamide.

38. A sulfonamide or pharmaceutically acceptable salt, acid or ester thereof of claim 1, wherein the compounds of formula (A) are of formula (IV):

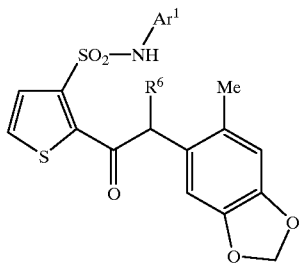

or

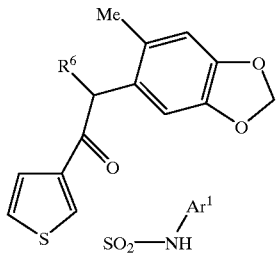

(IV)

wherein:
$Ar^1$ is selected with the proviso that $Ar^1$ is not 4-chloro-3-methyl-5-isoxazolyl, 4-chloro-5-methyl-3-isoxazolyl or 3,4-dimethyl-5-isoxazolyl when $R^6$ is H; and
$R^6$ is H, or substituted or unsubstituted alkyl or aryl.

39. A sulfonamide or pharmaceutically acceptable salt, acid or ester thereof of claim 38, wherein:
$Ar^1$ is benzo-2,1,3-oxadiazol-5-yl or 2-methoxy-3-pyrazinyl; and
$R^6$ is H, or substituted or unsubstituted alkyl.

40. A sulfonamide or pharmaceutically acceptable salt, acid or ester thereof of claim 38, wherein $R^6$ is methyl or carboxymethyl.

41. A sulfonamide compound or pharmaceutically acceptable salt, acid or ester thereof of claim 38, wherein $Ar^1$ has formula:

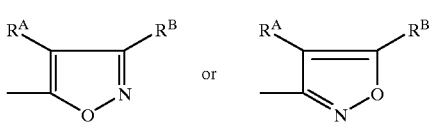

in which
$R^A$ and $R^B$ are either (i), (ii) or (iii) as follows:
(i) $R^A$ and $R^B$ are each independently selected from H, $NH_2$, $NO_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, and substituted or unsubstituted ureido, in which the alkyl, alkenyl and alkynyl portions have from 1 up to about 14 carbon atoms and are either straight or branched chains or cyclic, and the aryl portions have from about 4 to about 16 carbons, except that $R^2$ is not halide or pseudohalide; or,
(ii) $R^A$ and $R^B$ together form $-(CH_2)_n$-, where n is 3 to 6; or,
(iii) $R^A$ and $R^B$ together form 1,3-butadienyl.

42. A sulfonamide compound or pharmaceutically acceptable salt, acid or ester thereof of claim 41, wherein $R^A$ and $R^B$ are each selected independently from among alkyl, lower alkenyl, lower alkynyl, lower haloalkyl, halide, pseudohalide and H, except that $R^B$ is not halide.

43. A sulfonamide compound or pharmaceutically acceptable salt, acid or ester thereof of claim 38 that is a thiophene-3-sulfonamide.

44. A sulfonamide or pharmaceutically acceptable salt, acid or ester thereof of claim 38, selected from the group consisting of:
N-(benzo-2,1,3-oxadiazol-5-yl)-2-(2-methyl-4,5-methylenedioxyphenylacetyl)thiophene-3-sulfonamide;
N-(3-methoxy-2-pyrazinyl)-2-(2-methyl-4,5-methylenedioxyphenylacetyl)thiophene-3-sulfonamide;
N-(4-chloro-3-methyl-5-isoxazolyl)-2-(2-(2-methyl-4,5-methylenedioxyphenyl)propanoyl)thiophene-3-sulfonamide;
N-(4-chloro-3-methyl-5-isoxazolyl)-2-(2-(3-carboxyl-2-(2-methyl-4,5-methylenedioxyphenyl)propanoyl)thiophene-3-sulfonamide; and
pharmaceutically acceptable salts, esters and acids thereof.

45. A compound of claim 44 that is a sodium salt.

46. A sulfonamide or pharmaceutically acceptable salt, acid or ester thereof of claim 1, wherein the compounds of formula (A) are of formula (V):

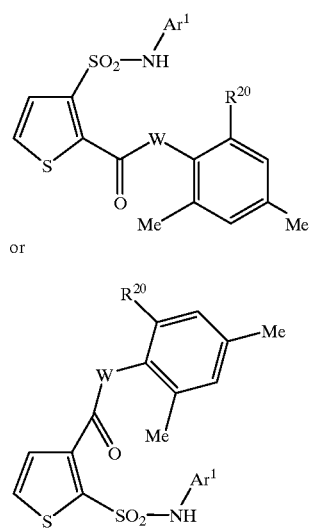

(V)

wherein:
W is —NH—; and
$R^{20}$ is selected from the group consisting of aryl, heteroaryl, heterocycle, OH, CN, C(O)$R^{16}$, CO$_2R^{16}$, SH, S(O)$_nR^{16}$ in which n is 0–2, a D, L or racemic amino acid, a ribose or hexose, an O-glycoside, a sulfonyl chloride, —(CH$_2$)$_x$OH, NHOH, NR$^{12}R^{16}$, NO$_2$, N$_3$, OR$^{16}$, R$^{12}$NCOR$^{16}$ and CONR$^{12}R^{16}$;
$R^{16}$ is hydrogen, alkyl, alkenyl, alkynyl, aryl, alkylaryl, heterocycle, aralkyl, aralkoxy, cycloalkyl, cycloalkenyl or cycloalkynyl;
$R^{12}$ is selected from hydrogen, alkyl, alkenyl, alkynyl, aryl, alkylaryl, heterocycle, aralkyl, aralkoxy, cycloalkyl, cycloalkenyl, cycloalkynyl, C(O)$R^{17}$ and S(O)$_nR^{17}$ in which n is 0–2;
$R^{17}$ is hydrogen, alkyl, alkenyl, alkynyl, aryl, alkylaryl, heterocycle, aralkyl, aralkoxy, cycloalkyl, cycloalkenyl or cycloalkynyl; and each of $R^{12}$, $R^{15}$ and $R^{16}$ are unsubstituted or substituted with the any of the groups set forth for Z.

47. A sulfonamide compound or pharmaceutically acceptable salt, acid or ester thereof of claim 46, wherein Ar$^1$ has formula:

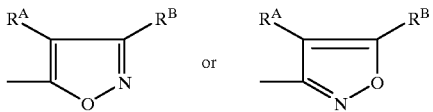

in which
$R^A$ and $R^B$ are either (i), (ii) or (iii) as follows:
(i) $R^A$ and $R^B$ are each independently selected from H, NH$_2$, NO$_2$, halide, pseudohalide, alkyl, alkenyl, alkynyl, aryl, arylalkyl, heteroaryl, alkoxy, alkylamino, alkylthio, alkyloxy, haloalkyl, alkylsufinyl, alkylsulfonyl, aryloxy, arylamino, arylthio, arylsufinyl, arylsulfonyl, haloalkyl, haloaryl, alkoxycarbonyl, alkylcarbonyl, aminocarbonyl, arylcarbonyl, formyl, substituted or unsubstituted amido, and substituted or unsubstituted ureido, in which the alkyl, alkenyl and alkynyl portions have from 1 up to about 14 carbon atoms and are either straight or branched chains or cyclic, and the aryl portions have from about 4 to about 16 carbons, except that $R^2$ is not halide or pseudohalide; or,
(ii) $R^A$ and $R^B$ together form —(CH$_2$)$_n$, where n is 3 to 6; or,
(iii) $R^A$ and $R^B$ together form 1,3-butadienyl.

48. A sulfonamide compound or pharmaceutically acceptable salt, acid or ester thereof of claim 47, wherein $R^A$ and $R^B$ are each selected independently from among alkyl, lower alkenyl, lower alkynyl, lower haloalkyl, halide, pseudohalide and H, except that $R^B$ is not halide.

49. A sulfonamide compound or pharmaceutically acceptable salt, acid or ester thereof of claim 46 that is a thiophene-3-sulfonamide.

50. A sulfonamide or pharmaceutically acceptable salt, acid or ester thereof of claim 36, wherein:
Ar$^1$ is 4-chloro-3-methyl-5-isoxazolyl;
W is —NH—; and
$R^{20}$ is CONH$^2$, COOH, or phenyl.

51. A sulfonamide or pharmaceutically acceptable salt, acid or ester thereof of claim 1, wherein the compound is $N^2$-(3-hydroxy-2,4,6-trimethyl)phenyl-3-(4-chloro-3-methyl-5-isoxazolyl)sulfamoyl-2-thiophenecarboxamide or a pharmaceutically acceptable salt thereof.

52. The compounds of claim 1 that are pharmaceutically acceptable sodium salts.

53. A pharmaceutical composition, comprising an effective amount of a compound of claim 1 or a pharmaceutically acceptable salt, acid or ester thereof in a pharmaceutically acceptable carrier, wherein the amount is effective for ameliorating the symptoms of an endothelin-mediated disease.

54. The composition of claim 53 that is formulated for single or multiple dosage administration.

55. An article of manufacture, comprising packaging material and a compound or a pharmaceutically acceptable salt, acid or ester thereof of claim 1 within the packaging material, wherein the compound is effective for antagonizing the effects of endothelin, ameliorating the symptoms of an endothelin-mediated disorder, or inhibiting the binding of an endothelin peptide to an ET receptor with an IC$_{50}$ of less than about 10 μM, and the packaging material includes a label that indicates that the sulfonamide or salt thereof is used for antagonizing the effects of endothelin, inhibiting the binding of endothelin to an endothelin receptor or treating an endothelin-mediated disorder.

56. A method for the treatment of endothelin-mediated diseases, comprising administering to a subject an effective amount the pharmaceutical composition of claim 43, wherein the effective amount is sufficient to ameliorate one or more of the symptoms of the disease.

57. The method of claim 56, wherein the disease is selected from the group consisting of hypertension, cardiovascular disease, asthma, pulmonary hypertension, inflammatory diseases, ophthalmologic disease, menstrual disorders, obstetric conditions, wounds, gastroenteric disease, renal failure, immunosuppressant-mediated renal vasoconstriction, erythropoietin-mediated vasoconstriction endotoxin shock, pulmonary hypertension, anaphylactic shock and hemorrhagic shock.

58. The method of claim 57, wherein the disease is selected from the group consisting of asthma and inflammatory diseases.

59. A method for inhibiting the binding of an endothelin peptide to endothelin$_A$ (ET$_A$) or endothelin$_B$ (ET$_B$) receptors, comprising contacting the receptors an endothelin peptide and with a compound or pharmaceutically acceptable salt, acid or ester thereof of claim 1, wherein:

the contacting is effected prior to, simultaneously with or subsequent to contacting the receptors with the endothelin peptide.

60. A method for altering endothelin receptor-mediated activity, comprising contacting endothelin receptors with a compound or pharmaceutically acceptable salt, acid or ester thereof of claim 1.

61. The pharmaceutical composition of claim 53, that comprises a sodium phosphate buffer solution having a sugar and a sulfonamide of claim 1 dissolved therein.

62. The pharmaceutical formulation of claim 61, wherein the sulfonamide is a pharmaceutically-acceptable salt that is an alkali metal.

63. A sulfonamide compound or pharmaceutically acceptable acid, salt or ester of a compound of claim 6, wherein, when Ar$^1$ is 4-chloro-3-methyl-5-isoxazolyl and W is —NH—:

(a) if R$^7$, R$^8$ and R$^{10}$ are methyl; then R$^9$ is not cyanomethyl, hydroxymethyl, cyano, methoxycarbonyl, carboxyl, methanesulfonyl, or 2-hydroxyethyl;

(b) if R$^{10}$ is methoxy or is methyl when R$^8$ and R$^9$ together form methylenedioxy and R$^8$ and R$^9$ are methoxy or together form methylenedioxy; then R$^7$ is not methyl, cyano, acetyl, methoxycarbonyl, carboxyl, methanesulfonyl, cyanomethyl or 2-hydroxyethyl, and is not methoxy when R$^{10}$ is methyl;

(c) if R$^{10}$ is cyano or acetyl and R$^8$ and R$^9$ together form methylenedioxy; then R$^7$ is not methyl or methoxy; and (d) if R$^{10}$ is cyanomethyl and R$^8$ and R$^9$ together form methylenedioxy; then R$^7$ is not cyanomethyl; and when W is —NHC(R$^{12}$)(R$^{16}$)—, then R$^7$, R$^8$, R$^9$ and R$^{10}$ are H or are selected as in (i) or (ii).

64. The pharmaceutical composition of claim 53 that is formulated as a tablet or capsule.

65. The composition of claim 64 wherein the compound is N$^2$-(3-hydroxy-2,4,6-trimethyl)phenyl-3-(4-chloro-3-methyl-5-isoxazolyl)sulfamoyl-2-thiophenecarboxamide.

66. A composition of claim 64, further comprising an enteric coating.

67. The composition of claim 66, wherein the coating is selected from cellulose acetate phthalate, polyethylene glycol, polyoxyethylene sorbitan, castor oil, ethyl cellulose pseudolatex, phenyl salicylate, n-butyl stearate, stearic acid and carnuba wax.

68. A sulfonamide or pharmaceutically acceptable salt, acid or ester thereof of claim 1, wherein Ar$^1$ selected from the group consisting of isoxazolyl, pyridazinyl, thiazolyl and pyrimidinyl groups.

69. A sulfonamide or pharmaceutically acceptable salt, acid or ester thereof of claim 6, wherein Ar$^1$ selected from the group consisting of isoxazolyl, pyridazinyl, thiazolyl and pyrimidinyl groups.

70. A sulfonamide or pharmaceutically acceptable salt, acid or ester thereof of claim 6, wherein Ar$^1$ is a substituted or unsubstituted 3- or 5-isoxazolyl, benzo-2,1,3-thiadiazol-5-yl, 2-pyrazinyl or benzo-2,1,3-oxadiazol-5yl group, and the substituents are H, NH$_2$, halide, CH$_3$, CH$_3$O or another aromatic group.

71. A sulfonamide or pharmaceutically acceptable salt, acid or ester thereof of claim 1, wherein: Ar$^1$ is a substituted or unsubstituted 3- or 5-isoxazolyl, benzo-2,1,3-thiadiazol-5-yl, 2-pyrazinyl or benzo-2,1,3-oxadiazol-5-yl group, and the substituents are independently selected from H, NH$_2$, halide, CH$_3$, CH$_3$O and another aromatic group; R$^{11}$ has 1–6 carbon atoms; and R$^6$ is selected from the group consisting of H and substituted or unsubstituted lower alkyl.

72. A sulfonamide or pharmaceutically acceptable salt, acid or ester thereof of claim 1, wherein M is (CH$_2$)$_m$C(O)(CH$_2$)$_r$, (CH$_2$)$_m$C(O)NH(CH$_2$)$_r$, (CH$_2$)$_m$(CH=CH)(CH$_2$)$_r$, (CH$_2$)$_m$C(O)(CH$_2$)$_s$NH(CH$_2$)$_r$, (CH$_2$)$_m$(CH=CH)(CH$_2$)$_r$, C=N(OH)(CH$_2$)$_r$, CH(OH)(CH$_2$)$_r$, (CH$_2$)$_r$, CH($_2$)$_r$O, (CH$_2$)S(O)$_n$, or C(O)O.

73. A sulfonamide or pharmaceutically acceptable salt, acid or ester thereof of claim 1 selected with the proviso that the sulfonamide compound is not selected from the group consisting of:

N-(4-chloro-3-methyl-5-isoxazolyl)-2-(3-cyanomethyl-2,4, 6-trimethylphenylaminocarbonyl)thiophene-3-sulfonamide;

N-(4-chloro-3-methyl-5-isoxazolyl)-2-(3-hydroxymethyl-2, 4,6-trimethylphenylaminocarbonyl)thiophene-3-sulfonamide;

N-(4-chloro-3-methyl-5-isoxazolyl)-2-(3-cyano-2,4,6-trimethylphenylaminocarbonyl)thiophene-3-sulfonamide;

N-(4-chloro-3-methyl-5-isoxazolyl)-2-(3-methoxycarbonyl-2,4,6-trimethylphenylaminocarbonyl)thiophene-3-sulfonamide;

N-(4-chloro-3-methyl-5-isoxazolyl)-2-(3-carboxyl-2,4,6-trimethylphenylaminocarbonyl)thiophene-3-sulfonamide;

N-(4-chloro-3-methyl-5-isoxazolyl)-2-(3-methanesulfonyl-2,4,6-trimethylphenylaminocarbonyl)thiophene-3-sulfonamide;

N-(4-chloro-3-methyl-5-isoxazolyl)-2-(3-(2-hydroxyethyl)-2,4,6-trimethylphenylaminocarbonyl)thiophene-3-sulfonamide;

N-(4-chloro-3-methyl-5-isoxazolyl)-2-(3-cyanomethyl-2,4, 6-trimethylphenylacetyl)thiophene-3-sulfonamide;

N-(4-chloro-3-methyl-5-isoxazolyl)-2-(3-hydroxymethyl-2, 4,6-trimethylphenylacetyl)thiophene-3-sulfonamide;

N-(4-chloro-3-methyl-5-isoxazolyl)-2-(3-cyano-2,4,6-trimethylphenylacetyl)thiophene-3-sulfonamide;

N-(4-chloro-3-methyl-5-isoxazolyl)-2-(3-methoxycarbonyl-2,4,6-trimethylphenylacetyl)thiophene-3-sulfonamide;

N-(4-chloro-3-methyl-5-isoxazolyl)-2-(3-carboxyl-2,4,6-trimethylphenylacetyl)thiophene-3-sulfonamide;
N-(4-chloro-3-methyl-5-isoxazolyl)-2-(3-methanesulfonyl-2,4,6-trimethylphenylacetyl)thiophene-3-sulfonamide;
N-(4-chloro-3-methyl-5-isoxazolyl)-2-(3-(2-hydroxyethyl)-2,4,6-trimethylphenylacetyl)thiophene-3-sulfonamide;
N-(4-chloro-3-methyl-5-isoxazolyl)-2-(6-methyl-2,3,4-trimethoxyphenylaminocarbonyl)thiophene-3-sulfonamide;
N-(4-chloro-3-methyl-5-isoxazolyl)-2-(6-acetyl-2,3,4-trimethoxyphenylaminocarbonyl)thiophene-3-sulfonamide;
N-(4-chloro-3-methyl-5-isoxazolyl)-2-(6-methoxycarbonyl-2,3,4-trimethoxyphenylaminocarbonyl)thiophene-3-sulfonamide;
N-(4-chloro-3-methyl-5-isoxazolyl)-2-(6-carboxyl-2,3,4-trimethoxyphenylaminocarbonyl)thiophene-3-sulfonamide;
N-(4-chloro-3-methyl-5-isoxazolyl)-2-(6-methanesulfonyl-2,3,4-trimethoxyphenylaminocarbonyl)thiophene-3-sulfonamide;
N-(4-chloro-3-methyl-5-isoxazolyl)-2-(6-cyanomethyl-2,3,4-trimethoxyphenylaminocarbonyl)thiophene-3-sulfonamide;
N-(4-chloro-3-methyl-5-isoxazolyl)-2-(6-(2-hydroxyethyl)-2,3,4-trimethoxyphenylaminocarbonyl)thiophene-3-sulfonamide;
N-(4-chloro-3-methyl-5-isoxazolyl)-2-(6-cyano-2,3,4-trimethoxyphenylaminocarbonyl)thiophene-3-sulfonamide;
N-(4-chloro-3-methyl-5-isoxazolyl)-2-(6-methyl-2,3,4-trimethoxyphenylacetyl)thiophene-3-sulfonamide;
N-(4-chloro-3-methyl-5-isoxazolyl)-2-(6-acetyl-2,3,4-trimethoxyphenylacetyl)thiophene-3-sulfonamide;
N-(4-chloro-3-methyl-5-isoxazolyl)-2-(6-methoxycarbonyl-2,3,4-trimethoxyphenylacetyl)thiophene-3-sulfonamide;
N-(4-chloro-3-methyl-5-isoxazolyl)-2-(6-carboxyl-2,3,4-trimethoxyphenylacetyl)thiophene-3-sulfonamide;
N-(4-chloro-3-methyl-5-isoxazolyl)-2-(6-methanesulfonyl-2,3,4-trimethoxyphenylacetyl)thiophene-3-sulfonamide;
N-(4-chloro-3-methyl-5-isoxazolyl)-2-(6-cyanomethyl-2,3,4-trimethoxyphenylacetyl)thiophene-3-sulfonamide;
N-(4-chloro-3-methyl-5-isoxazolyl)-2-(6-(2-hydroxyethyl)-2,3,4-trimethoxyphenylacetyl)thiophene-3-sulfonamide;
N-(4-chloro-3-methyl-5-isoxazolyl)-2-(6-methyl-3,4-(methylenedioxy)-2-methoxyphenylaminocarbonyl)thiophene-3-sulfonamide;
N-(4-chloro-3-methyl-5-isoxazolyl)-2-(6-acetyl-3,4-(methylenedioxy)-2-methoxyphenylaminocarbonyl)thiophene-3-sulfonamide;
N-(4-chloro-3-methyl-5-isoxazolyl)-2-(6-methoxycarbonyl-3,4-(methylenediioxy)-2-methoxyphenylaminocarbonyl)thiophene-3-sulfonamide;
N-(4-chloro-3-methyl-5-isoxazolyl)-2-(6-carboxyl-3,4-(methylenedioxy)-2-methoxyphenylaminocarbonyl)thiophene-3-sulfonamide;
N-(4-chloro-3-methyl-5-isoxazolyl)-2-(6-methanesulfonyl-3,4-(methylenedioxy)-2-methoxyphenylaminocarbonyl)thiophene-3-sulfonamide;
N-(4-chloro-3-methyl-5-isoxazolyl)-2-(6-cyanomethyl-3,4-(methylenedioxy)-2-methoxyphenylaminocarbonyl)thiophene-3-sulfonamide;
N-(4-chloro-3-methyl-5-isoxazolyl)-2-(6-(2-hydroxyethyl)-3,4-(methylenedioxy)-2-methoxyphenylaminocarbonyl)thiophene-3-sulfonamide;
N-(4-chloro-3-methyl-5-isoxazolyl)-2-(6-cyano-3,4-(methylenedioxy)-2-methoxyphenylaminocarbonyl)thiophene-3-sulfonamide;
N-(4-chloro-3-methyl-5-isoxazolyl)-2-(2,6-dimethyl-3,4-(methylenedioxy)phenylaminocarbonyl)thiophene-3-sulfonamide;
N-(4-chloro-3-methyl-5-isoxazolyl)-2-(6-acetyl-3,4-(methylenedioxy)-2-methylphenylaminocarbonyl)thiophene-3-sulfonamide;
N-(4-chloro-3-methyl-5-isoxazolyl)-2-(6-methoxycarbonyl-3,4-(methylenedioxy)-2-methylphenylaminocarbonyl)thiophene-3-sulfonamide;
N-(4-chloro-3-methyl-5-isoxazolyl)-2-(6-carboxyl-3,4-(methylenedioxy)-2-methylphenylaminocarbonyl)thiophene-3-sulfonamide;
N-(4-chloro-3-methyl-5-isoxazolyl)-2-(6-methanesulfonyl-3,4-(methylenedioxy)-2-methylphenylaminocarbonyl)thiophene-3-sulfonamide;
N-(4-chloro-3-methyl-5-isoxazolyl)-2-(6-cyanomethyl-3,4-(methylenedioxy)-2-methylphenylaminocarbonyl)thiophene-3-sulfonamide;
N-(4-chloro-3-methyl-5-isoxazolyl)-2-(6-(2-hydroxyethyl)-3,4-(methylenedioxy)-2-methylphenylaminocarbonyl)thiophene-3-sulfonamide;
N-(4-chloro-3-methyl-5-isoxazolyl)-2-(6-cyano-3,4-(methylenedioxy)-2-methylphenylaminocarbonyl)thiophene-3-sulfonamide;
N-(4-chloro-3-methyl-5-isoxazolyl)-2-(6-methoxy-3,4-(methylenedioxy)-2-methylphenylaminocarbonyl)thiophene-3-sulfonamide;
N-(4-chloro-3-methyl-5-isoxazolyl)-2-(2-cyano-3,4-(methylenedioxy)-6-methylphenylaminocarbonyl)thiophene-3-sulfonamide;
N-(4-chloro-3-methyl-5-isoxazolyl)-2-(2-cyano-3,4-(methylenedioxy)-6-methoxyphenylaminocarbonyl)thiophene-3-sulfonamide;
N-(4-chloro-3-methyl-5-isoxazolyl)-2-(2-acetyl-3,4-(methylenedioxy)-6-methylphenylaminocarbonyl)thiophene-3-sulfonamide;
N-(4-chloro-3-methyl-5-isoxazolyl)-2-(2-acetyl-3,4-(methylenedioxy)-6-methoxyphenylaminocarbonyl)thiophene-3-sulfonamide;
N-(4-chloro-3-methyl-5-isoxazolyl)-2-(6-methyl-3,4-(methylenedioxy)-2-methoxyphenylacetyl)thiophene-3-sulfonamide;
N-(4-chloro-3-methyl-5-isoxazolyl)-2-(6-acetyl-3,4-(methylenedioxy)-2-methoxyphenylacetyl)thiophene-3-sulfonamide;
N-(4-chloro-3-methyl-5-isoxazolyl)-2-(6-methoxycarbonyl-3,4-(methylenedioxy)-2-methoxyphenylacetyl)thiophene-3-sulfonamide;
N-(4-chloro-3-methyl-5-isoxazolyl)-2-(6-carboxyl-3,4-(methylenedioxy)-2-methoxyphenylacetyl)thiophene-3-sulfonamide;
N-(4-chloro-3-methyl-5-isoxazolyl)-2-(6-methanesulfonyl-3,4-(methylenedioxy)-2-methoxyphenylacetyl)thiophene-3-sulfonamide;
N-(4-chloro-3-methyl-5-isoxazolyl)-2-(6-cyanomethyl-3,4-(methylenedioxy)-2-methoxyphenylacetyl)thiophene-3-sulfonamide;
N-(4-chloro-3-methyl-5-isoxazolyl)-2-(6-(2-hydroxyethyl)-3,4-(methylenedioxy)-2-methoxyphenylacetyl)thiophene-3-sulfonamide;
N-(4-chloro-3-methyl-5-isoxazolyl)-2-(6-cyano-3,4-(methylenedioxy)-2-methylphenylacetyl)thiophene-3-sulfonamide;
N-(4-chloro-3-methyl-5-isoxazolyl)-2-(2,6-dimethyl-3,4-(methylenedioxy)phenylacetyl)thiophene-3-sulfonamide;

N-(4-chloro-3-methyl-5-isoxazolyl)-2-(6-acetyl-3,4-(methylenedioxy)-2methylphenylacetyl)thiophene-3-sulfonamide;

N-(4-chloro-3-methyl-5-isoxazolyl)-2-(6-methoxycarbonyl-3,4-(methylenedioxy)-2-methylphenylacetyl)thiophene-3-sulfonamide;

N-(4-chloro-3-methyl-5-isoxazolyl)-2-(6-carboxyl-3,4-(methylenedioxy)-2-methylphenylacetyl)thiophene-3-sulfonamide;

N-(4-chloro-3-methyl-5-isoxazolyl)-2-(6-methanesulfonyl-3,4-(methylenedioxy)-2-methylphenylacetyl)thiophene-3-sulfonamide;

N-(4-chloro-3-methyl-5-isoxazolyl)-2-(6-cyanomethyl-3,4-methylenedioxy)-2-methylphenylacetyl)thiophen-3-sulfonamide;

N-(4-chloro-3-methyl-5-isoxazolyl)-2-(6-(2-hydroxyethyl)-3,4-(methylenedioxy)-2-methylphenylacetyl)thiophene-3-sulfonamide;

N-(4-chloro-3-methyl-5-isoxazolyl)-2-(6-cyano-3,4-(methylenedioxy)-2-methylphenylacetyl)thiophene-3-sulfonamide;

N-(4-chloro-3-methyl-5-isoxazolyl)-2-(6-methoxy-3,4-(methylenedioxy)-2-methylphenylacetyl)thiophene-3-sulfonamide;

N-(4-chloro-3-methyl-5-isoxazolyl)-2-(2-cyano-3,4-(methylenedioxy)-6-methylphenylacetyl)thiophene-3-sulfonamide;

N-(4-chloro-3-methyl-5-isoxazolyl)-2-(2-cyano-3,4-(methylenedioxy)-6-methoxyphenylacetyl)thiophene-3-sulfonamide;

N-(4-chloro-3-methyl-5-isoxazolyl)-2-(2-acetyl-3,4-(methylenedioxy)-6-methylphenylacetyl)thiophene-3-sulfonamide;

N-(4-chloro-3-methyl-5-isoxazolyl)-2-(2-acetyl-3,4-(methylenedioxy)-6-methoxyphenylacetyl)thiophene-3-sulfonamide; and N-(4-chloro-3-methyl-5-isoxazolyl)-2-(2,6-bis(cyanomethyl)-3,4-(methylenedioxy)phenylaminocarbonyl)thiophene-3-sulfonamide.

* * * * *

UNITED STATES PATENT AND TRADEMARK OFFICE
CERTIFICATE OF CORRECTION

PATENT NO.    : 6,420,567 B1
DATED         : July 16, 2002
INVENTOR(S)   : Wu et al.

It is certified that error appears in the above-identified patent and that said Letters Patent is hereby corrected as shown below:

<u>Title page,</u>
Item [54], replace "DERVIATIVES" with -- DERIVATIVES --
References Cited, U.S. PATENT DOCUMENTS, replace U.S. Patent No. "6,083,851" with -- 6,083,951 --
U.S. PATENT DOCUMENTS, add the following:

| | | | |
|---|---|---|---|
| -- 6017916 | 01/25/00 | Berryman et al. | 514/233.8 |
| 6017951 | 01/25/00 | Patt et al. | 514/464 |
| 6043241 | 03/28/00 | Cheng et al. | 514/233.8 |
| 6043265 | 03/28/00 | Murugesan et al. | 514/374 |
| 6060475 | 05/09/00 | Bradbury et al. | 541/255 |
| 6063911 | 05/16/00 | Vournakis et al. | 536/20 |
| 6083955 | 07/04/00 | Harada et al. | 514/269 |
| 6107320 | 08/22/00 | Murugesan et al. | 514/379 |
| 6133263 | 10/17/00 | Cheng et al. | 514/233.8 |
| 6133442 | 10/17/00 | Breu et al. | 544/123 -- |

<u>Column 101, lines 65-67 through Column 102, lines 1-35,</u>
Claim 38 should read as follows:
  38. A sulfonamide or pharmaceutically acceptable salt, acid or ester thereof of claim 1, wherein the compounds of formula (A) are of formula (IV):

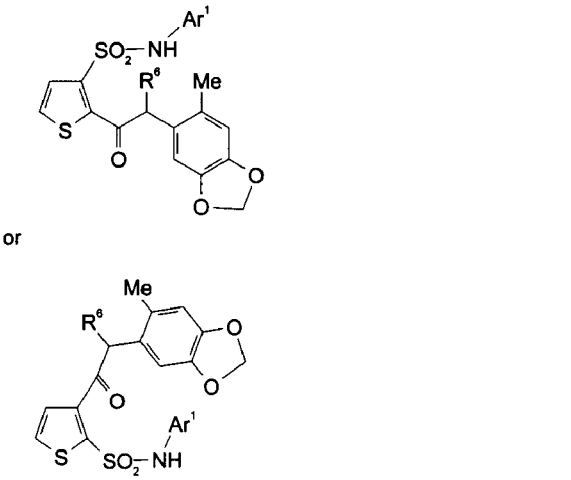

or

UNITED STATES PATENT AND TRADEMARK OFFICE
CERTIFICATE OF CORRECTION

PATENT NO. : 6,420,567 B1
DATED : July 16, 2002
INVENTOR(S) : Wu et al.

It is certified that error appears in the above-identified patent and that said Letters Patent is hereby corrected as shown below:

<u>Column 101, lines 65-67 through Column 102, lines 1-35 (cont'd)</u>,
wherein:
    $Ar^1$ is selected with the proviso that $Ar^1$ is not 4-chloro-3-methyl-5-isoxazolyl, 4-chloro-5-methyl-3-isoxazolyl or 3,4-dimethyl-5-isoxazolyl when $R^6$ is H; and
    $R^6$ is H, or substituted or unsubstituted alkyl or aryl.

Signed and Sealed this

Thirty-first Day of December, 2002

JAMES E. ROGAN
*Director of the United States Patent and Trademark Office*